United States Patent
Shaaltiel et al.

(10) Patent No.: US 8,119,406 B2
(45) Date of Patent: Feb. 21, 2012

(54) SYSTEM AND METHOD FOR PRODUCTION OF ANTIBODIES IN PLANT CELL CULTURE

(75) Inventors: Yoseph Shaaltiel, Moshav Beit-Hillel Doar-Na Galil Elyon (IL); Sharon Hashmueli, Yesod-HaMaala (IL); Daniel Bartfeld, Kiryat Shmona (IL); Gideon Baum, Kibbutz Ayelet HaShachar (IL); Tal Ratz, D.N. Galil Elyon (IL); Einat Mizrachi, Kfar Yehezkel (IL); Yehava Forester, D.N. Galil Elyon (IL)

(73) Assignee: Protalix Ltd., Carmiel (IL)

( * ) Notice: Subject to any disclaimer, the term of this patent is extended or adjusted under 35 U.S.C. 154(b) by 201 days.

(21) Appl. No.: 11/665,344

(22) PCT Filed: Oct. 11, 2005

(86) PCT No.: PCT/IL2005/001075
§ 371 (c)(1), (2), (4) Date: Nov. 17, 2008

(87) PCT Pub. No.: WO2006/040764
PCT Pub. Date: Apr. 20, 2006

(65) Prior Publication Data
US 2009/0082548 A1     Mar. 26, 2009

Related U.S. Application Data

(60) Provisional application No. 60/617,646, filed on Oct. 13, 2004.

(51) Int. Cl.
*C12N 5/14* (2006.01)
*C12P 21/02* (2006.01)
(52) U.S. Cl. .................. 435/419; 435/414; 435/69.6
(58) Field of Classification Search .................. None
See application file for complete search history.

(56) References Cited

U.S. PATENT DOCUMENTS

| | | | |
|---|---|---|---|
| 6,080,560 A | 6/2000 | Russell et al. | |
| 6,709,862 B2 | 3/2004 | Curtis | |
| 2002/0015708 A1 | 2/2002 | Stram et al. | |
| 2002/0064526 A1 | 5/2002 | Pollack | |
| 2003/0084482 A1* | 5/2003 | Hall et al. | 800/288 |

FOREIGN PATENT DOCUMENTS

| | | |
|---|---|---|
| EP | 1431394 | 6/2004 |
| EP | 1799813 | 6/2007 |
| WO | WO 99/66026 | 12/1999 |
| WO | WO 03/013598 | 2/2003 |
| WO | WO 2004/050838 | 6/2004 |
| WO | WO 2006/040764 | 4/2006 |

OTHER PUBLICATIONS

Communication Pursuant to Article 96(2) EPC Dated Nov. 26, 2007 From the European Patent Office Re.: Application No. 05796809.1.
European Search Report Dated Nov. 22, 2007 From the European Patent Office Re.: Application No. 05796809.1.
International Preliminary Report on Patentability Dated Apr. 26, 2007 From the International Bureau of WIPO Re.: Application No. PCT/IL2005/001075.
Invitation Pursuant to Article 94(3) and Rule 71(1) EPC Dated Apr. 28, 2009 From the European Patent Office Re.: Application No. 05796809.1.
Search Report and Written Opinion Dated Apr. 14, 2009 From the Intellectual Property Office of Singapore issued by the Austrian Patent Office Re.: Application No. 200702758-4.
Search Report Dated Dec. 23, 2008 From the Intellectual Property Office of Singapore Issued by the Australian Patent Office Re.: SG 200800359-2.
Written Opinion Dated Dec. 23, 2008 From the Intellectual Property Office of Singapore Issued by the Australian Patent Office Re.: Application No. SG 200800359-2.
Giddings et al. "Transgenic Plants as Factories for Biopharmaceuticals", Nature Biotechnology, XP002988986, 18(11): 1151-1155, Nov. 2000.
Stoger et al. "Practical Considerations for Pharmaceutical Antibody Production in Different Crop Systems", Molecular Breeding, 9: 149-158, 2002. col. 3, Line 11-col. 6, Line 3.
Chargelegue et al. "A Murine Monoclonal Antibody Produced in Transgenic Plants With Plant-Specific Glycans Is Not Immunogenic in Mice", Transgenic Research, 9: 187-194, 2000. p. 187, r-h col. § 1, 2, p. 188, 1-h col. § 1, p. 193, 1-h col. § 1.
Fischer et al. "Affinity-Purification of A TMV-Specific Recombinant Full-Size Antibody From A Transgenic Tobacco Suspension Culture", Journal of Immunological Methods, 226(1-2): 1-10, 1999. p. 3, 1-h col. § 2-4.
Syrkin Wurtele et al. "A Simple, Efficient Method for the *Agrobacterium*-Mediated Transformation of Carrot Callus Cells", Plant Science, 61(2): 253-262, 1989. p. 254, 1-h col. § 3.
Office Action Dated Sep. 30, 2009 From the Israeli Patent Office Re.: Application No. 182517 and Its Translation Into English.
International Search Report Dated May 12, 2006 From the International Searching Authority Re.: Application No. PCT/IL2005/001075.
Response Dated Jan. 31, 2010 to Office Action of Sep. 30, 2009 From the Israeli Patent Office Re.: Application No. 182517.
Written Opinion Dated May 12, 2006 From the International Searching Authority Re.: Application No. PCT/IL2005/001075.
Examination Report Dated Apr. 8, 2010 From the Instituto Mexicano de la Propriedad Industrial Re. Application No. MX/a/2007/004414 and Its Summary Into English.
Response Dated Aug. 18, 2010 to Examination Report of Apr. 8, 2010 From the Instituto Mexicano de la Propriedad Industrial Re. Application No. MX/a/2007/004414.
Office Action Dated Aug. 16, 2010 From the Israeli Patent Office Re.: Application No. 182517 and Its Translation Into English.
Response Dated Dec. 15, 2010 to Office Action of Aug. 16, 2010 From the Israeli Patent Office Re.: Application No. 182517.

* cited by examiner

*Primary Examiner* — Sharon Wen

(57) ABSTRACT

A system and method for production of antibodies in plant cell culture, which results in highly functional antibodies, produced with a high level of expression efficiency. The present invention also encompasses host cells, vectors and methods for mass production of full size assembled immunoglobulins.

8 Claims, 33 Drawing Sheets
(16 of 33 Drawing Sheet(s) Filed in Color)

| Fig. 2a | Fig. 2b | Fig. 2c | Fig. 2d | Fig. 2e | Fig. 2f | Fig. 2g | Fig. 2h |
|---|---|---|---|---|---|---|---|
| Fig. 2i | Fig. 2j | Fig. 2k | Fig. 2l | Fig. 2m | Fig. 2n | Fig. 2o | Fig. 2p |

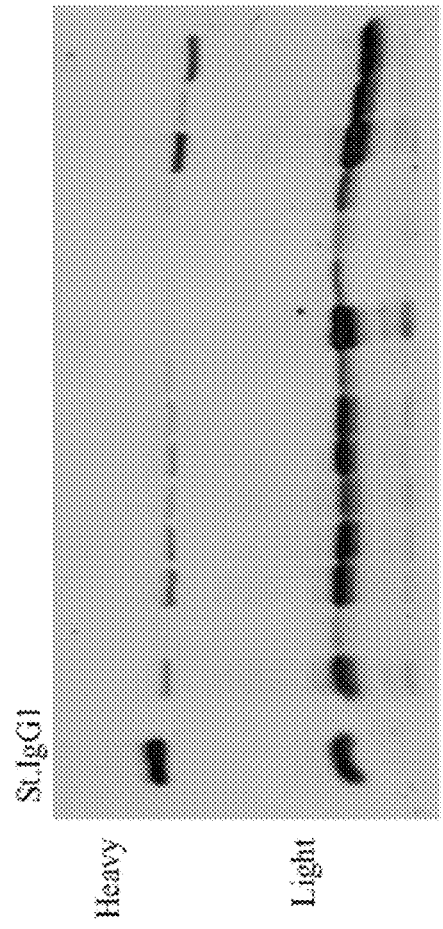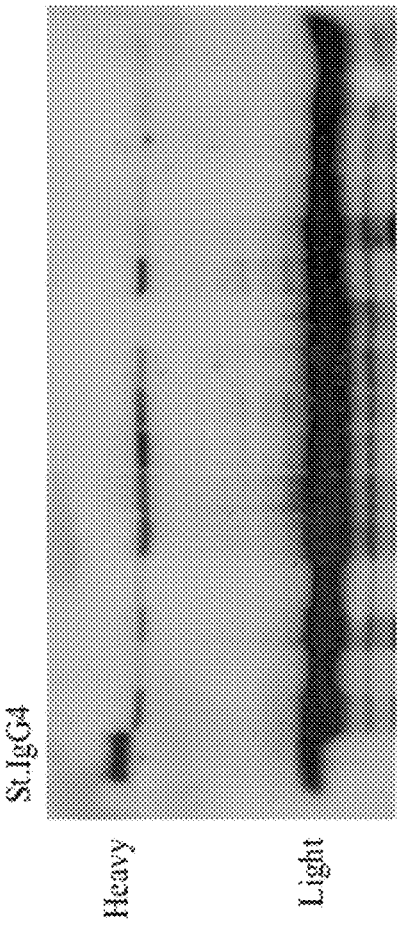
Fig. 4: Initial screening of IgG1 and IgG4 expression in transformed calli

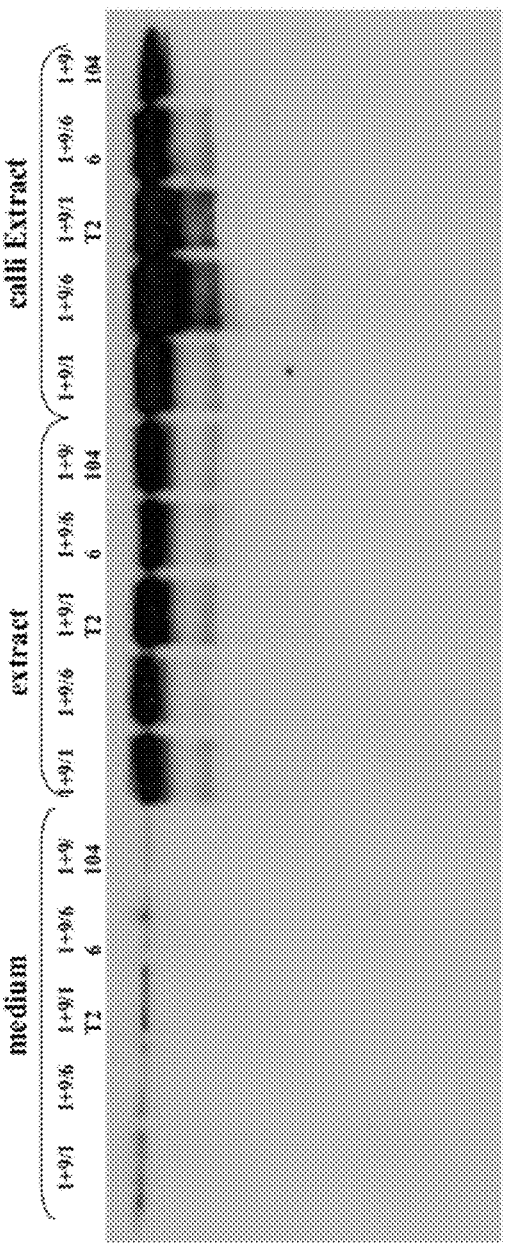
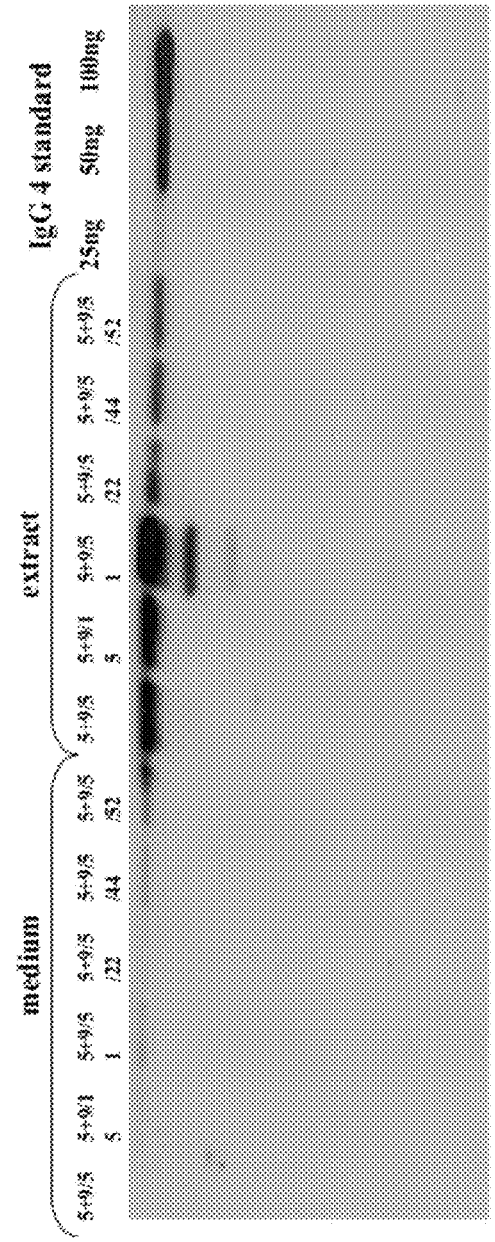
Fig. 5A
Fig. 5B
Fig. 5: Screening of productive lines expressing assembled IgG1 and IgG4

Fig. 6 : IgG1 extract separated on Macro Prep High S cation exchange column

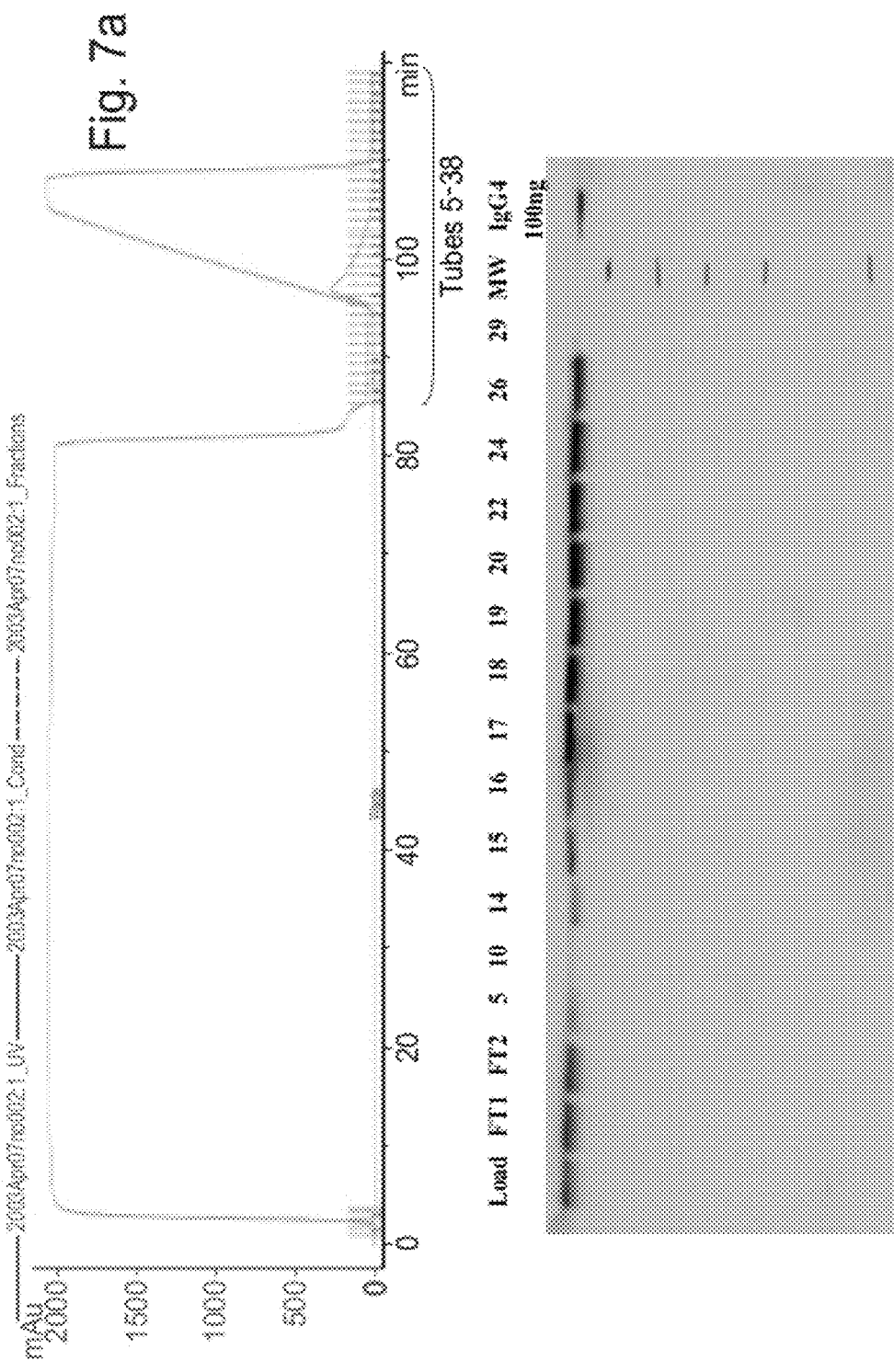
Fig. 7: IgG4 extract separated on Macro Prep High S cation exchange column

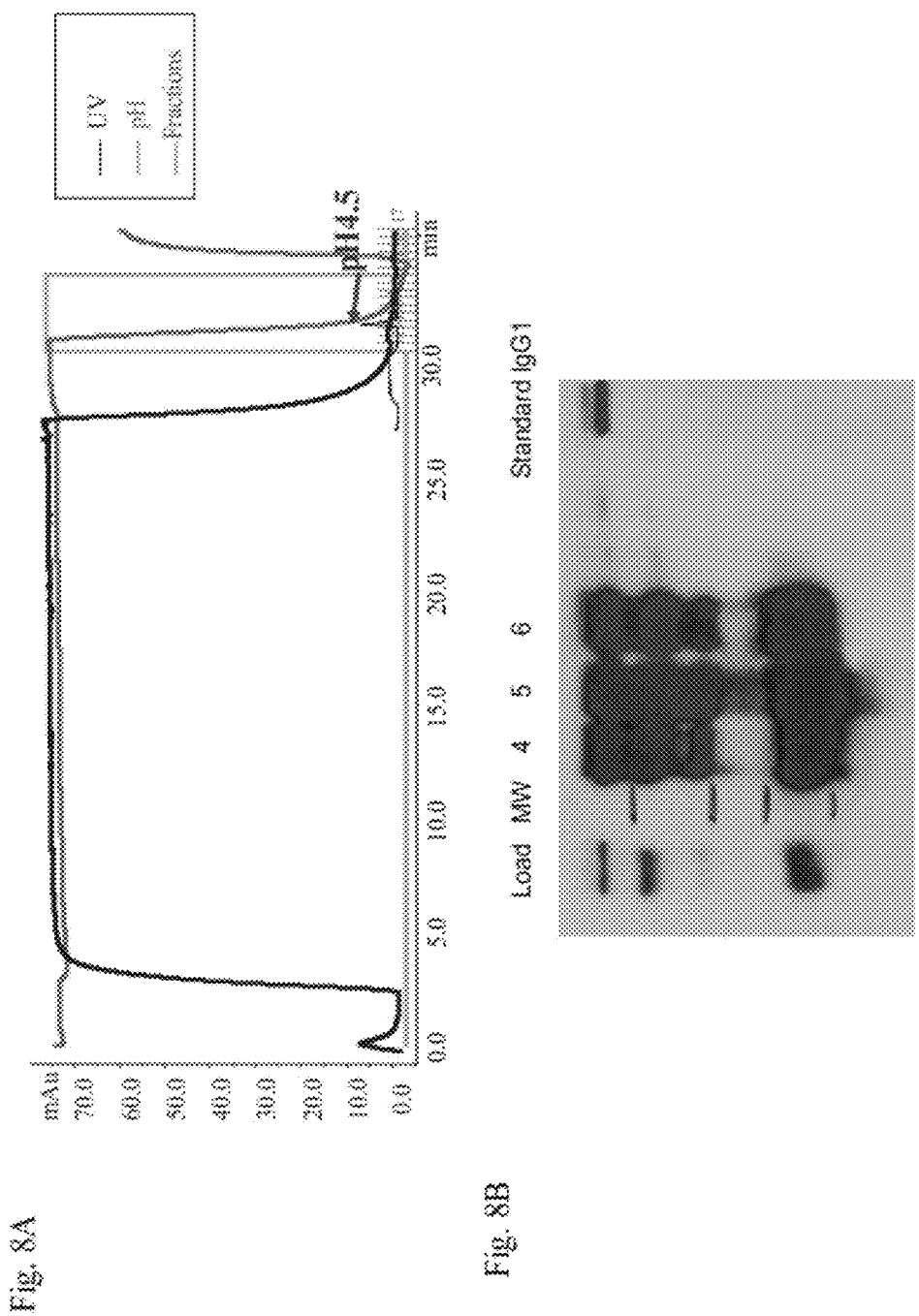
Fig. 8: IgG1 containing fractions from Cation exchange elution separated on Protein A sepharose.

Fig. 9 : IgG4 containing fractions from Cation exchange elution separated on Protein A sepharose.

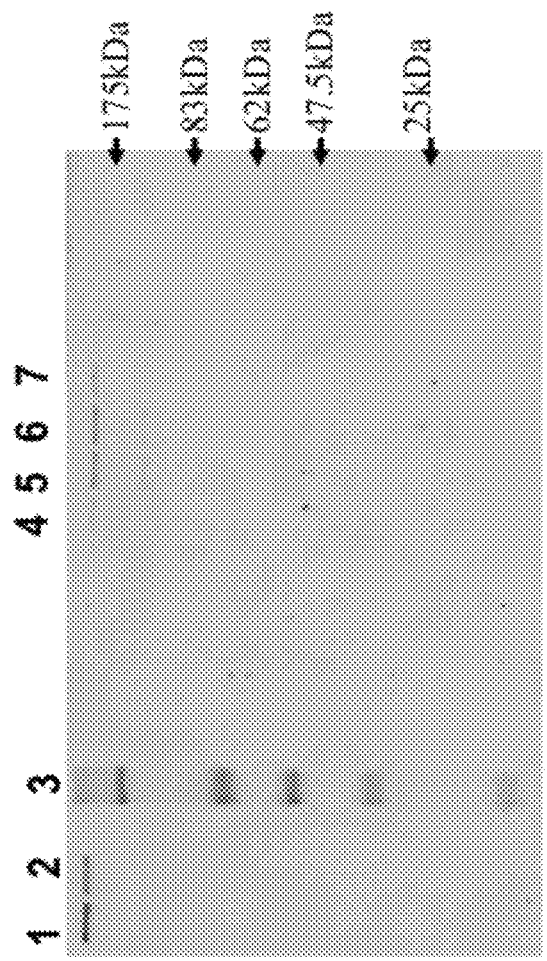
Fig. 10B Coomassie stain
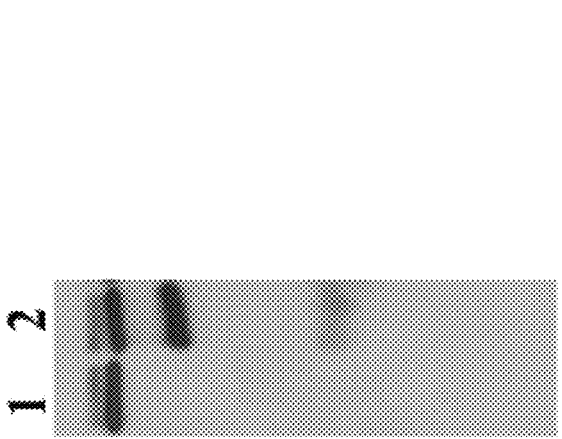
Fig. 10A Western blot analysis

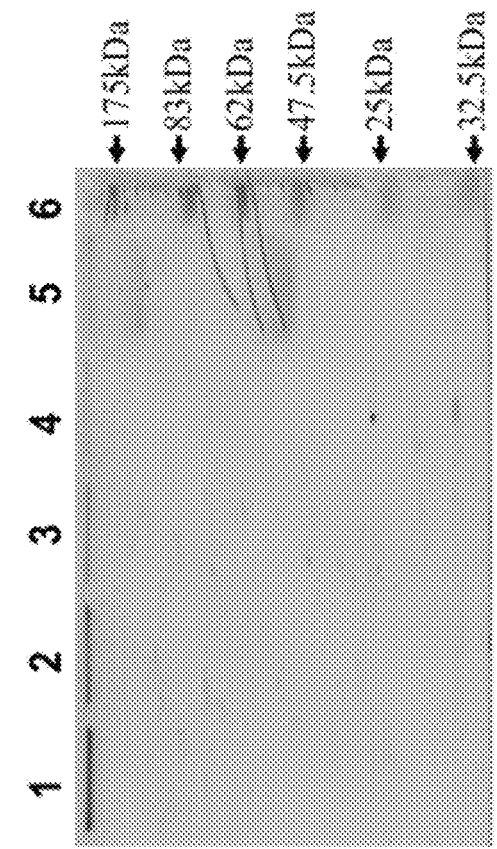
Fig. 11B Coomassie stain
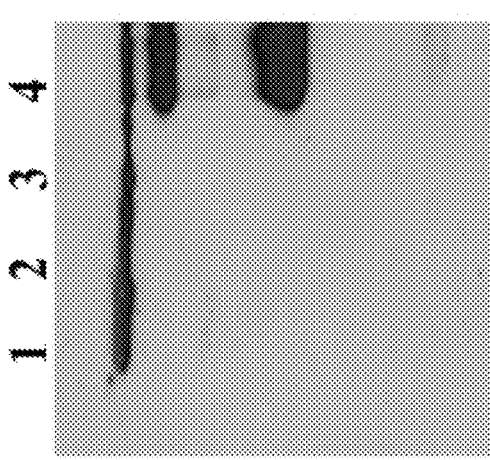
Fig. 11A Western blot analysis

SYSTEM AND METHOD FOR PRODUCTION OF ANTIBODIES IN PLANT CELL CULTURE

RELATED APPLICATIONS

This Application is a National Phase of PCT Patent Application No. PCT/IL2005/001075 having International Filing Date of Oct. 11, 2005, which claims the benefit of U.S. Provisional Patent Application No. 60/617,646 filed on Oct. 13, 2004. The contents of the above Applications are all incorporated herein by reference.

FIELD OF THE INVENTION

The present invention is of a system and method for production of antibodies in plant cell culture, and also of the antibodies produced thereof.

BACKGROUND OF THE INVENTION

Antibodies represent a large proportion of therapeutic drugs currently in development. Antibodies are complex glycoproteins that recognize and bind to target antigens with great specificity. This specific binding activity allows antibodies to be used for a range of applications, including the diagnosis, prevention and treatment of disease (20). Typical full size antibodies are tetramers of two identical heavy chains and two identical light chains. Beyond full size immunoglobulins, other antibody derivatives of therapeutic value have been expressed in plants, including Fab fragments, scFvs, bispecific Fvs, diabodies, minibodies, single variable domains, antibody fusion proteins and more (4).

Glycosylation of IgG antibody molecules is a post translational modification that is important for recognition of the effector ligands FcR and complement. A complex biantennary oligosaccharide moiety is attached at Asn-297 in the CH2 domain of each heavy chain. Heterogeneity in the attachment of sugar residues is associated with functional modulation (21-26). Furthermore, studies show that the in-vivo fate of IgG1 antibodies is drastically affected by the presence of a carbohydrate of altered structure in CH2 (27).

Proteins for pharmaceutical use have been traditionally produced in mammalian or bacterial expression systems. In most cases, they are produced transgenically in mammalian cell lines, primarily Chinese hamster ovary (CHO), or transgenic animals because these have been shown to fold and assemble the proteins correctly and generate similar glycosylation patterns. However, such expression systems are expensive and are difficult to scale up to high levels of production. Furthermore, there are safety concerns due to potential contamination with pathogenic organisms or oncogenic DNA sequences. Also, the production yield and stability of certain subclasses, for example IgG4, in these mammalian systems is quite low, such that production is very inefficient.

Although the exact cause is not known, the stability of the recombinant IgG4 is low, which causes the yield to be low, and thereby leads to inefficient large scale production.

Therefore, clearly non-mammalian systems for production of antibodies and other therapeutic proteins would be advantageous. Although such systems have been shown to be operative for non-immunogenic proteins, antibodies are more sensitive and more difficult to produce in non-mammalian cell culture systems. For example although antibodies can be expressed in baculovirus expression systems and stably transfected insect cell lines, the resultant material may not have the necessary properties. Insect cell expression systems do produce antibodies, but have several deficiencies: inefficient processing and an impairment of the folding and secretion capacity, a high, in part baculovirus-encoded, protease activity, insufficient strength and deviations of the posttranslational modification pattern (which could act immunogenically)(see for example the following references: Guttieri M C, Liang M. 2004, Human antibody production using insect-cell expression systems. Methods Mol. Biol., 248:269-99, Guttieri M C, Sinha T, Bookwalter C, Liang M, Schmaljohn C S. 2003, Cassette vectors for conversion of Fab fragments into full-length human IgG1 monoclonal antibodies by expression in stably transformed insect cells. Hybrid Hybridomics. 22(3): 135-45, Potter K N, Li Y, Capra J D. 1993, Antibody production in the baculovirus expression system. Int Rev Immunol. 10(2-3):103-12). Antibodies cannot be produced in *E. coli* as there is no suitable post-translational modification.

In the past decade a new expression system has been developed in plants. This methodology utilizes *Agrobacterium*, a bacteria capable of inserting single stranded DNA molecules (T-DNA) into the plant genome (1). Due to the relative simplicity of introducing genes for mass production of proteins and peptides, this methodology is becoming increasingly popular as an alternative protein expression system in plants (2-4) (5).

Plant based systems represent an inexpensive, efficient and safe alternative for the production of recombinant antibodies. Production of full size antibodies in plant cells was first demonstrated in whole tobacco plants by sexual crossing of plants expressing single gamma or kappa immunoglobulin chains (6). Assembly of IgG (primarily IgG1) and IgA antibodies in *Nicotiana, Arabidopsis* and other plants has been described (3, 7-10).

Research over the last 10 years has shown that plant cells, contained in whole plants, can produce a variety of functional antibodies and there is now intense interest in scaling up production to commercial levels. (11-13), (14,15), (5, 16-18).

However there is rising concern about potential safety issues, including contamination with residual pesticides, herbicides and toxic plant metabolites, when using transgenic field crops to produce recombinant proteins (19). Groups opposed to genetically modified plants in general, afraid of the potential danger that transgenes and their encoded proteins will spread in the environment or into the food chain, and strict limitations of regulatory bodies have raised obstacles for companies utilizing transgenic plant technology for protein expression. Thus, clearly the use of whole, complete plants is disadvantageous.

Plant-suspension cells are an in vitro system that can be used for recombinant protein production under carefully controlled certified conditions. Plant cell suspensions can be grown in shaken flasks or bioreactors to produce recombinant proteins. The present inventors have filed corresponding applications for a bioreactor system which allows safe production of recombinant proteins, such as antibodies, utilizing the advantages of plant cell expression, without the potential hazard of open-field plant growth (see U.S. Pat. No. 6,391, 638 and U.S. patent application Ser. No. 10/784,295, filed on Feb. 24, 2004, both of which are hereby incorporated by reference as if fully set forth herein).

For example, expression of a TMV-specific full-size murine IgG-2b/K antibody in a *Nicotiana tabacum* cv. Petite Havana SR1 suspension culture (P9s) has been described (18). The integration of an N-terminal murine leader peptide directed the assembled immunoglobulin for secretion. However, in suspension culture, the full-size recombinant antibody was retained by the plant cell wall. An ELISA procedure demonstrated that the specificity and affinity of the recombinant antibody was indistinguishable from its murine counterpart, indicating the potential of plant cell suspension cultures as bio-reactors for the production of recombinant antibodies (18).

The production of antibodies in plants represents a special challenge because the molecules must fold and assemble correctly to recognize their cognate antigens. On the other hand, plant derived expression systems do facilitate post-translational modifications known to be crucial for protein expression and activity, unlike bacterial expression systems for example. However, there are significant differences in post-translational modifications between mammalian and plant cell culture systems, which need to be considered in order to avoid potential reduced or even eliminated functionality of the expressed protein.

One of the major differences between mammalian and plant protein expression system is the variation of protein sugar side chains, caused by the differences in biosynthetic pathways. Glycosylation was shown to have a profound effect on activity, folding, stability, solubility, susceptibility to proteases, blood clearance rate and antigenic potential of proteins. Hence, any protein production in plants should take into consideration the potential ramifications of plant glycosylation.

Protein glycosylation is divided into two categories: N-linked and O-linked modifications (28,29) (30). The two types differ in amino acid to which the glycan moiety is attached to—N-linked are attached to Asn residues, while O-linked are attached to Ser or Thr residues. In addition, the glycan sequence of each type bears unique distinguishing features. Of the two types, N-linked glycosylation is the more abundant, and its effect on protein function has been extensively studied. O-linked glycans, on the other hand are relatively scarce, and less information is available regarding their affect on proteins.

Several approaches have been discussed to control and tailor protein glycosylation in plants (31) (32). Gross modifications, such as complete inhibition of glycosylation or the removal of glycosylation sites from the peptide chain, may be implemented as one strategy. However, this approach can result in structural defects. An additional approach involves knock-out and introduction of specific carbohydrate processing enzymes. These enzymes are "knocked-out" to prevent potentially immunogenic sugars from being added during post-translational modification. For example, knock-out of the gene encoding for Xylosyltransferase would result in the absence of xylose in the glycan structure. Xylose is a sugar residue found only in plants and is thought to be potentially immunogenic. Introduction of human carbohydrate processing enzyme genes such as sialyltransferase to the plant results in the addition of sialic acid, which is not present in plants (see for example Ragon C, Lerouge P, Faye L., 1998 The protein N-glycosylation in plants, J. Exp. Botany Vol 49(326)1463-1472).

The third approach tries to localize the expression to a specific compartment in the cell. For example, retaining the protein in the ER prevents plant specific modification from being carried out in the Golgi (33) (34,35). Each cellular compartment has different carbohydrate processing enzymes. Proteins that enter or are targeted to the secretory pathway are transferred from the ER to the Golgi and then to the vacuola or apoplast. The apoplast is the space between the plant cell membrane and plant cell wall. Proteins that are targeted to secretion, or more specifically, are not targeted to a specific cell compartment and are therefore secreted, reach the apoplast. Some proteins remain there but some are passed through the cell wall and are secreted to the growth medium. Since different carbohydrate processing occurs in each compartment, retaining a protein in one compartment can inhibit further processing of the glycan structure, or, by directing a protein to a specific compartment, it is possible to ensure that the protein enters a desired processing pathway.

SUMMARY OF THE INVENTION

The background art does not teach or suggest a system or method for producing highly functional IgG4 antibodies.

The present invention overcomes these drawbacks of the background art by providing a system and method for production of antibodies in plant cell culture, which results in highly functional antibodies, produced with a high level of expression efficiency. The present invention also encompasses host cells, vectors and methods for mass production of full size assembled immunoglobulins.

According to preferred embodiments of the present invention, there is provided a plant expression system based on genetically modified (e.g., transgenic) plant cells grown in suspension. This expression system is particularly designed for production of intact antibodies (assembled) or antibody fragments.

These antibodies are preferably functional antibodies (i.e., capable of specifically binding a target antigen or having an effector function [e.g., activation of complement function, such as the IgG4.

As used herein, the term "antibody" refers to a substantially intact antibody molecule.

As used herein, the phrase "antibody fragment" refers to a functional fragment of an antibody that is capable of binding to an antigen.

Suitable antibody fragments for practicing the present invention include, inter alia, a complementarity-determining region (CDR) of an immunoglobulin light chain (referred to herein as "light chain"), a CDR of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as an Fv, a single-chain Fv, an Fab, an Fab', and an F(ab')2.

Functional antibody fragments comprising whole or essentially whole variable regions of both light and heavy chains are defined as follows:

(i) Fv, defined as a genetically engineered fragment consisting of the variable region of the light chain and the variable region of the heavy chain expressed as two chains;

(ii) single-chain Fv ("scFv"), a genetically engineered single-chain molecule including the variable region of the light chain and the variable region of the heavy chain, linked by a suitable polypeptide linker.

(iii) Fab, a fragment of an antibody molecule containing a monovalent antigen-binding portion of an antibody molecule, obtained by treating whole antibody with the enzyme papain to yield the intact light chain and the Fd fragment of the heavy chain, which consists of the variable and CH1 domains thereof;

(iv) Fab', a fragment of an antibody molecule containing a monovalent antigen-binding portion of an antibody molecule, obtained by treating whole antibody with the enzyme pepsin, followed by reduction (two Fab' fragments are obtained per antibody molecule); and (v) F(ab')2, a fragment of an antibody molecule containing a monovalent antigen-binding portion of an antibody molecule, obtained by treating whole antibody with the enzyme pepsin (i.e., a dimer of Fab' fragments held together by two disulfide bonds).

Methods of generating monoclonal and polyclonal antibodies are well known in the art. Antibodies may be generated via any one of several known methods, which may employ induction of in vivo production of antibody molecules, screening of immunoglobulin libraries (Orlandi, R. et al. (1989). Cloning immunoglobulin variable domains for expression by the polymerase chain reaction. Proc Natl Acad Sci USA 86, 3833-3837; and Winter, G. and Milstein, C. (1991). Man-made antibodies. Nature 349, 293-299), or generation of monoclonal antibody molecules by continuous cell lines in culture. These include, but are not limited to, the hybridoma technique, the human B-cell hybridoma technique, and the Epstein-Barr virus (EBV)-hybridoma technique (Kohler, G. and Milstein, C. (1975). Continuous cultures of fused cells secreting antibody of predefined specificity. Nature 256, 495-497; Kozbor, D. et al. (1985). Specific immunoglobulin production and enhanced tumorigenicity following ascites growth of human hybridomas. J Immunol Methods 81, 31-42; Cote R J. et al. (1983). Generation of human monoclonal antibodies reactive with cellular antigens. Proc Natl Acad Sci USA 80, 2026-2030; and Cole, S. P. et al. (1984). Human monoclonal antibodies. Mol Cell Biol 62, 109-120).

In cases where target antigens are too small to elicit an adequate immunogenic response when generating antibodies in vivo, such antigens (referred to as "haptens") can be coupled to antigenically neutral carriers such as keyhole limpet hemocyanin (KLH) or serum albumin (e.g., bovine serum albumin (BSA)) carriers (see, for example, U.S. Pat. Nos. 5,189,178 and 5,239,078). Coupling a hapten to a carrier can be effected using methods well known in the art. For example, direct coupling to amino groups can be effected and optionally followed by reduction of the imino linkage formed. Alternatively, the carrier can be coupled using condensing agents such as dicyclohexyl carbodiimide or other carbodiimide dehydrating agents. Linker compounds can also be used to effect the coupling; both homobifunctional and heterobifunctional linkers are available from Pierce Chemical Company, Rockford, Ill., USA. The resulting immunogenic complex can then be injected into suitable mammalian subjects such as mice, rabbits, and others. Suitable protocols involve repeated injection of the immunogen in the presence of adjuvants according to a schedule designed to boost production of antibodies in the serum. The titers of the immune serum can readily be measured using immunoassay procedures which are well known in the art.

The antisera obtained can be used directly or monoclonal antibodies may be obtained, as described hereinabove.

Antibody fragments may be obtained using methods well known in the art. (See, for example, Harlow, E. and Lane, D. (1988). Antibodies: A Laboratory Manual, Cold Spring Harbor Laboratory, New York.) For example, antibody fragments according to the present invention can be prepared by proteolytic hydrolysis of the antibody or by expression in E. coli or mammalian cells (e.g., Chinese hamster ovary (CHO) cell culture or other protein expression systems) of DNA encoding the fragment.

Alternatively, antibody fragments can be obtained by pepsin or papain digestion of whole antibodies by conventional methods. As described hereinabove, an (Fab')$_2$ antibody fragments can be produced by enzymatic cleavage of antibodies with pepsin to provide a 5S fragment. This fragment can be further cleaved using a thiol reducing agent, and optionally a blocking group for the sulfhydryl groups resulting from cleavage of disulfide linkages, to produce 3.5S Fab' monovalent fragments. Alternatively, enzymatic cleavage using pepsin produces two monovalent Fab' fragments and an Fc fragment directly. Ample guidance for practicing such methods is provided in the literature of the art (for example, refer to: U.S. Pat. Nos. 4,036,945 and 4,331,647; and Porter, R. R. (1959). The hydrolysis of rabbit γ-globulin and antibodies with crystalline papain. Biochem J 73, 119-126). Other methods of cleaving antibodies, such as separation of heavy chains to form monovalent light-heavy chain fragments, further cleavage of fragments, or other enzymatic, chemical, or genetic techniques may also be used, so long as the fragments retain the ability to bind to the antigen that is recognized by the intact antibody.

As described hereinabove, an Fv is composed of paired heavy chain variable and light chain variable domains. This association may be noncovalent (see, for example, Inbar, D. et al. (1972). Localization of antibody-combining sites within the variable portions of heavy and light chains. Proc Natl Acad Sci USA 69, 2659-2662). Alternatively, as described hereinabove, the variable domains may be linked to generate a single-chain Fv by an intermolecular disulfide bond, or alternately such chains may be cross-linked by chemicals such as glutaraldehyde.

Preferably, the Fv is a single-chain Fv. Single-chain Fvs are prepared by constructing a structural gene comprising DNA sequences encoding the heavy chain variable and light chain variable domains connected by an oligonucleotide encoding a peptide linker. The structural gene is inserted into an expression vector, which is subsequently introduced into a host cell such as E. coli. The recombinant host cells synthesize a single polypeptide chain with a linker peptide bridging the two variable domains. Ample guidance for producing single-chain Fvs is provided in the literature of the art (see, e.g.: Whitlow, M. and Filpula, D. (1991). Single-chain Fv proteins and their fusion proteins. METHODS: A Companion to Methods in Enzymology 2(2), 97-105; Bird, R. E. et al. (1988). Single-chain antigen-binding proteins. Science 242, 423-426; Pack, P. et al. (1993). Improved bivalent miniantibodies, with identical avidity as whole antibodies, produced by high cell density fermentation of Escherichia coli. Biotechnology (N. Y.) 11(11), 1271-1277; and U.S. Pat. No. 4,946,778).

Isolated complementarity-determining region peptides can be obtained by constructing genes encoding the CDR of an antibody of interest. Such genes may be prepared, for example, by RT-PCR of the mRNA of an antibody-producing cell. Ample guidance for practicing such methods is provided in the literature of the art (e.g., Larrick, J. W. and Fry, K. E. (1991). PCR Amplification of Antibody Genes. METHODS: A Companion to Methods in Enzymology 2(2), 106-110).

It will be appreciated that for human therapy or diagnostics, humanized antibodies are preferably used. Humanized forms of non-human (e.g., murine) antibodies are genetically engineered chimeric antibodies or antibody fragments having (preferably minimal) portions derived from non-human antibodies. Humanized antibodies include antibodies in which the CDRs of a human antibody (recipient antibody) are replaced by residues from a CDR of a non-human species (donor antibody), such as mouse, rat, or rabbit, having the desired functionality. In some instances, the Fv framework residues of the human antibody are replaced by corresponding non-human residues. Humanized antibodies may also comprise residues found neither in the recipient antibody nor in the imported CDR or framework sequences. In general, the humanized antibody will comprise substantially all of at least one, and typically two, variable domains, in which all or substantially all of the CDRs correspond to those of a non-human antibody and all or substantially all of the framework regions correspond to those of a relevant human consensus sequence. Humanized antibodies optimally also include at least a portion of an antibody constant region, such as an Fc region, typically derived from a human antibody (see, for example: Jones, P. T. et al. (1986). Replacing the complementarity-determining regions in a human antibody with those from a mouse. Nature 321, 522-525; Riechmann, L. et al. (1988). Reshaping human antibodies for therapy. Nature 332, 323-327; Presta, L. G. (1992b). Curr Opin Struct Biol 2, 593-596; and Presta, L. G. (1992a). Antibody engineering. Curr Opin Biotechnol 3(4), 394-398).

Methods for humanizing non-human antibodies are well known in the art. Generally, a humanized antibody has one or more amino acid residues introduced into it from a source which is non-human. These non-human amino acid residues are often referred to as imported residues, which are typically taken from an imported variable domain. Humanization can be performed essentially as described (see, for example: Jones et al. (1986); Riechmann et al. (1988); Verhoeyen, M. et al. (1988). Reshaping human antibodies: grafting an antilysozyme activity. Science 239, 1534-1536; and U.S. Pat. No. 4,816,567), by substituting human CDRs with corresponding rodent CDRs. Accordingly, humanized antibodies are chimeric antibodies, wherein substantially less than an intact human variable domain has been substituted by the corresponding sequence from a non-human species. In practice, humanized antibodies may be typically human antibodies in which some CDR residues and possibly some framework residues are substituted by residues from analogous sites in rodent antibodies.

Human antibodies can also be produced using various additional techniques known in the art, including phage-display libraries (Hoogenboom, H. R. and Winter, G. (1991). By-passing immunisation. Human antibodies from synthetic repertoires of germline VH gene segments rearranged in vitro. J Mol Biol 227, 381-388; Marks, J. D. et al. (1991). By-passing immunization. Human antibodies from V-gene libraries displayed on phage. J Mol Biol 222, 581-597; Cole et al. (1985), Monoclonal Antibodies and Cancer Therapy, Alan R. Liss, Inc., pp. 77-96; and Boerner, P. et al. (1991). Production of antigen-specific human monoclonal antibodies from in vitro-primed human splenocytes. J Immunol 147, 86-95). Humanized antibodies can also be created by introducing sequences encoding human immunoglobulin loci into transgenic animals, e.g., into mice in which the endogenous immunoglobulin genes have been partially or completely inactivated. Upon antigenic challenge, human antibody production is observed in such animals which closely resembles that seen in humans in all respects, including gene rearrangement, chain assembly, and antibody repertoire. Ample guidance for practicing such an approach is provided in the literature of the art (for example, refer to: U.S. Pat. Nos. 5,545,807; 5,545,806; 5,569,825; 5,625,126; 5,633,425; and 5,661,016; Marks, J. D. et al. (1992). By-passing immunization: building high affinity human antibodies by chain shuffling. Biotechnology (N.Y.) 10(7), 779-783; Lonberg et al., 1994. Nature 368:856-859; Morrison, S. L. (1994). News and View: Success in Specification. Nature 368, 812-813; Fishwild, D. M. et al. (1996). High-avidity human IgG kappa monoclonal antibodies from a novel strain of minilocus transgenic mice. Nat Biotechnol 14, 845-851; Neuberger, M. (1996). Generating high-avidity human Mabs in mice. Nat Biotechnol 14, 826; and Lonberg, N. and Huszar, D. (1995). Human antibodies from transgenic mice. Int Rev Immunol 13, 65-93).

After antibodies have been obtained, they may be tested for activity, for example via enzyme-linked immunosorbent assay (ELISA).

According to other preferred embodiments of the present invention, there is provided a system and method for producing functional IgG4 antibodies in plant cell culture, preferably root plant cell culture that is optionally and more preferably grown in suspension. Optionally and most preferably, the plant cell culture comprises carrot root cells.

According to still other preferred embodiments of the present invention, there is provided a system and method for producing antibodies in plant cell culture, preferably root plant cell culture that is optionally and more preferably grown in suspension, in which the antibodies have a greater binding affinity for a target antigen than corresponding antibodies grown in mammalian cell culture.

According to still other preferred embodiments of the present invention, there is provided an antibody having a heavy chain and a light chain sequence being at least about 80%, preferably at least about 85%, more preferably at least about 90% and most preferably at least about 95% homologous to SEQ ID NOs: 1 and 5, respectively. Optionally, there is provided an antibody having a sequence consisting essentially of sequences according to SEQ ID NOs: 1 and 5. This antibody is of an IgG1 subtype.

According to yet other preferred embodiments of the present invention, there is provided an antibody having a heavy chain and a light chain sequence being at least about 80%, preferably at least about 85%, more preferably at least about 90% and most preferably at least about 95% homologous to a sequence selected from the group consisting of Genes 1-4 (heavy chain; SEQ ID NOs: 1-4) and to a sequence selected from the group consisting of Genes 9-12 (light chain; SEQ ID NOs: 5-8), respectively. Optionally, there is provided an antibody having a heavy chain sequence selected from the group consisting of Genes 1-4 (heavy chain; SEQ ID NOs: 1-4) and a light chain sequence selected from the group consisting of Genes 9-12 (light chain; SEQ ID NOs: 5-8). This antibody is of an IgG1 subtype. According to yet other preferred embodiments of the present invention, there is provided an antibody having a heavy chain and a light chain sequence being at least about 80%, preferably at least about 85%, more preferably at least about 90% and most preferably at least about 95% homologous to a sequence selected from the group consisting of Genes 5-8 (heavy chain; SEQ ID NOs: 9-12) and to a sequence selected from the group consisting of Genes 9-12 (light chain; SEQ ID NOs: 5-8), respectively. Optionally, there is provided an antibody having a heavy chain sequence selected from the group consisting of Genes 5-8 (heavy chain; SEQ ID NOs: 9-12) and a light chain sequence selected from the group consisting of Genes 9-12 (light chain; SEQ ID NOs: 5-8). This antibody is of an IgG4 subtype.

According to still other embodiments of the present invention, there is provided an antibody comprising a plant signal peptide. Preferably, the antibody is of an IgG4 subtype. Optionally and preferably, the plant signal peptide targets the antibody to an organelle selected from the group consisting of Apo (apoplast), ER (endoplasmic reticulum) and vacuole. More preferably, the plant signal peptide targets the antibody to the ER, such that the antibody is optionally and most preferably retained by the ER and does not pass to the Golgi body. Optionally the stop codon is not present in the antibody sequence to facilitate fusion with the ER retention signal. Also optionally, targeting to the vacuole is achieved by incorporating a sequence coding for the vacuolar sorting signal GLLVDTM (seq id no: 13) before the stop codon.

As used herein the term "plant" refers to any plant such as a moocot or dicot plant as well as to other plants such as coniferous plants, moss or algae, which are capable of being genetically modified. According to presently known embodiment the plant is a carrot plant. According to another embodiment, the plant is of the genus *Nicotiana*, which comprises without limitation, *Nicotiana alata*, *Nicotiana glauca* (Wild Tobacco), *Nicotiana langsdorffli*, *Nicotiana longiflora*, *Nicotiana sylvestris*, *Nicotiana tabacum* (Tobacco).

"Cells", "host cells" or "recombinant host cells" are terms used interchangeably herein. It is understood that such terms refer not only to the particular subject cells but to the progeny or potential progeny of such a cell. Because certain modifications may occur in succeeding generation due to either mutation or environmental influences, such progeny may not, in fact, be identical to the parent cell, but are still included within the scope of the term as used herein. "Host cell" as used herein refers to cells which can be recombinantly transformed with naked DNA or expression vectors constructed using recombinant DNA techniques. As used herein, the term "transfection" means the introduction of a nucleic acid, e.g., naked DNA or an expression vector, into a recipient cells by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of the desired protein.

It should be appreciated that a drug resistance or other selectable marker is intended in part to facilitate the selection of the transformants. Additionally, the presence of a selectable marker, such as drug resistance marker may be of use in keeping contaminating microorganisms from multiplying in the culture medium. Such a pure culture of the transformed host cell would be obtained by culturing the cells under conditions which are required for the induced phenotype's survival.

As indicated above, the host cells of the invention may be transfected or transformed with a nucleic acid molecule. As used herein, the term "nucleic acid" refers to polynucleotides such as deoxyribonucleic acid (DNA), and, where appropriate, ribonucleic acid (RNA). The terms should also be understood to include, as equivalents, analogs of either RNA or DNA made from nucleotide analogs, and, as applicable to the embodiment being described, single-stranded (such as sense or antisense) and double-stranded polynucleotides.

In yet another embodiment, the host cell of the invention may be transfected or transformed with an expression vector comprising the recombinant nucleic acid molecule. "Expression Vectors", as used herein, encompass vectors such as plasmids, viruses, bacteriophage, integratable DNA fragments, and other vehicles, which enable the integration of DNA fragments into the genome of the host. Expression vectors are typically self-replicating DNA or RNA constructs containing the desired gene or its fragments, and operably linked genetic control elements that are recognized in a suitable host cell and effect expression of the desired genes. These control elements are capable of effecting expression within a suitable host. Generally, the genetic control elements can include a prokaryotic promoter system or a eukaryotic promoter expression control system. Such system typically includes a transcriptional promoter, an optional operator to control the onset of transcription, transcription enhancers to elevate the level of RNA expression, a sequence that encodes a suitable ribosome binding site, RNA splice junctions, sequences that terminate transcription and translation and so forth. Expression vectors usually contain an origin of replication that allows the vector to replicate independently of the host cell.

Plasmids are the most commonly used form of vector but other forms of vectors which serves an equivalent function and which are, or become, known in the art are suitable for use herein. See, e.g., Pouwels et al. Cloning Vectors: a Laboratory Manual (1985 and supplements), Elsevier, N. Y.; and Rodriquez, et al. (eds.) Vectors: a Survey of Molecular Cloning Vectors and their Uses, Buttersworth, Boston, Mass. (1988), which are incorporated herein by reference.

In general, such vectors contain, in addition, specific genes which are capable of providing phenotypic selection in transformed cells. The use of prokaryotic and eukaryotic viral expression vectors to express the genes coding for the polypeptides of the present invention are also contemplated.

Optionally, the vector may be a general plant vector (as described with regard to the Examples below). Alternatively, the vector may optionally be specific for root cells.

In one preferred embodiment, the host cell of the invention may be a eukaryotic or prokaryotic cell.

In a specific embodiment, the host cell of the invention is a prokaryotic cell, preferably, a bacterial cell, most preferably, an *Agrobacterium tumefaciens* cell. These cells are used for infecting the preferred plant host cells described below.

In another preferred embodiment, the host cell of the invention may be an eukaryotic cell, preferably, a plant cell (e.g., root cells, leaf cells, stem cells, petiols cells, meristem cells and fruit cells (e.g., grapes). According to a preferred embodiment the plant root cell is selected from the group consisting of *Agrobacterium rihzogenes* transformed plant root cell, celery cell, ginger cell, horseradish cell and carrot cell.

In a preferred embodiment, the plant root cell is a carrot cell. It should be noted that the transformed carrot cells of the invention are grown in suspension. As mentioned above and described in the Examples, these cells were transformed with the *Agrobacterium tumefaciens* cells of the invention.

As mentioned, the nucleic acid constructs of the present invention (plasmid, described hereinabove) can be utilized to stably or transiently transform plant cells. In stable transformation, the nucleic acid molecule of the present invention is integrated into the plant genome, and as such it represents a stable and inherited trait. In transient transformation, the nucleic acid molecule is expressed by the cell transformed but not integrated into the genome, and as such represents a transient trait.

There are various methods of introducing foreign genes into both monocotyledonous and dicotyledonous plants (Potrykus, I. (1991). Annu Rev Plant Physiol Plant Mol Biol 42, 205-225; Shimamoto, K. et al. (1989). Fertile transgenic rice plants regenerated from transformed protoplasts. Nature (1989) 338, 274-276).

The principal methods of the stable integration of exogenous DNA into plant genomic DNA include two main approaches:

(i) *Agrobacterium*-mediated gene transfer. See: Klee, H. J. et al. (1987). Annu Rev Plant Physiol 38, 467-486; Klee, H. J. and Rogers, S. G. (1989). Cell Culture and Somatic Cell Genetics of Plants, Vol. 6, Molecular Biology of Plant Nuclear Genes, pp. 2-25, J. Schell and L. K. Vasil, eds., Academic Publishers, San Diego, Calif.; and Gatenby, A. A. (1989). Regulation and Expression of Plant Genes in Microorganisms, pp. 93-112, Plant Biotechnology, S. Kung and C. J. Arntzen, eds., Butterworth Publishers, Boston, Mass.

(ii) Direct DNA uptake. See, e.g.: Paszkowski, J. et al. (1989). Cell Culture and Somatic Cell Genetics of Plants, Vol. 6, Molecular Biology of Plant Nuclear Genes, pp. 52-68, J. Schell and L. K. Vasil, eds., Academic Publishers, San Diego, Cal.; and Toriyama, K. et al. (1988). Bio/Technol 6, 1072-1074 (methods for direct uptake of DNA into protoplasts). See also: Zhang et al. (1988). Plant Cell Rep 7, 379-384; and Fromm, M. E. et al. (1986). Stable transformation of maize after gene transfer by electroporation. Nature 319, 791-793 (DNA uptake induced by brief electric shock of plant cells). See also: Klein et al. (1988). Bio/Technology 6, 559-563; McCabe, D. E. et al. (1988). Stable transformation of soybean (*Glycine max*) by particle acceleration. Bio/Technology 6, 923-926; and Sanford, J. C. (1990). Biolistic plant transformation. Physiol Plant 79, 206-209 (DNA injection into plant cells or tissues by particle bombardment). See also: Neuhaus, J. M. et al. (1987). Theor Appl Genet. 75, 30-36; and Neuhaus, J. M. and Spangenberg, G. C. (1990). Physiol Plant 79, 213-217 (use of micropipette systems). See U.S. Pat. No. 5,464,765 (glass fibers or silicon carbide whisker transformation of cell cultures, embryos or callus tissue). See also: DeWet, J. M. J. et al. (1985). "Exogenous gene transfer in maize (*Zea mays*) using DNA-treated pollen," Experimental Manipulation of Ovule Tissue, G. P. Chapman et al., eds., Longman, New York-London, pp. 197-209; and Ohta, Y. (1986). High-Efficiency Genetic Transformation of Maize by a Mixture of Pollen and Exogenous DNA. Proc Natl Acad Sci USA 83, 715-719 (direct incubation of DNA with germinating pollen).

The *Agrobacterium*-mediated system includes the use of plasmid vectors that contain defined DNA segments which integrate into the plant genomic DNA. Methods of inoculation of the plant tissue vary depending upon the plant species and the *Agrobacterium* delivery system. A widely used approach is the leaf-disc procedure, which can be performed with any tissue explant that provides a good source for initiation of whole-plant differentiation (Horsch, R. B. et al. (1988). "Leaf disc transformation." Plant Molecular Biology Manual A5, 1-9, Kluwer Academic Publishers, Dordrecht). A supplementary approach employs the *Agrobacterium* delivery system in combination with vacuum infiltration. The *Agrobacterium* system is especially useful for in the creation of transgenic dicotyledenous plants.

There are various methods of direct DNA transfer into plant cells. In electroporation, the protoplasts are briefly exposed to a strong electric field, opening up mini-pores to allow DNA to enter. In microinjection, the DNA is mechanically injected directly into the cells using micropipettes. In microparticle bombardment, the DNA is adsorbed on microprojectiles such as magnesium sulfate crystals or tungsten particles, and the microprojectiles are physically accelerated into cells or plant tissues.

Following stable transformation, plant propagation then occurs. The most common method of plant propagation is by seed. The disadvantage of regeneration by seed propagation, however, is the lack of uniformity in the crop due to heterozygosity, since seeds are produced by plants according to the genetic variances governed by Mendelian rules. In other words, each seed is genetically different and each will grow with its own specific traits. Therefore, it is preferred that the regeneration be effected such that the regenerated plant has identical traits and characteristics to those of the parent transgenic plant. The preferred method of regenerating a transformed plant is by micropropagation, which provides a rapid, consistent reproduction of the transformed plants.

Micropropagation is a process of growing second-generation plants from a single tissue sample excised from a selected parent plant or cultivar. This process permits the mass reproduction of plants having the preferred tissue and expressing a fusion protein. The newly generated plants are genetically identical to, and have all of the characteristics of, the original plant. Micropropagation allows for mass production of quality plant material in a short period of time and offers a rapid multiplication of selected cultivars with preservation of the characteristics of the original transgenic or transformed plant. The advantages of this method of plant cloning include the speed of plant multiplication and the quality and uniformity of the plants produced.

Micropropagation is a multi-stage procedure that requires alteration of culture medium or growth conditions between stages. The micropropagation process involves four basic stages: stage one, initial tissue culturing; stage two, tissue culture multiplication; stage three, differentiation and plant formation; and stage four, greenhouse culturing and hardening. During stage one, the tissue culture is established and certified contaminant-free. During stage two, the initial tissue culture is multiplied until a sufficient number of tissue samples are produced to meet production goals. During stage three, the newly grown tissue samples are divided and grown into individual plantlets. At stage four, the transformed plantlets are transferred to a greenhouse for hardening where the plants' tolerance to light is gradually increased so that they can continue to grow in the natural environment.

According to presently known preferred embodiments of the present invention the recombinant protein may be produced by plant cells according to the present invention by culturing in a device described with regard to U.S. Pat. No. 6,391,638, issued on May 21, 2002 and hereby incorporated by reference as if fully set forth herein. Conditions for culturing plant cells in suspension with this device are described with regard to the US patent application entitled "CELL/TISSUE CULTURING DEVICE, SYSTEM AND METHOD" by one of the present inventors and owned in common with the present application, which is hereby incorporated by reference as if fully set forth herein.

Although stable transformation is presently preferred, transient transformation of, for instance, leaf cells, meristematic cells, or the whole plant is also envisaged by the present invention.

Transient transformation can be effected by any of the direct DNA transfer methods described above or by viral infection using modified plant viruses.

Viruses that have been shown to be useful for the transformation of plant hosts include cauliflower mosaic virus (CaMV), tobacco mosaic virus (TMV), and baculovirus (BV). Transformation of plants using plant viruses is described in, for example: U.S. Pat. No. 4,855,237 (bean golden mosaic virus, BGMV); EPA 67,553 (TMV); Japanese Published Application No. 63-14693 (TMV); EPA 194,809 (BV); EPA 278,667 (BV); and Gluzman, Y. et al. (1988). Communications in Molecular Biology: Viral Vectors, Cold Spring Harbor Laboratory, New York, pp. 172-189. The use of pseudovirus particles in expressing foreign DNA in many hosts, including plants, is described in WO 87/06261.

Construction of plant RNA viruses for the introduction and expression of non-viral exogenous nucleic acid sequences in plants is demonstrated by the above references as well as by: Dawson, W. O. et al. (1989). A tobacco mosaic virus-hybrid expresses and loses an added gene. Virology 172, 285-292; French, R. et al. (1986) Science 231, 1294-1297; and Takamatsu, N. et al. (1990). Production of enkephalin in tobacco protoplasts using tobacco mosaic virus RNA vector. FEBS Lett 269, 73-76.

If the transforming virus is a DNA virus, one skilled in the art may make suitable modifications to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of the DNA will produce the coat protein, which will encapsidate the viral DNA.

If the virus is an RNA virus, the virus is generally cloned as a cDNA and inserted into a plasmid. The plasmid is then used to make all of the plant genetic constructs. The RNA virus is then transcribed from the viral sequence of the plasmid, followed by translation of the viral genes to produce the coat proteins which encapsidate the viral RNA.

Construction of plant RNA viruses for the introduction and expression in plants of non-viral exogenous nucleic acid sequences, such as those included in the construct of the present invention, is demonstrated in the above references as well as in U.S. Pat. No. 5,316,931.

In one embodiment, there is provided for insertion a plant viral nucleic acid, comprising a deletion of the native coat protein coding sequence from the viral nucleic acid, a non-native (foreign) plant viral coat protein coding sequence, and a non-native promoter, preferably the subgenomic promoter of the non-native coat protein coding sequence, and capable of expression in the plant host, packaging of the recombinant plant viral nucleic acid, and ensuring a systemic infection of the host by the recombinant plant viral nucleic acid. Alternatively, the native coat protein coding sequence may be made non-transcribable by insertion of the non-native nucleic acid sequence within it, such that a non-native protein is produced. The recombinant plant viral nucleic acid construct may contain one or more additional non-native subgenomic promoters. Each non-native subgenomic promoter is capable of transcribing or expressing adjacent genes or nucleic acid sequences in the plant host and incapable of recombination with each other and with native subgenomic promoters. In addition, the recombinant plant viral nucleic acid construct may contain one or more cis-acting regulatory elements, such as enhancers, which bind a trans-acting regulator and regulate the transcription of a coding sequence located downstream thereto. Non-native nucleic acid sequences may be inserted adjacent to the native plant viral subgenomic promoter or the native and non-native plant viral subgenomic promoters if more than one nucleic acid sequence is included. The non-native nucleic acid sequences are transcribed or expressed in the host plant under control of the subgenomic promoter(s) to produce the desired products.

In a second embodiment, a recombinant plant viral nucleic acid construct is provided as in the first embodiment except that the native coat protein coding sequence is placed adjacent to one of the non-native coat protein subgenomic promoters instead of adjacent to a non-native coat protein coding sequence.

In a third embodiment, a recombinant plant viral nucleic acid construct is provided comprising a native coat protein gene placed adjacent to its subgenomic promoter and one or more non-native subgenomic promoters inserted into the viral nucleic acid construct. The inserted non-native subgenomic promoters are capable of transcribing or expressing adjacent genes in a plant host and are incapable of recombination with each other and with native subgenomic promoters. Non-native nucleic acid sequences may be inserted adjacent to the non-native subgenomic plant viral promoters such that said sequences are transcribed or expressed in the host plant under control of the subgenomic promoters to produce the desired product.

In a fourth embodiment, a recombinant plant viral nucleic acid construct is provided as in the third embodiment except that the native coat protein coding sequence is replaced by a non-native coat protein coding sequence.

Viral vectors are encapsidated by expressed coat proteins encoded by recombinant plant viral nucleic acid constructs as described hereinabove, to produce a recombinant plant virus. The recombinant plant viral nucleic acid construct or recombinant plant virus is used to infect appropriate host plants. The recombinant plant viral nucleic acid construct is capable of replication in a host, systemic spread within the host, and transcription or expression of one or more foreign genes (isolated nucleic acid) in the host to produce the desired protein.

In addition to the above, the nucleic acid molecule of the present invention can also be introduced into a chloroplast genome thereby enabling chloroplast expression.

A technique for introducing exogenous nucleic acid sequences to the genome of the chloroplasts is known. This technique involves the following procedures. First, plant cells are chemically treated so as to reduce the number of chloroplasts per cell to about one. Then, the exogenous nucleic acid is introduced into the cells preferably via particle bombardment, with the aim of introducing at least one exogenous nucleic acid molecule into the chloroplasts. The exogenous nucleic acid is selected by one ordinarily skilled in the art to be capable of integration into the chloroplast's genome via homologous recombination, which is readily effected by enzymes inherent to the chloroplast. To this end, the exogenous nucleic acid comprises, in addition to a gene of interest, at least one nucleic acid sequence derived from the chloroplast's genome. In addition, the exogenous nucleic acid comprises a selectable marker, which by sequential selection procedures serves to allow an artisan to ascertain that all or substantially all copies of the chloroplast genome following such selection include the exogenous nucleic acid. Further details relating to this technique are found in U.S. Pat. Nos. 4,945,050 and 5,693,507, which are incorporated herein by reference. A polypeptide can thus be produced by the protein expression system of the chloroplast and become integrated into the chloroplast's inner membrane.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The attached figures illustrate certain aspects of the invention but are not meant to be limiting in any way.

Figure 1A:
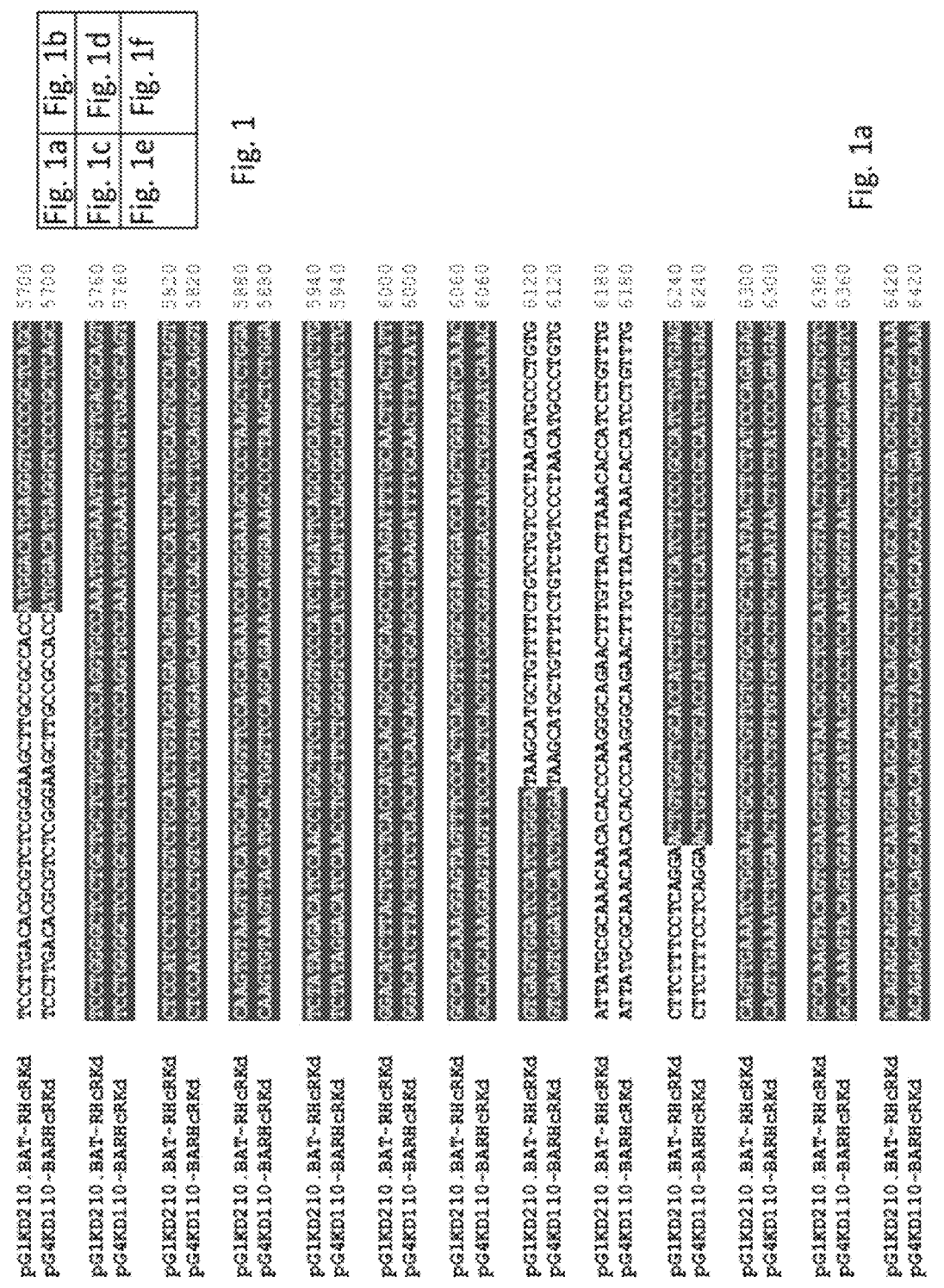
Figure 1B:
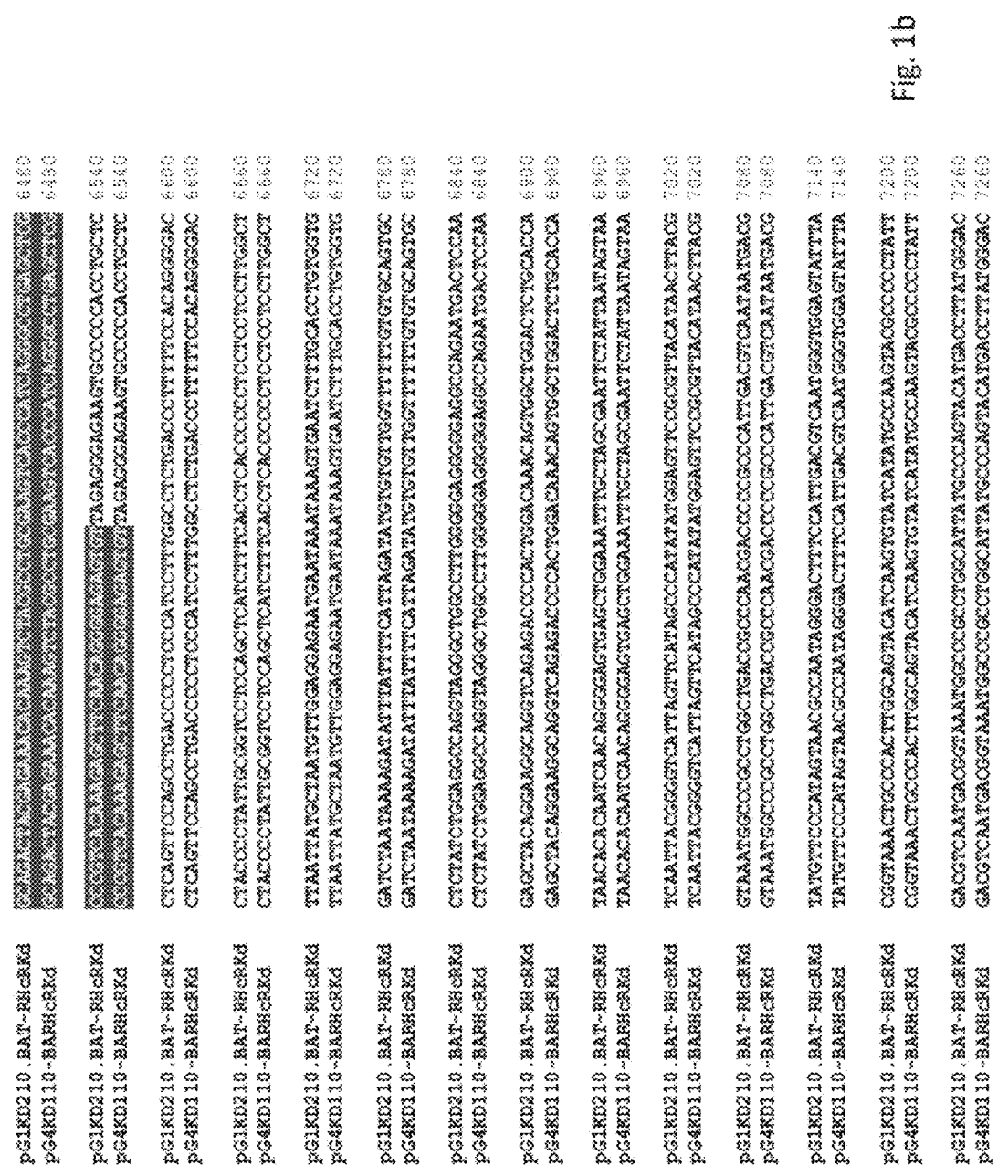
Figure 1C:
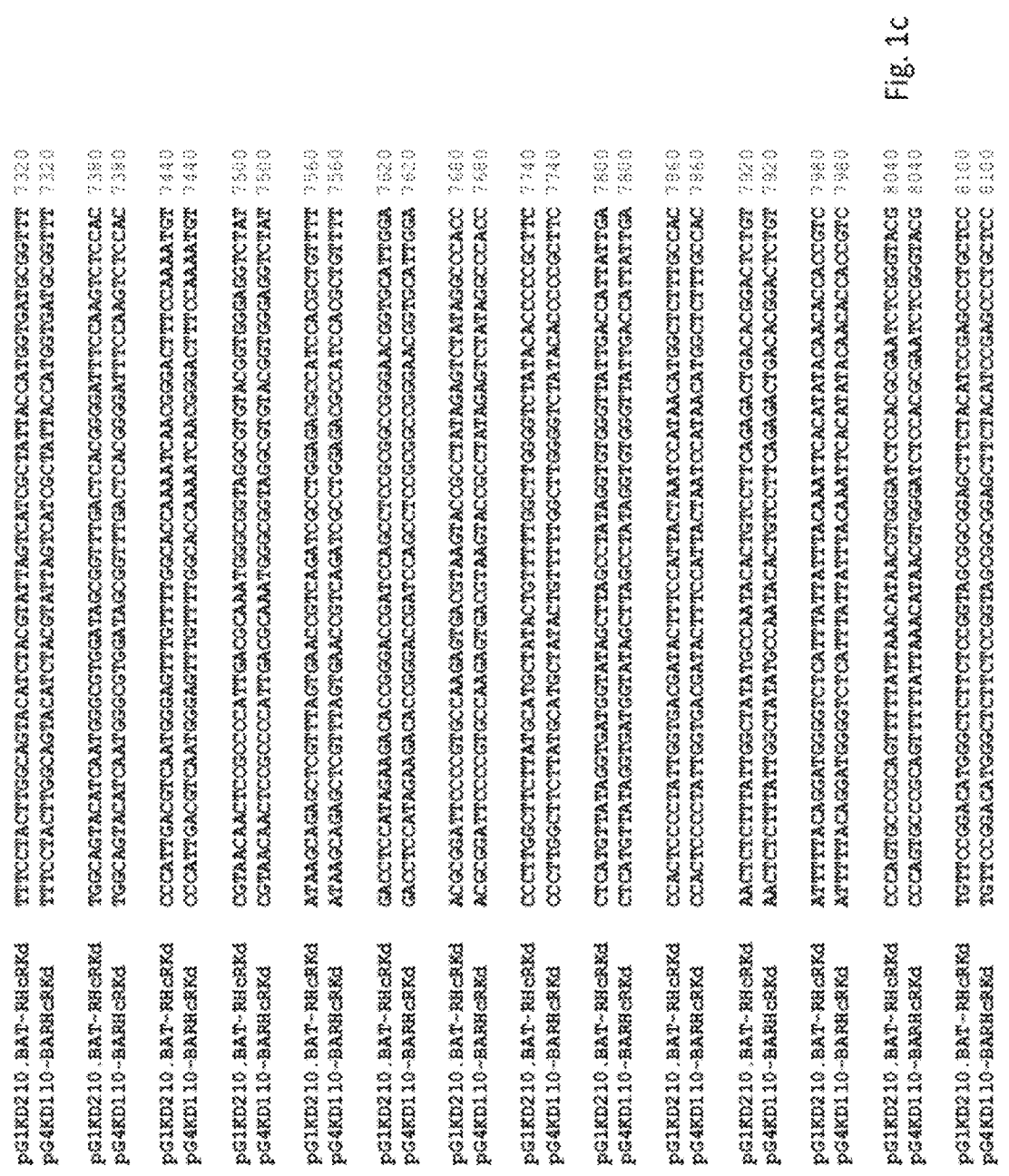
Figure 1D:
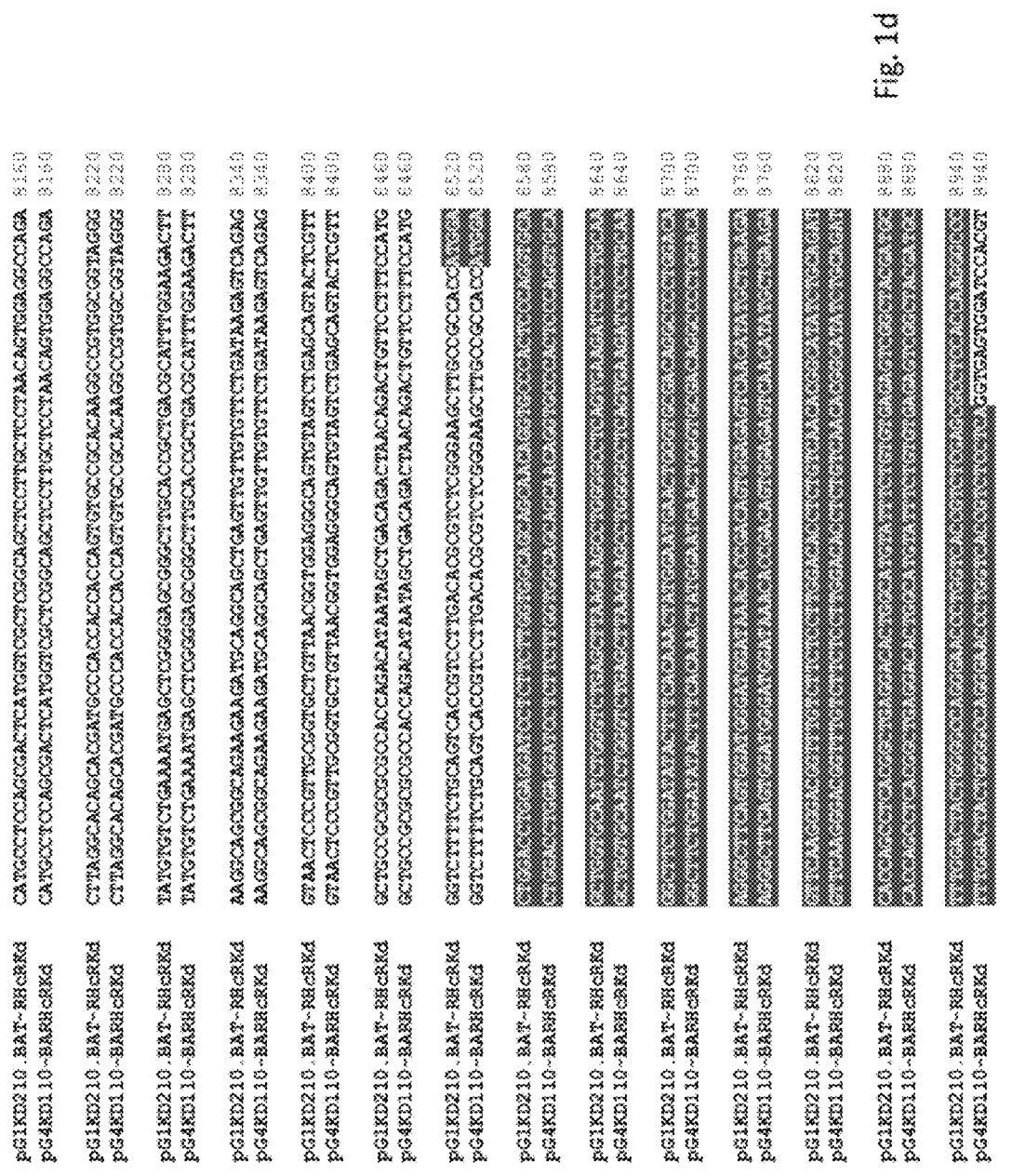
Figure 1E:
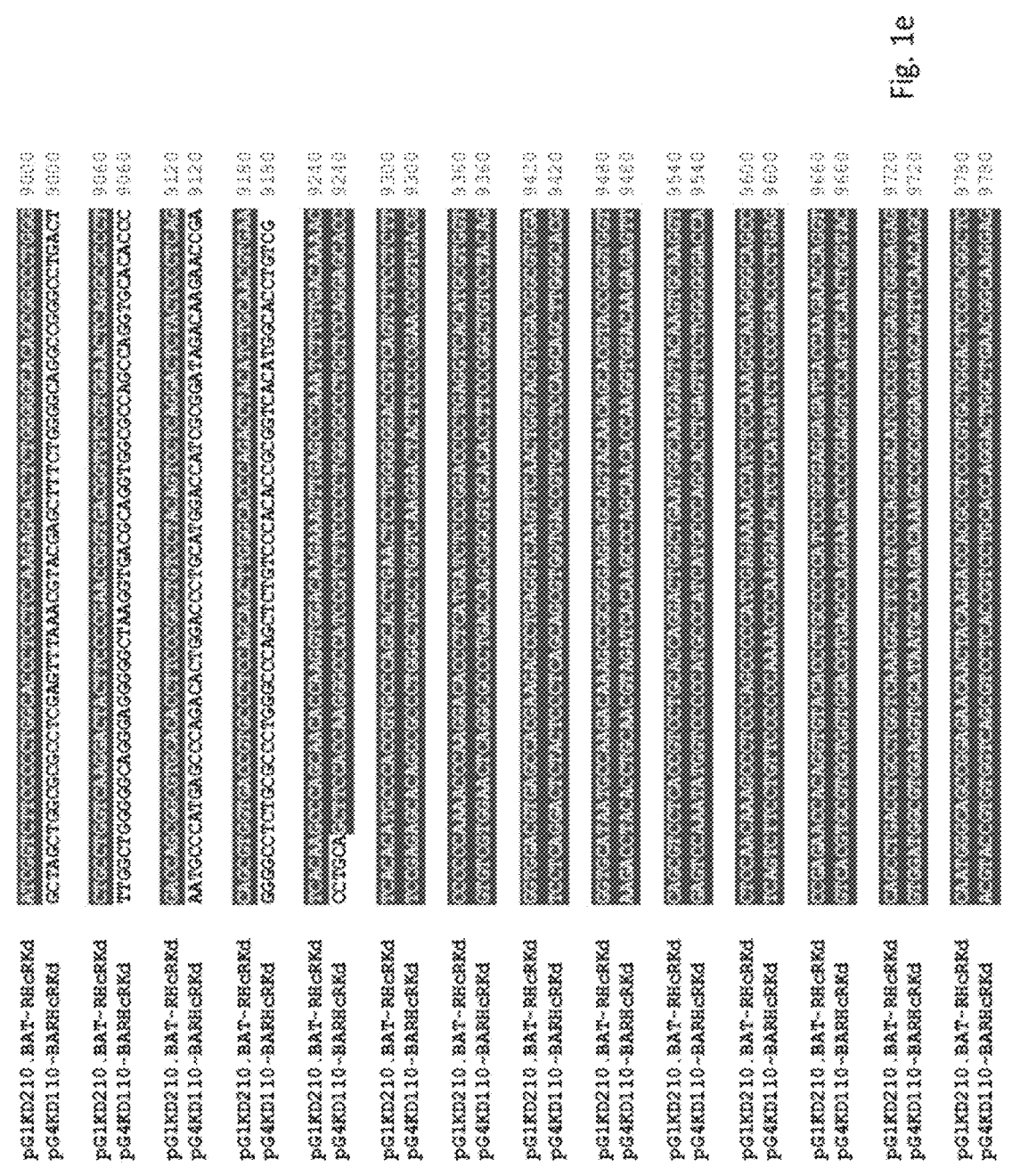
Figure 1F:
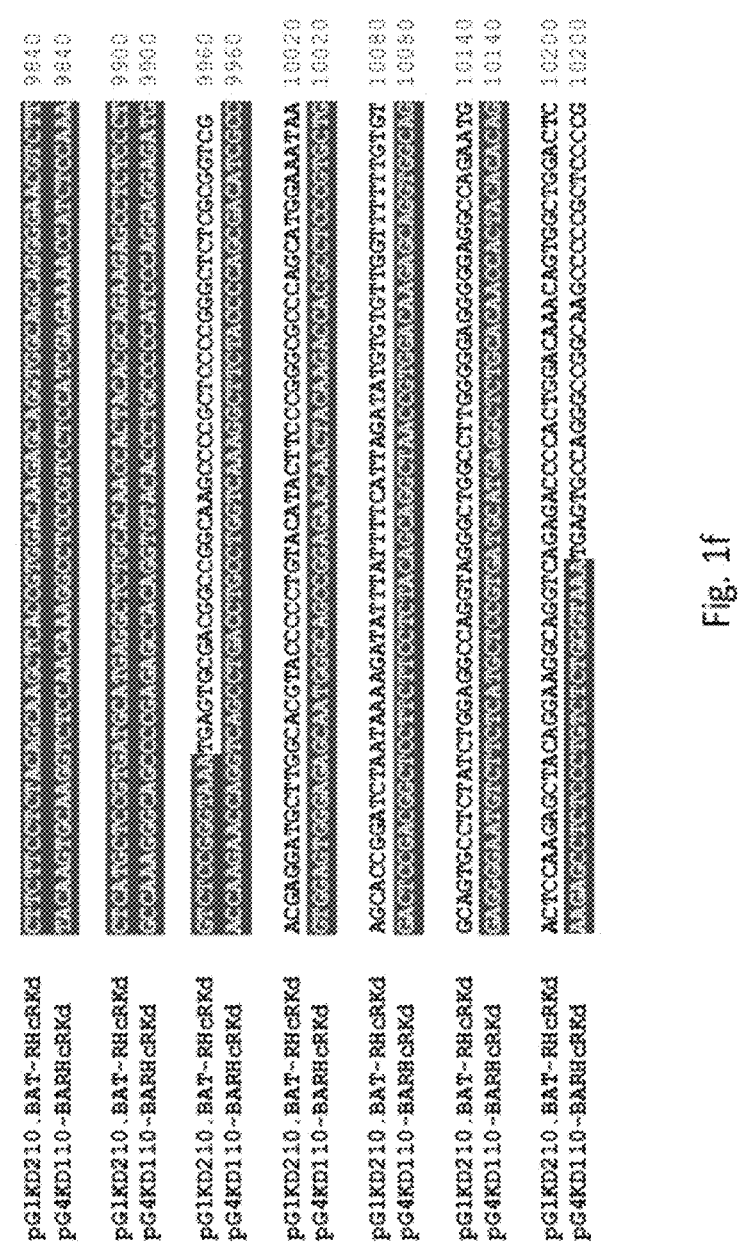

FIG. 1 shows the amino acid sequence of the illustrative antibody produced in the plant cell culture system according to the present invention, in the Super vector sequences; the exon sequences of both light and heavy chains are highlighted in red.

The sequences are as follows: pG1KD210.BAT-RHcRKd (SEQ ID NO: 15)-IgG1 heavy and light chains; and pG4KD110-BARHcRKd (SEQ ID NO: 16)-IgG4 heavy and light chains.

Figure 2B:
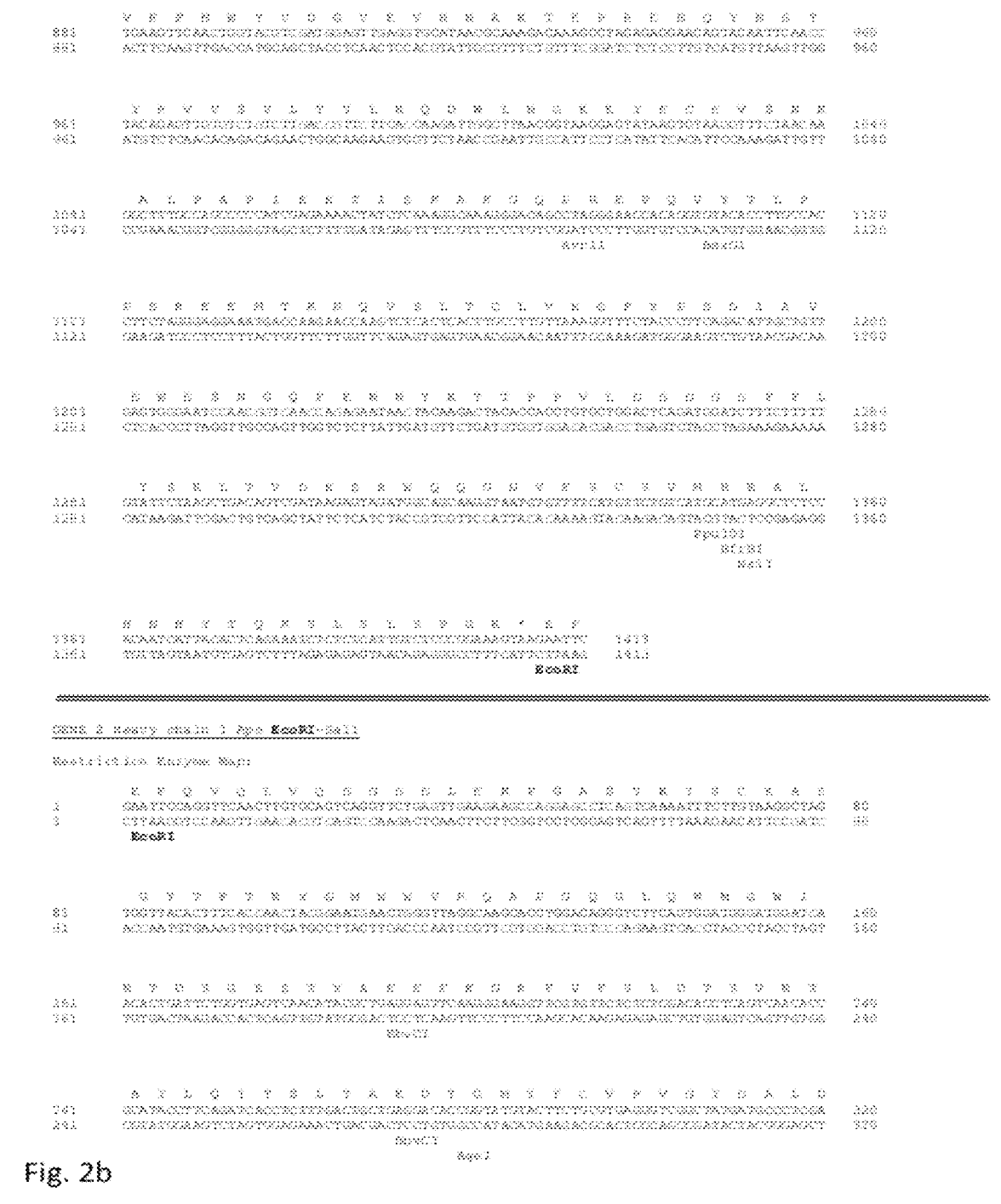
Figure 2C:
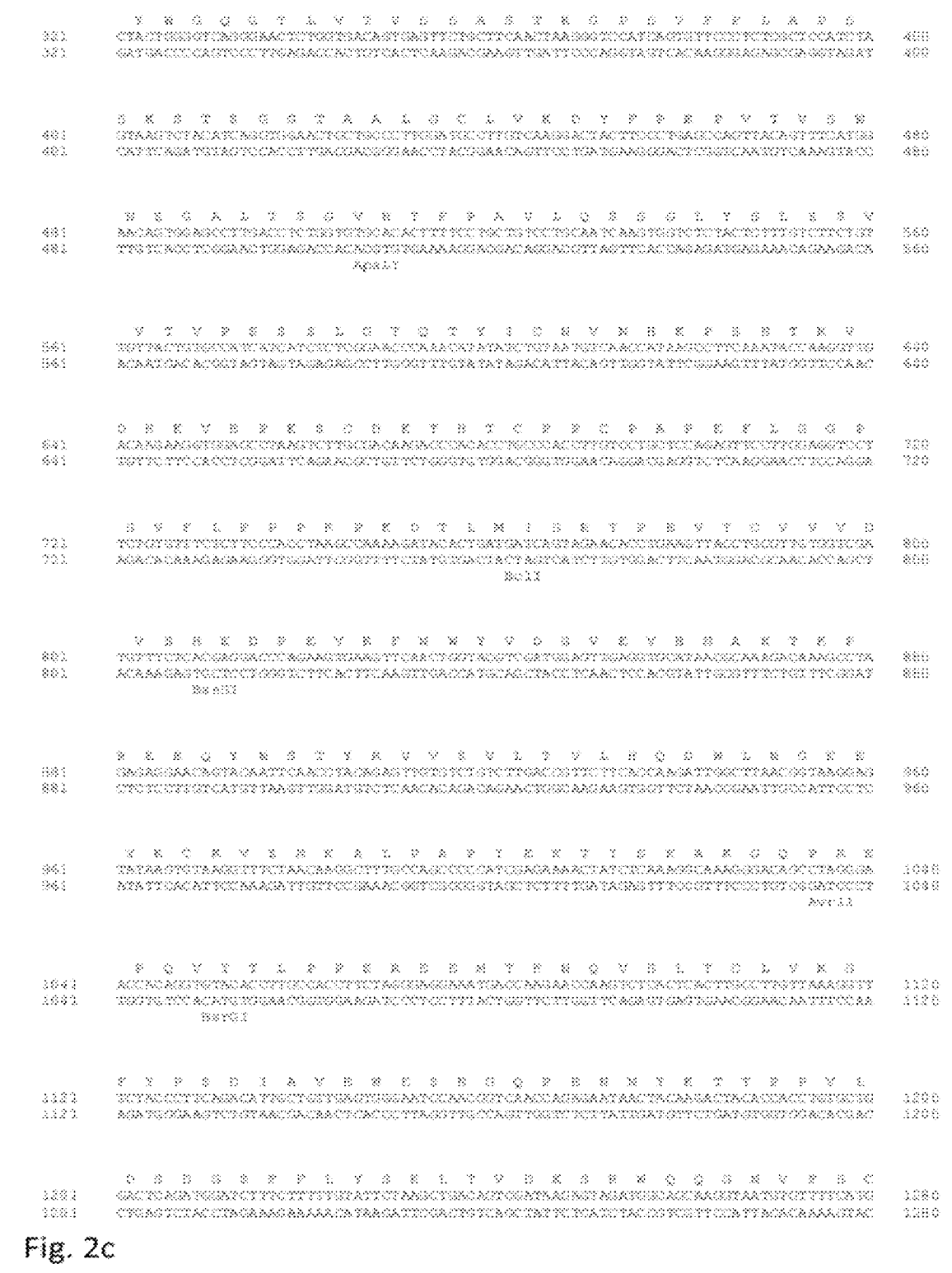
Figure 2D:
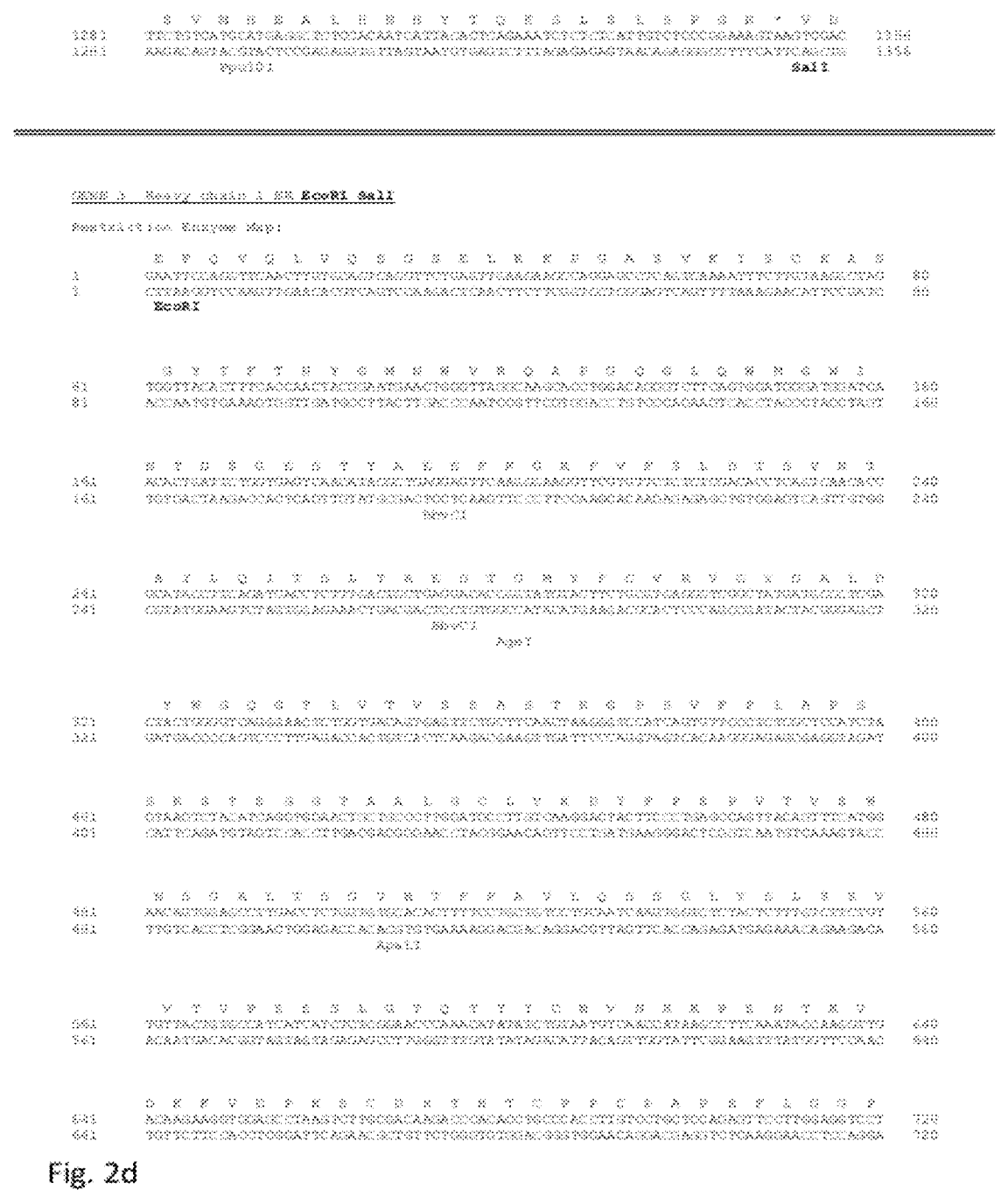
Figure 2E:
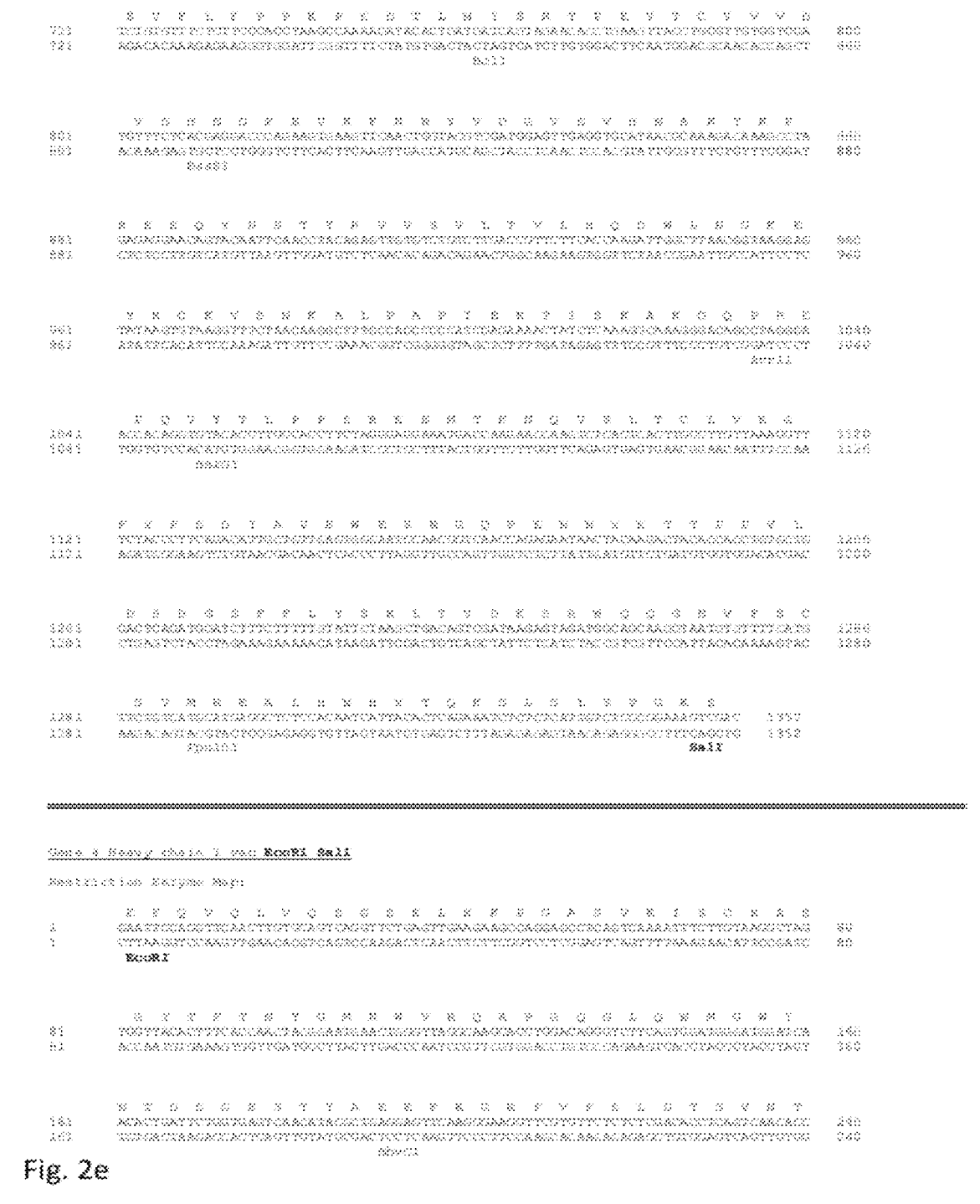
Figure 2F:
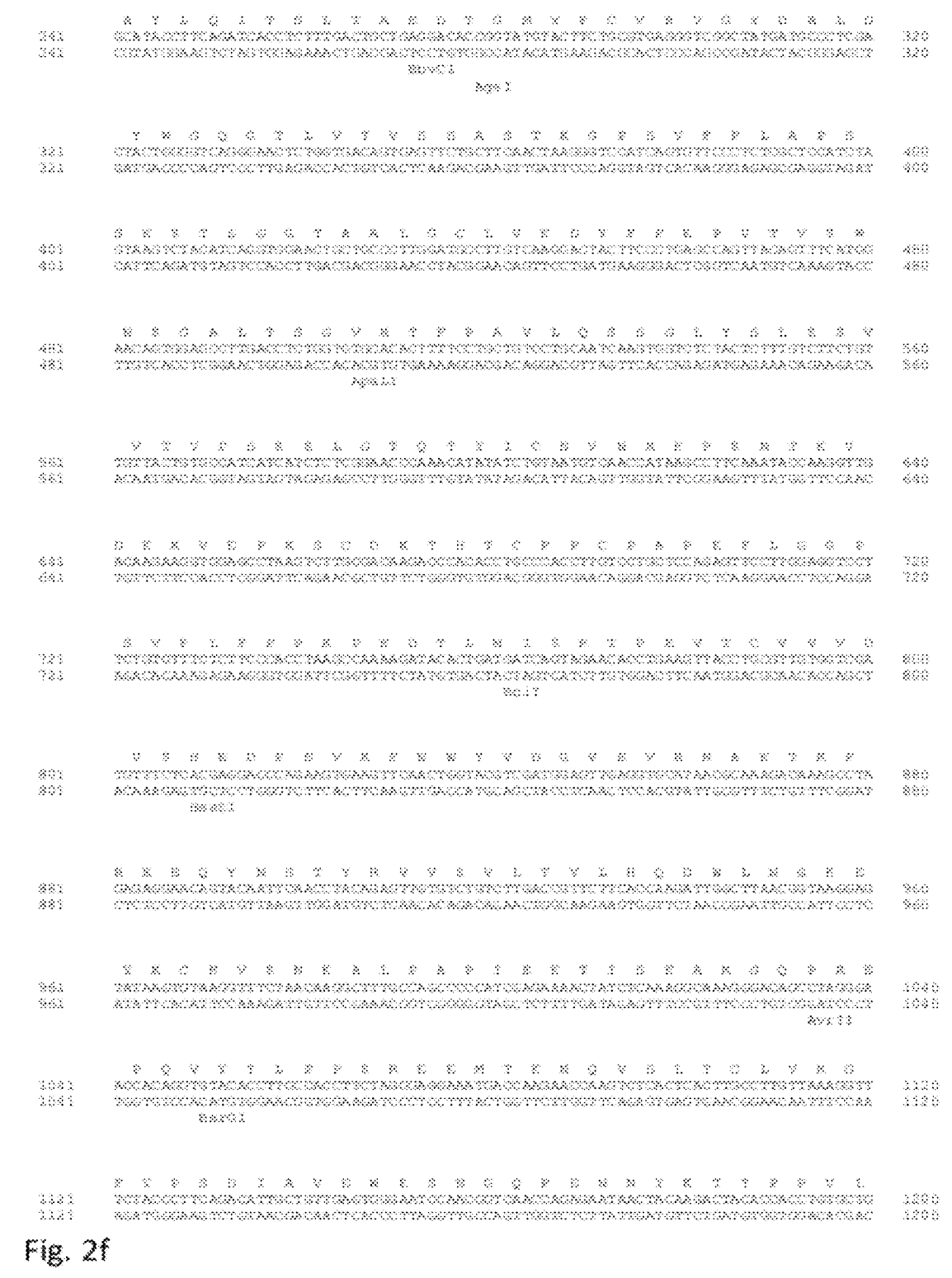
Figure 2G:
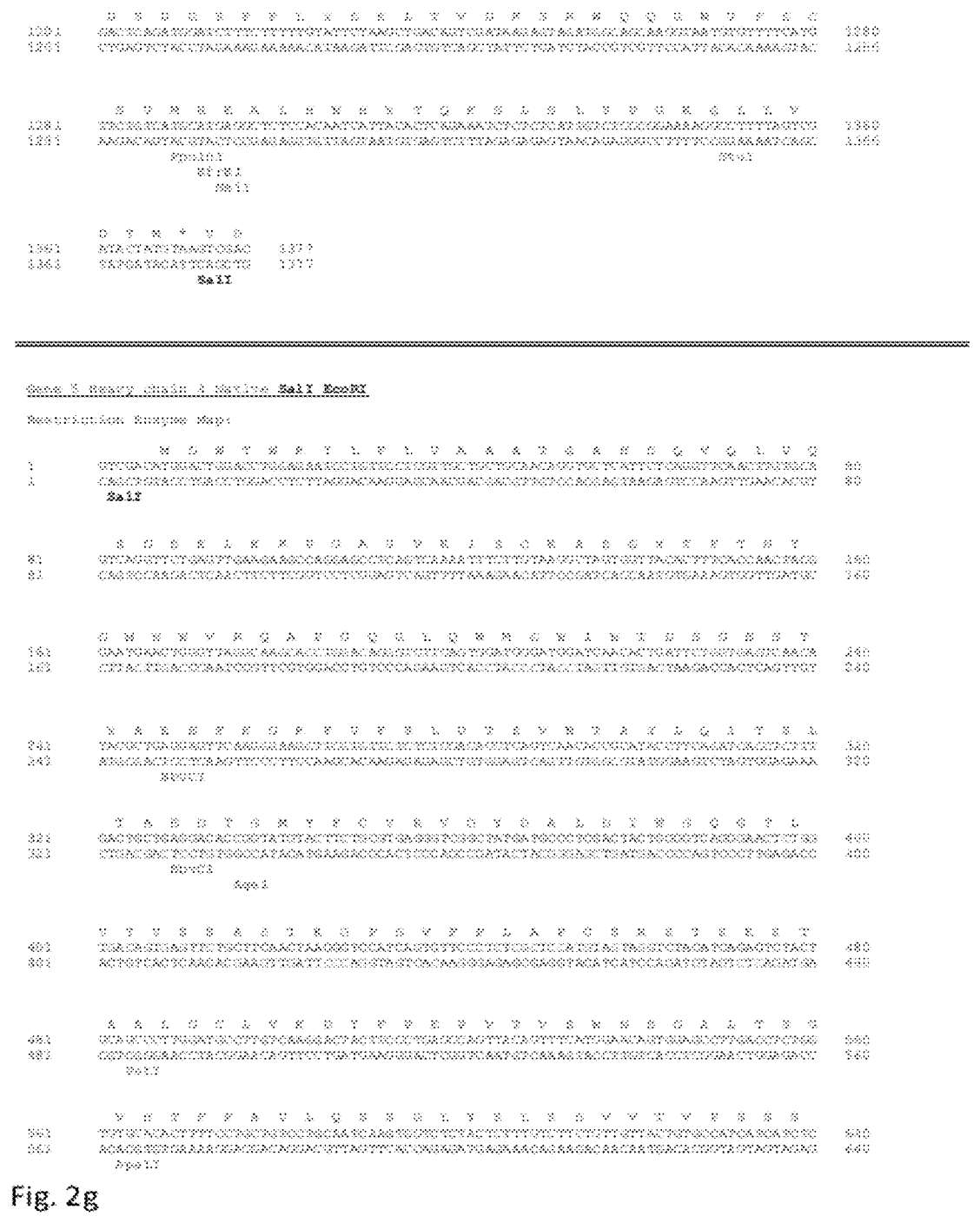
Figure 2H:
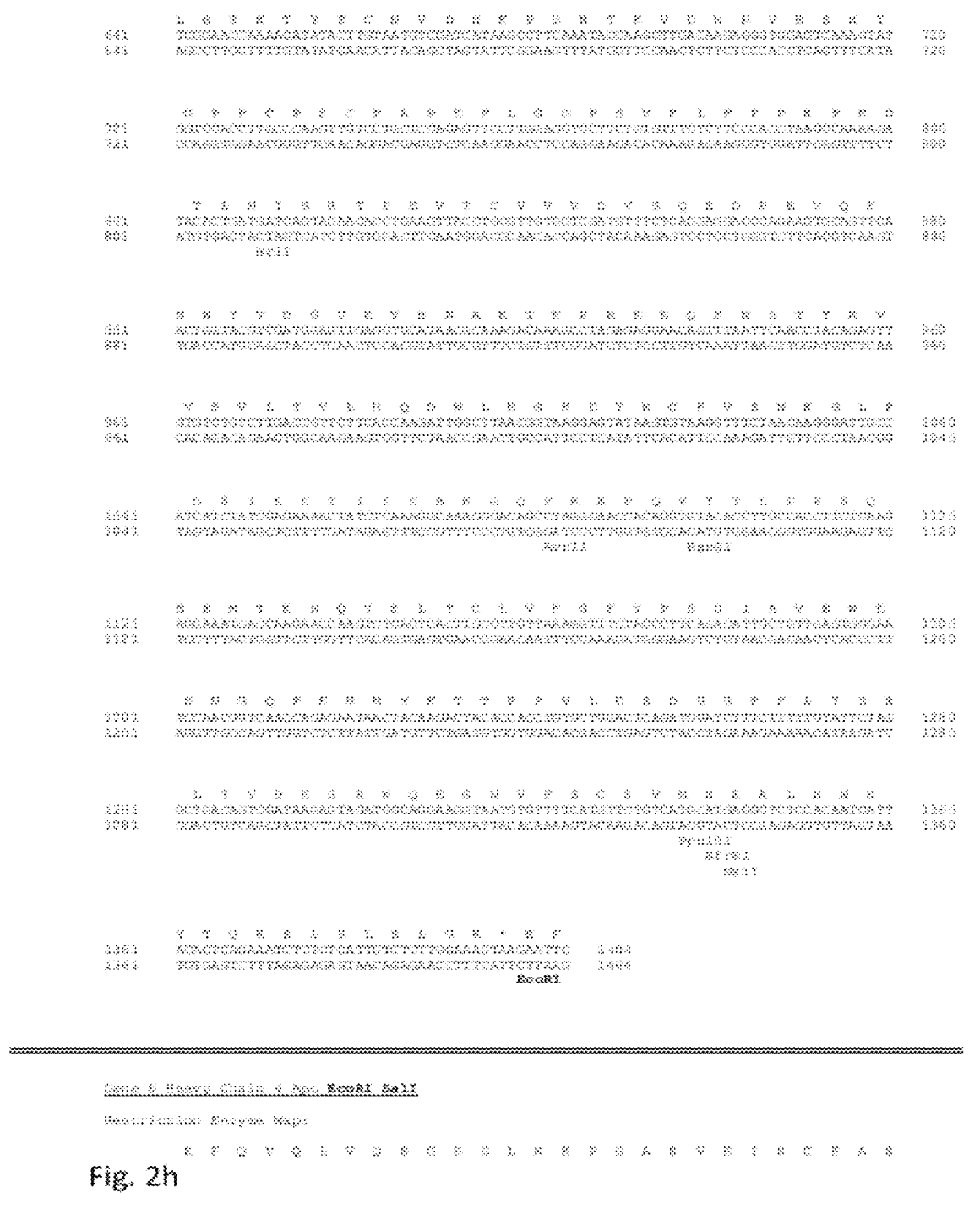
Figure 2I:
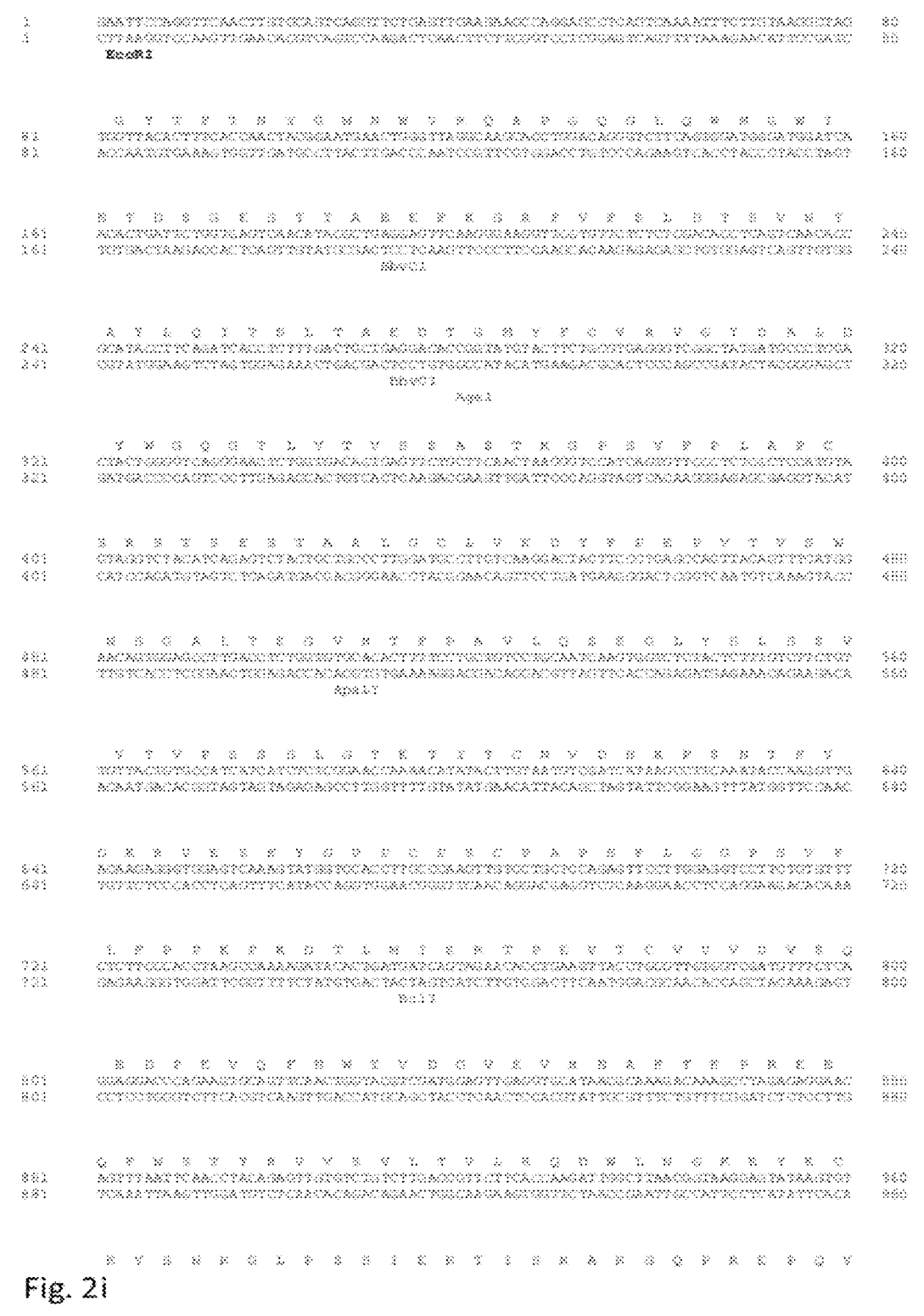
Figure 2J:
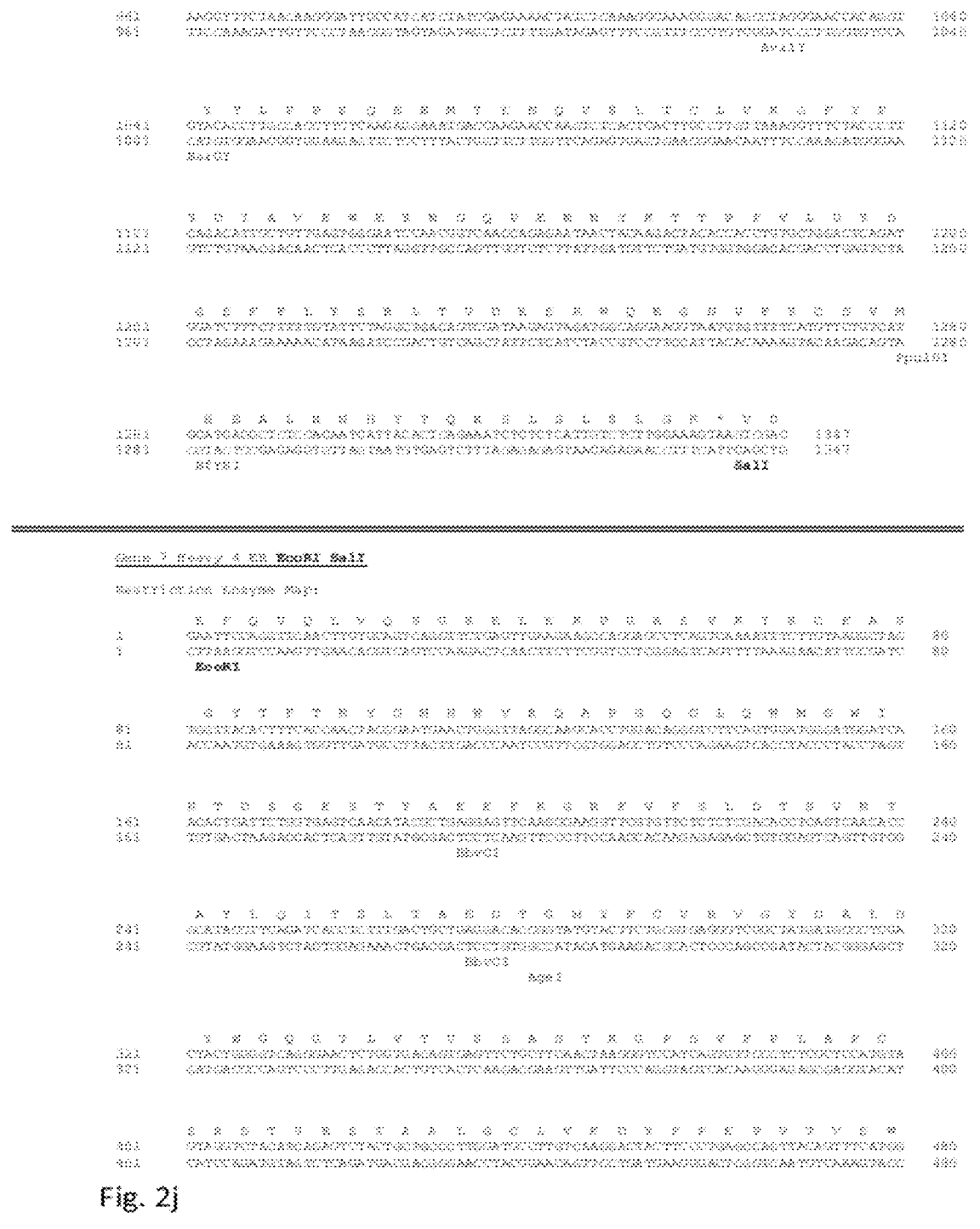
Figure 2K:
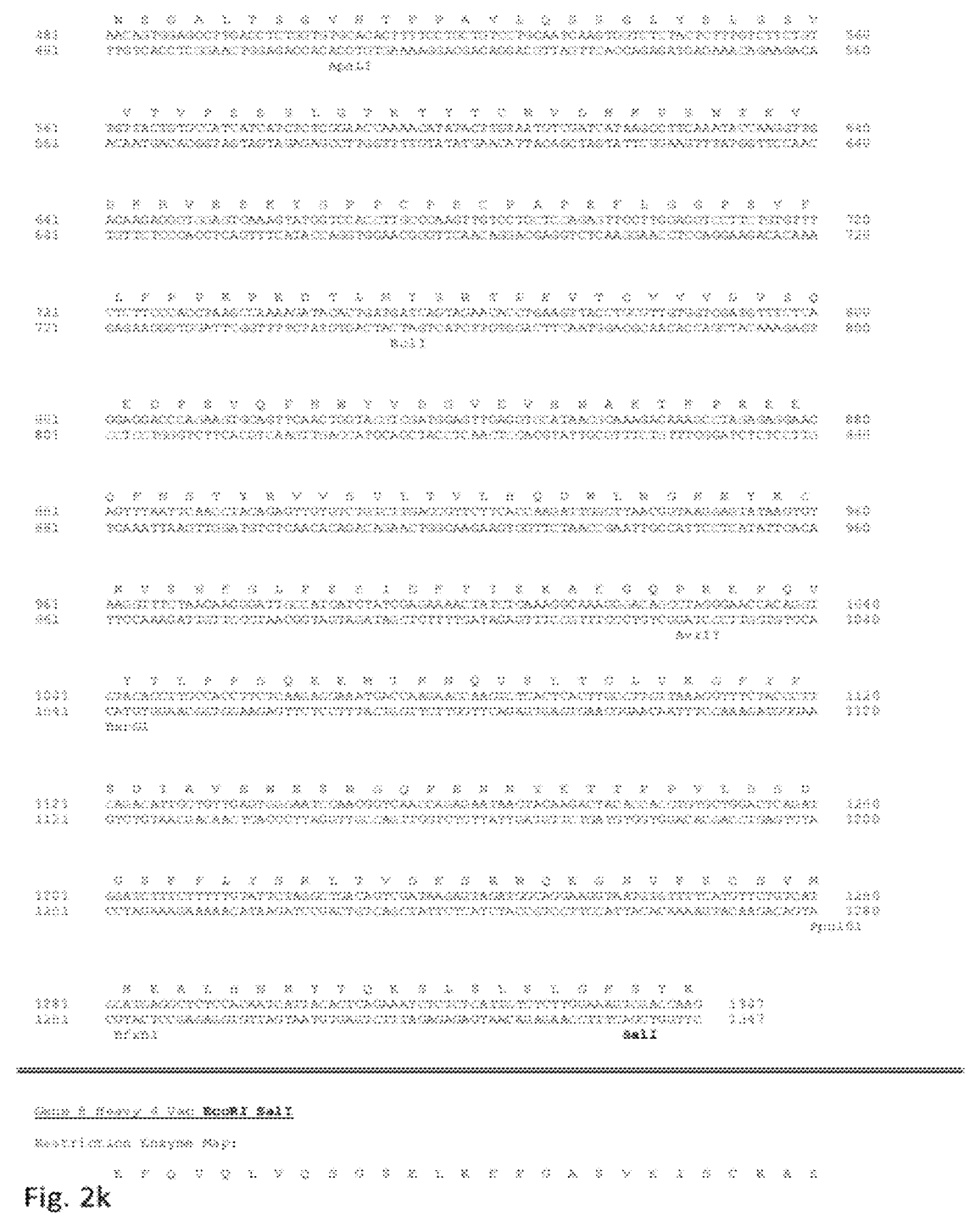
Figure 2M:
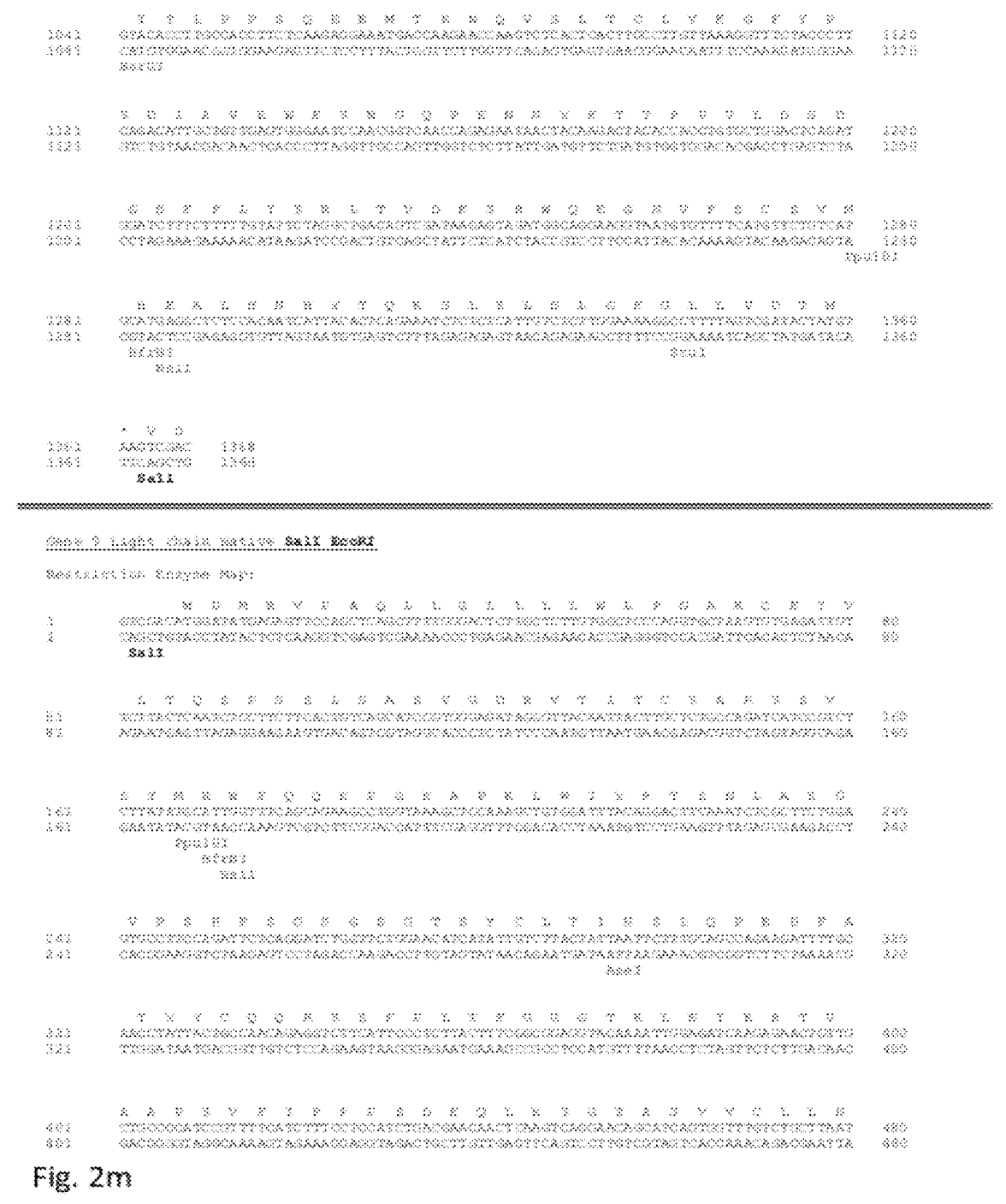
Figure 2N:
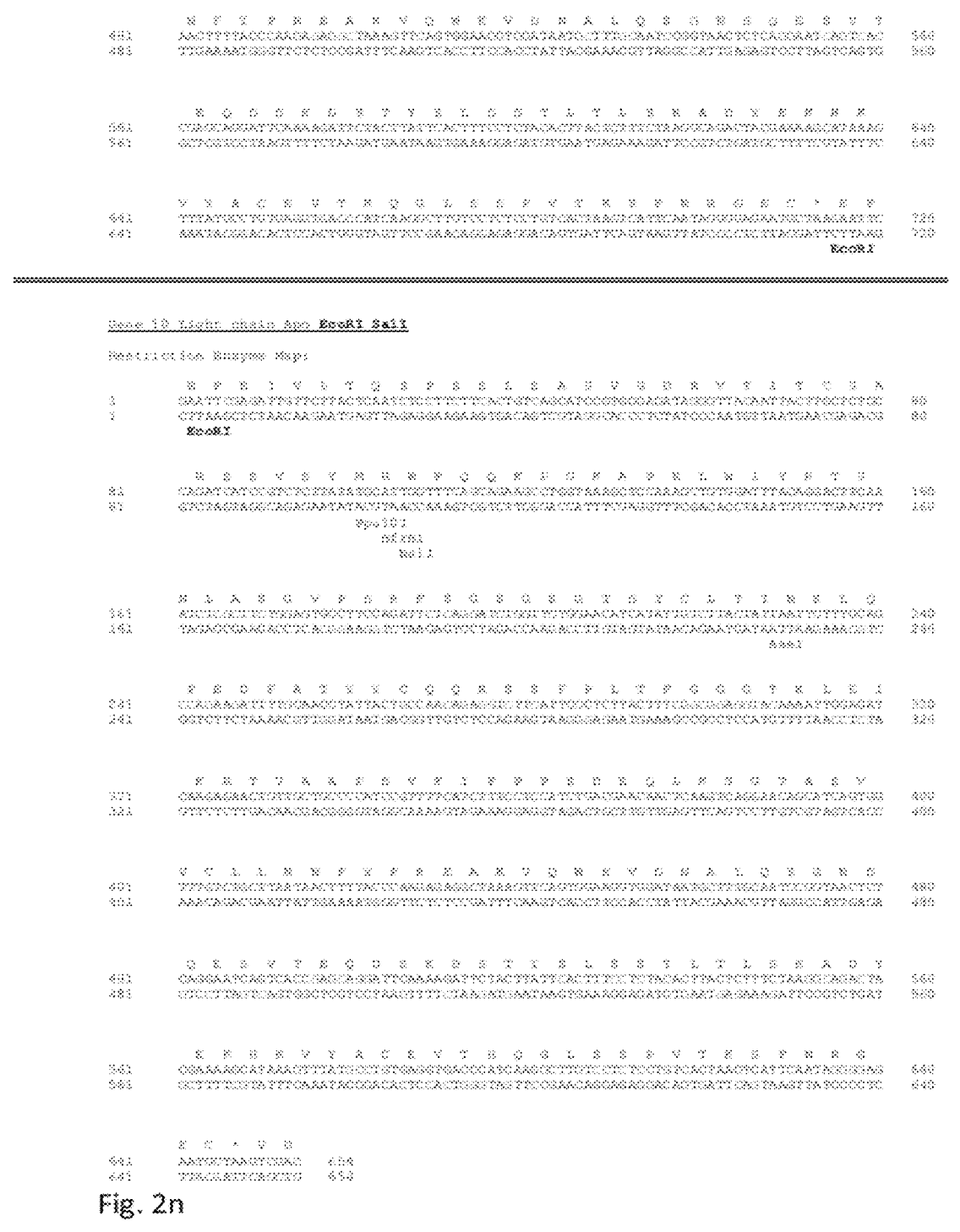
Figure 2O:
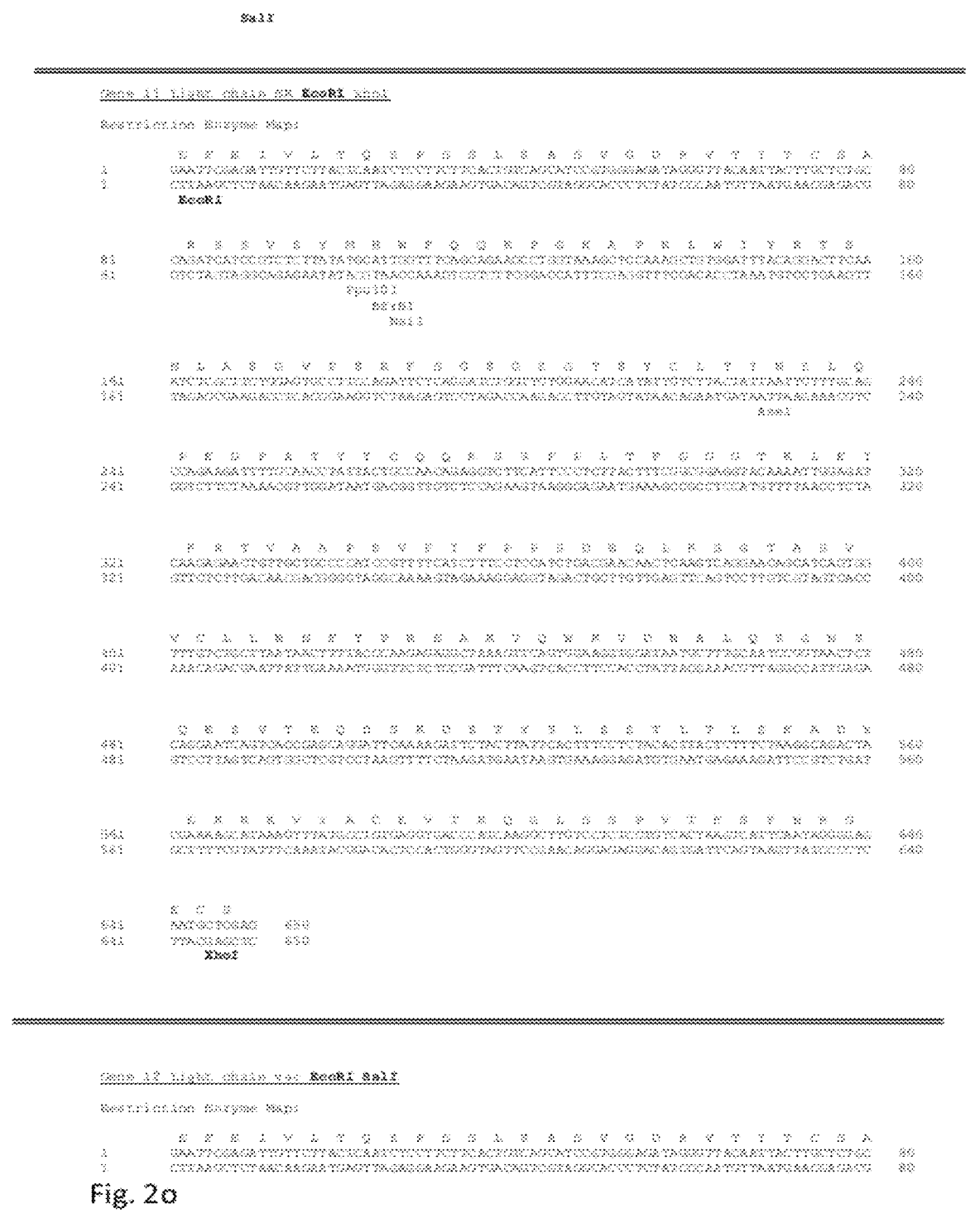
Figure 2P:
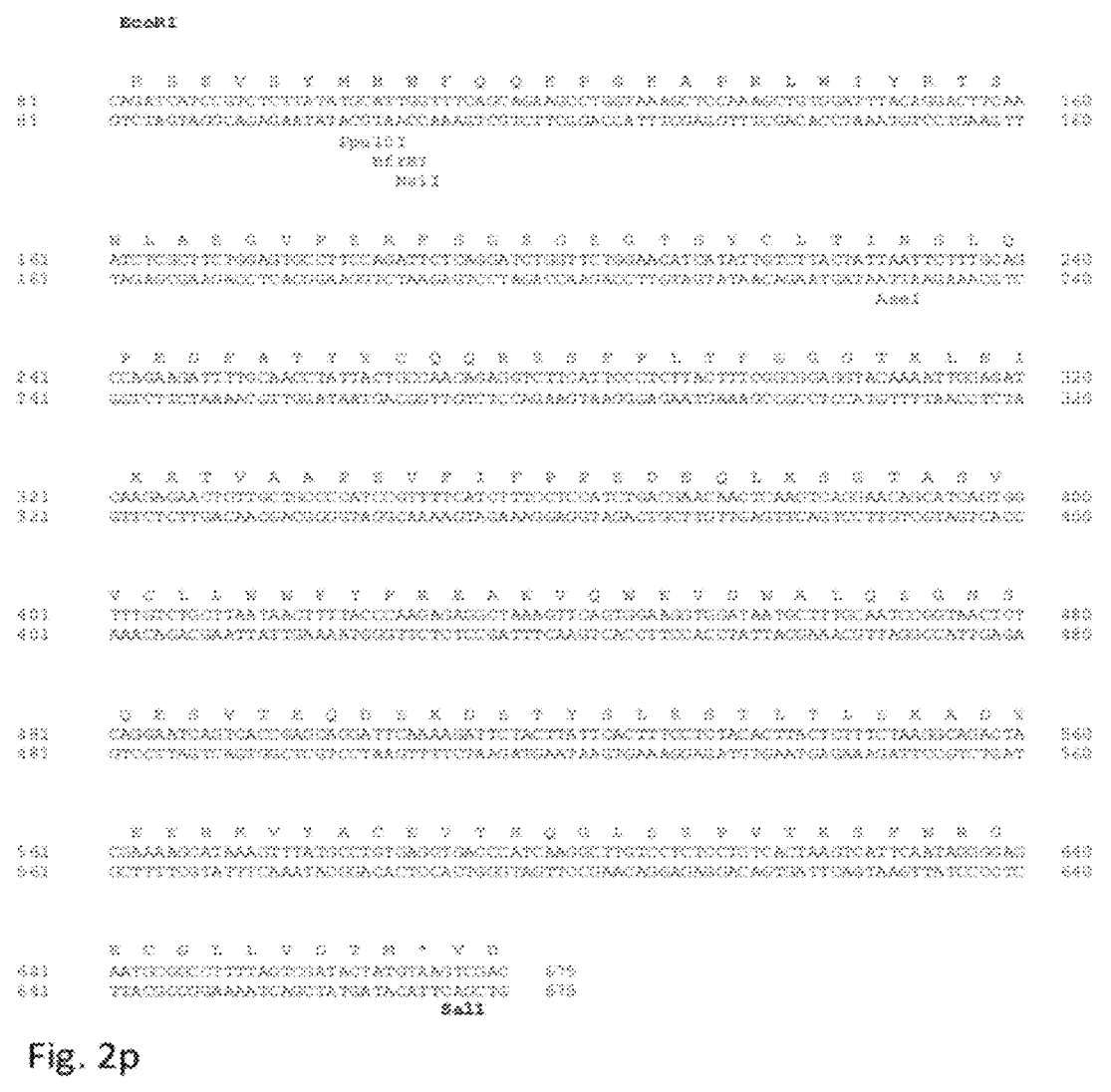

FIG. 2 shows sequences of the synthetic genes for the antibody; the deduced amino acid sequence is displayed above the nucleotide sequence. Major restriction sites are displayed below the nucleotide sequence. Restriction sites used for subcloning are in bold type. The sequences are as follows (names followed by the restriction sites present; those used for cloning are in bold type):

Gene 1 Heavy chain 1 NATIVE Sal-EcoRI (SEQ ID NO: 1) and corresponding translated polypeptide (SEQ ID NO: 17)

Gene 2 Heavy chain 1 Apo EcoRI-SalI (SEQ ID NO: 2) and corresponding translated polypeptide (SEQ ID NO: 18)

Gene 3 Heavy chain 1 ER EcoRI SalI (SEQ ID NO: 3) and corresponding translated polypeptide (SEQ ID NO: 19)

Gene 4 Heavy chain 1 vac EcoRI SalI (SEQ ID NO: 4) and corresponding translated polypeptide (SEQ ID NO: 20)

Gene 5 Heavy chain 4 Native SalI EcoRI (SEQ ID NO: 9) and corresponding translated polypeptide (SEQ ID NO: 21)

Gene 6 Heavy Chain 4 Apo EcoRI SalI (SEQ ID NO: 10) and corresponding translted polypeptide (SEQ ID NO: 22)

Gene 7 Heavy 4 ER EcoRI SalI (SEQ ID NO: 11) and corresponding translated polypeptide (SEQ ID NO: 23)

Gene 8 Heavy 4 Vac EcoRI SalI (SEQ ID NO: 12) and corresponding translated polypeptide (SEQ ID NO: 24)

Gene 9 Light chain Native SalI EcoRI (SEQ ID NO: 5) and corresponding translated polypeptide (SEQ ID NO: 25)

Gene 10 Light chain Apo EcoRI SalI (SEQ ID NO: 6) and corresponding translated polypeptide (SEQ ID NO: 26)

Gene 11 Light chain ER EcoRI XhoI (SEQ ID NO: 7) and corresponding translated polypeptide (SEQ ID NO: 27)

Gene 12 Light chain vac EcoRI SalI (SEQ ID NO: 8) and corresponding translated polypeptide (SEQ ID NO: 28)

Figure 3A:
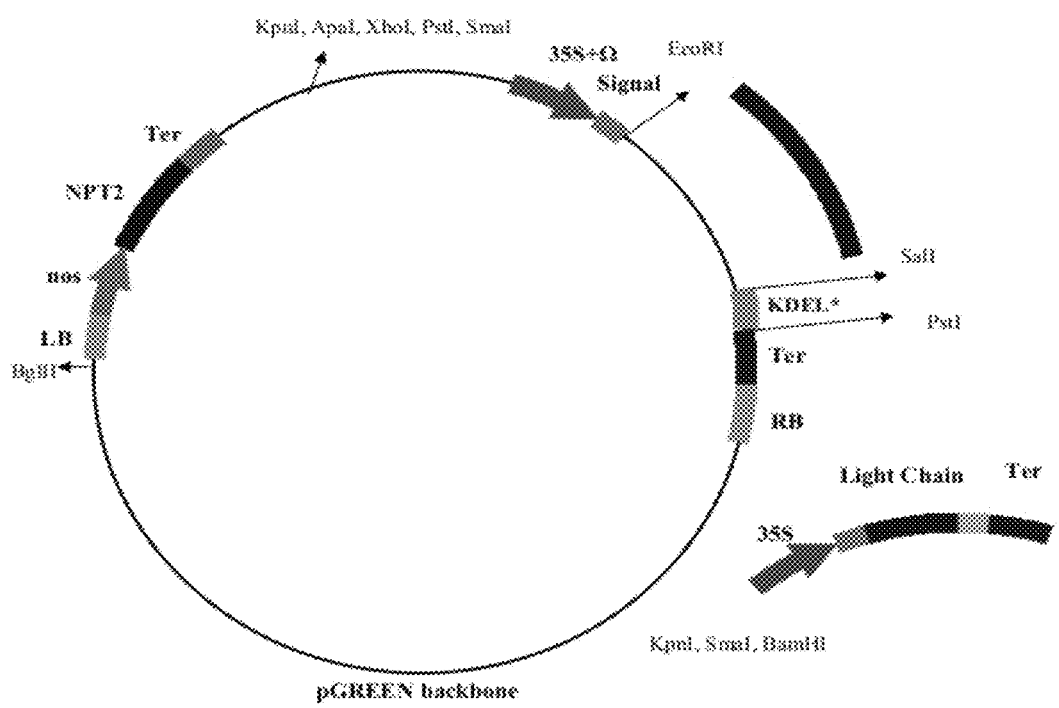
Figure 3B:
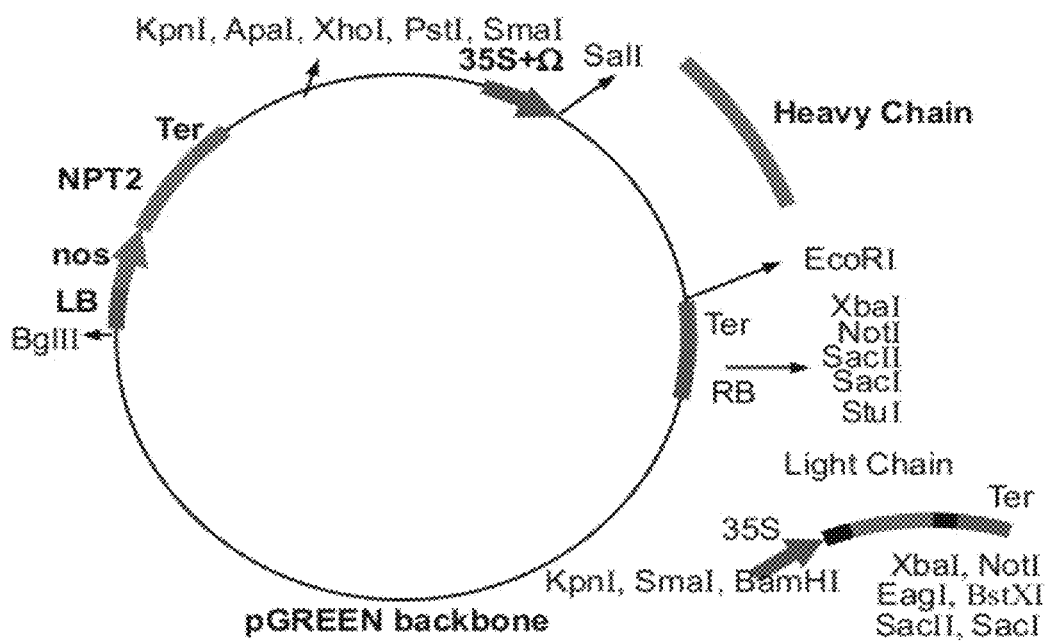

FIGS. 3A and 3B show the cloning of the synthetic genes into expression cassette and binary vectors; FIG. 3A shows construction of the synthetic genes with the plant targeting signal: the synthetic gene contains one of the following—a stop codon before the restriction site, so that it is targeted to the apoplast (constructs 2,6,10), a sequence coding for vacuole targeting peptide followed by a stop codon (targeted to the vacuole; constructs 4, 8, 12), or no signal sequence and is fused to an ER retention signal (targeted to the ER; constructs 3, 7, 11); FIG. 3B shows construction of the synthetic genes with the human signal peptide sequence. The synthetic genes start with the human natural antibody signal and end with a stop codon.

FIGS. 4A and 4B show expression of IgG1 (FIG. 4A) and IgG4 (FIG. 4B) heavy and light chains as detected by Western blot analysis. Transformed carrot calli were screened for production of heavy and light antibody chains. 1 g of callus was homogenized with extraction buffer and 15 mg were run on SDS-PAGE and transferred to nitrocellulose for western blot analysis. Heavy and light chains were detected with specific anti FC and anti Kappa antibodies. FIG. 4A shows transformed calli expressing IgG1(1+9). Standard (St.) IgG1 heavy and light chains are indicated. The lanes represent different calli screened. FIG. 4B shows transformed calli expressing IgG4 (5+9). Standard (St.) IgG4 heavy and light chains are indicated. The lanes represent different calli screened.

FIG. 5 shows a Western blot analysis of antibodies produced with productive cell lines according to the present invention, with assembled IgG1 (A) and IgG4 (B). Cell suspensions of selected calli were analyzed for assembled IgG1 or IgG4 production and secretion. 1 g of cells was homogenized with extraction buffer and 15 mg of soluble extract and 20 ml of medium were run on non-reducing SDS-PAGE and transferred to nitrocellulose for western blot analysis. Assembled IgG1 and IgG4 chains were detected with anti FC antibodies. Numbers represent different calli isolated and standard IgG4 is indicated.

Figure 6A:
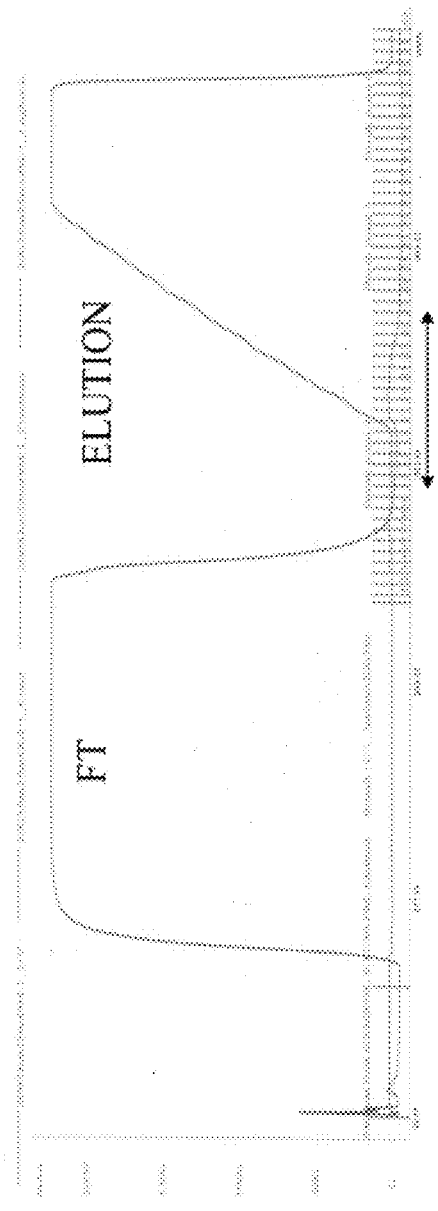
Figure 6B:
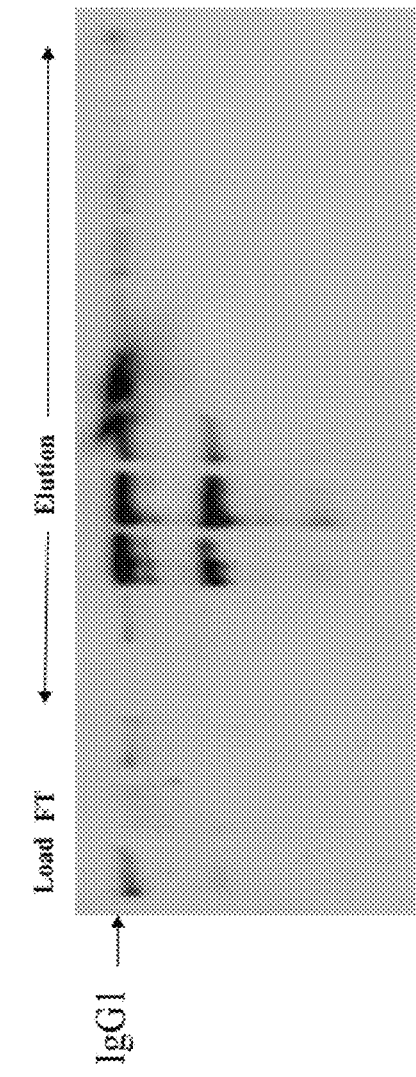

FIGS. 6a-b shows separation of IgG1 expressing cell extract on Macro Prep High S cation exchange column The first step in IgG1 purification was performed by chromatography column as follows: Clarified extract was loaded on a strong cation exchange column (Macro-Prep high-S support, Bio-Rad) equilibrated in 25 mM sodium citrate buffer pH 5.5. Elution of the IgG1 was performed with equilibration buffer containing 1M NaCl. Fractions collected during the run were run on non-reducing SDS-PAGE and analyzed by western blot analysis. FIG. 6A shows a standard run of cell extract on cation exchange column. Blue represents absorbance at 280 nm, and green represents conductivity. Fraction numbers are indicated. FIG. 6B shows fractions collected during the run, which were run on non-reducing SDS-PAGE and transferred to nitrocellulose for western blot analysis. Assembled IgG1 chains were detected with anti FC antibody. Total protein load and flow threw (FT) are indicated Numbers represent elution fractions and standard IgG1 is indicated.

FIGS. 7a-b shows separation of IgG4 expressing cell extract on Macro Prep High S cation exchange column. The first step in IgG4 purification was performed by chromatography column as follows: Clarified extract was loaded on a strong cation exchange column (Macro-Prep high-S support, Bio-Rad) equilibrated in 25 mM sodium citrate buffer pH 5.5. Elution of the IgG4 was performed with equilibration buffer containing 1M NaCl. Fractions collected during the run were run on non-reducing SDS-PAGE and analyzed by western blot analysis. FIG. 7A shows a standard run of cell extract on cation exchange column. Blue represents absorbance at 280 nm, and red represents salt gradient. Fraction numbers are indicated. FIG. 7B. Fractions collected during the run were run on non-reducing SDS-PAGE and transferred to nitrocellulose for western blot analysis. Assembled IgG4 chains were detected with anti FC antibodies. Total protein load and flow threw (FT1,FT2) are indicated. Numbers represent elution fractions and standard IgG4 is indicated.

Figure 9A:
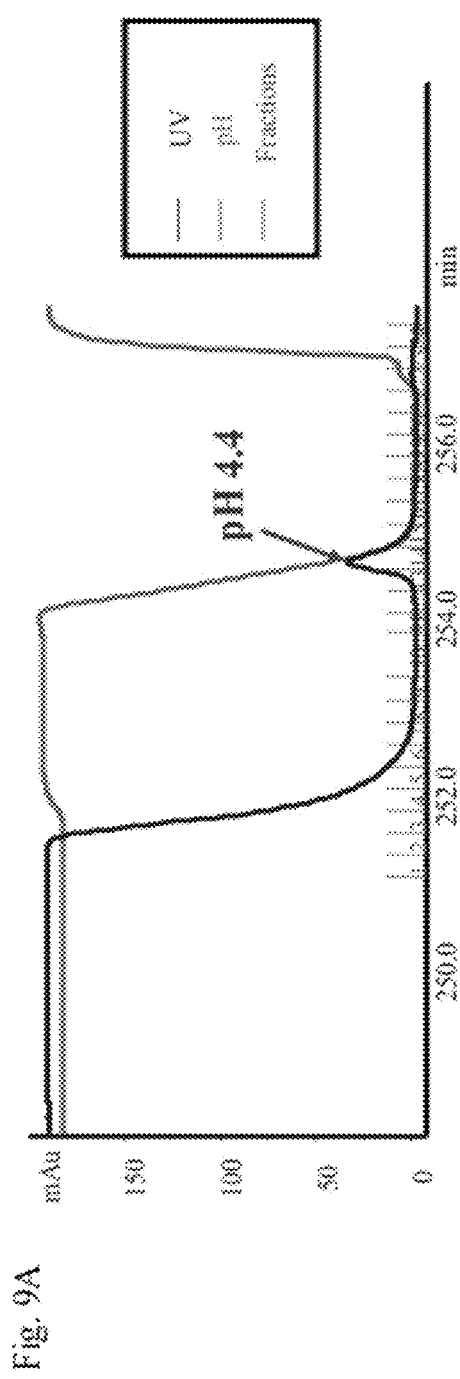
Figure 9B:
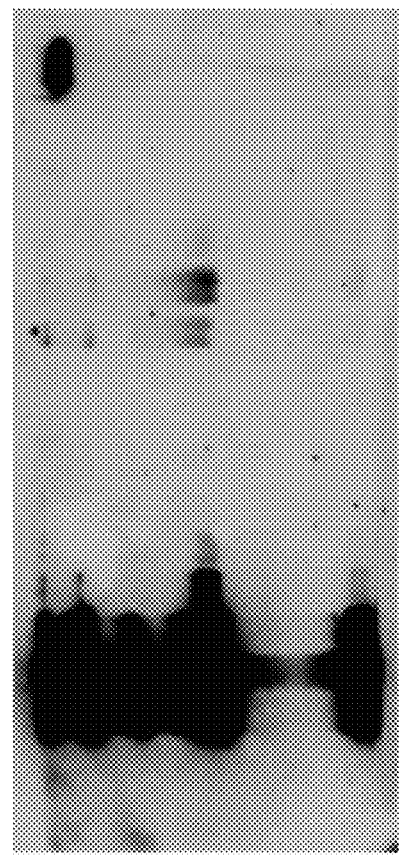

FIGS. 8a-b and 9a-b represent a typical run on protein A of IgG1 (FIG. 8A) and IgG4 (FIG. 9A), along with western blot analysis of selected fractions (FIG. 8B and FIG. 9B).

FIGS. 8a-b shows IgG1 containing fractions from Cation exchange elution separated on Protein A sepharose. The second step in IgG1 purification was performed by Protein A chromatography column as follows: IgG4 containing fractions from cation exchange column were pooled and separated on a Protein-A sepharose column (Sigma). Elution of the IgG1 was performed Citric buffer at pH 4.4. Fractions collected during the run were run on non-reducing SDS-PAGE and analyzed by western blot analysis. FIG. 8A shows a standard run on Protein A sepharose column. FIG. 8B. Fractions collected during the run were run on non-reducing SDS-PAGE and transferred to nitrocellulose for western blot analysis. Assembled IgG1 chains were detected with anti FC antibodies. Total protein load is indicated. Numbers represent elution fractions and standard IgG1 is indicated.

FIGS. 9a-b show IgG4 containing fractions from Cation exchange elution separated on Protein A sepharose. The second step in IgG4 purification was performed by Protein A chromatography column as follows: IgG4 containing fractions from cation exchange column were pooled and separated on a Protein-A sepharose column (Sigma). Elution of the IgG4 was performed with citric buffer at pH 4.4. Fractions collected during the run were run on non-reducing SDS-PAGE and analyzed by western blot analysis. FIG. 9A shows a standard run on Protein A sepharose column. FIG. 9B. Fractions collected during the run were run on non-reducing SDS-PAGE and transferred to nitrocellulose for western blot analysis. Assembled IgG4 chains were detected with anti FC antibodies. Total protein load is indicated. Numbers represent elution fractions and standard IgG4 is indicated.

FIGS. 10a-b and 11a-b show Western blot and Coomassie staining of the purified IgG1 and IgG4 proteins, respectively.

FIG. 10 shows Western blot and coomassie stain of purified IgG1. Purified Protalix-IgG1 and commercial (standard) IgG1 were run on non-reducing SDS-PAGE and analyzed by western blot (A) with anti FC antibodies and Coomassie stain (B). FIG. 10A shows IgG1 standard 50 ng (1), Protalix IgG1 diluted 1:5 (2). FIG. 10B shows IgG1 standard: 1 mg (1), 0.5 mg (2), MW markers (3), Protalix IGg1 (4-7). Size of MW markers are indicated FIG. 11 shows a Western blot and coomassie stain of purified IgG4. Purified Protalix-IgG4 and commercial (standard) IgG4 were run on non-reducing SDS-PAGE and analyzed by western blot (A) with anti FC antibodies and Coomassie stain (B). FIG. 11A shows IgG4 standard 100 ng (1), 50 ng (2), 25 ng (3), Protalix IgG4 diluted 1:5 (4). FIG. 11B shows IgG4 standard: 1 mg (1), 0.5 mg (2), 0.25 mg (3), 0.125 mg(4), Protalix IGg4 (5). Size of MW markers are indicated.

Figures 12A, 12B:
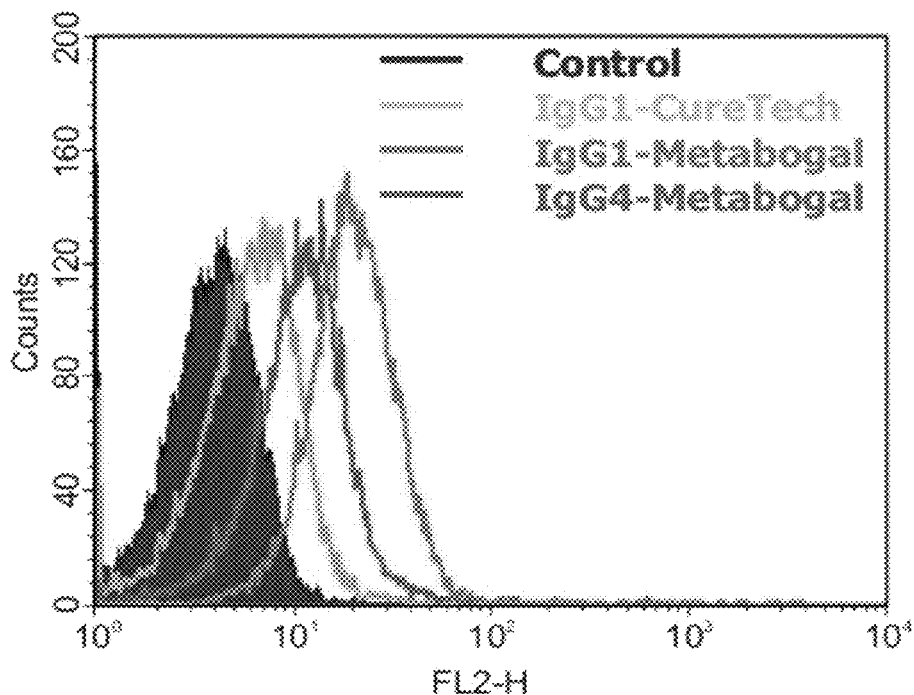

FIGS. 12A and 12B show a shift in fluorescent intensity of cells incubated with Protalix's IgG1, IgG4 and CureTech's IgG1 as determined with FACS analysis. Jurkat cells expressing specific surface antigen were incubated with 0.1 ml of purified antibody at 50 mg/ml. Bound antibody was detected using biotinilated anti human IgG antibody followed by PE-conjugated Streptavidin. Unlabeled cells were used as control. A: FACS analysis of cells stained with different antibodies (see legend), B: Mean fluorescence of samples analyzed.

DETAILED DESCRIPTION OF PREFERRED EMBODIMENTS

The present invention is of a system and method for producing antibodies in plant cell culture. The present invention also encompasses the antibodies produced according to the system and method thereof (with the exception of the Curetech antibody, which is the exemplary antibody herein and is provided for the purposes of illustration of the present invention (and its best practice) and without any intention of being limiting in any way), and also host cells and vectors thereof.

Surprisingly, and contrary to the teachings of the background art, the inventors have found that the antibodies according to the present invention have higher binding efficiency as compared to antibodies produced in mammalian cell culture. Furthermore, the inventors were also able to produce a stable and highly functional IgG4 type antibody, which had not been previously demonstrated in plant cell culture. Indeed, expression of IgG4 has never been demonstrated in plant cell culture (or any type of plant cells).

Without wishing to be limited by a single hypothesis, it is possible that the greater binding affinity of antibodies produced according to the present invention, as opposed to those produced in mammalian cell culture, may be related to differential glycosylation. Antibodies have at least two important biological functions that are differently affected by the glycosylation pattern of the antibodies themselves. Antibodies need to be able to bind an antigen, on the one hand, but also need to be able to activate the effector ligands in order to activate the immune system.

An operative antibody activates the immune system as follows. Once the antibody has bound to its antigen, the antibody recruits the immune system and destroys the target featuring the antigen (for example a malignant cell). The FC region of the antibody can interact with factors that activate the immune system and that cause recruitment of macrophage cells, B and T cells. Antibodies also activate the complement system, which includes proteins found in the blood, along with cells of the immune system. Once activated, the complement system can bring about a variety of responses. This complement system consists of three separate activation triggers: (1) antibody binding to a cell surface, (2) formation of immune complexes, and (3) a carbohydrate component of a foreign cell membrane. The ability to activate the effector ligands is affected by the particular type and extent of glycosylation, as previously described.

However, binding of the antibody to the antigen is not affected by glycosylation (see for example references 27 and 32). The illustrative antibody produced in the plant cell culture system according to the present invention is shown to have greater affinity for the antigen and to bind the antigen more strongly than IgG1 antibody produced in mammalian CHO cells. Also, this exemplary antibody was stably produced as a functional example of the IgG4 subtype, which was not previously demonstrated to be possible in a plant cell culture system.

Plant cells can be cultivated in vitro as clumps of de-differentiated cells on solid media (callus), or as cell suspensions, using current 'Good Laboratory Practice' (cGLP) and 'Good Manufacturing Practice' (cGMP) (44). Compared to mammalian cell cultures, the cultivation of plant cells is relatively inexpensive and the cells are generally more robust than animal cell cultures. Importantly, plant cells possess the endogenous membrane system and auxiliary protein machinery required for the correct assembly, folding and possible secretion of immunoglobulins. Initial protein glycosylation closely matches the pattern observed in mammalian systems, although differences have been observed within the terminal sugar residues of recombinant proteins (45) (18).

The basic biosynthesis pathway of high-mannose and complex N-linked glycans is highly conserved among all eukaryotes including plants. The use of different signal peptides, and thus different intracellular trafficking can alter glycosylation patterns and improve protein activity and stability compared to other expression systems (see e.g., WO2004/096978).

The structures of the N-linked glycans attached to the heavy chains of the monoclonal antibody Guy's 13 produced in transgenic tobacco plants (plantibody Guy's 13) were identified and compared to those found in the corresponding IgG1 of murine origin (29). Both N-glycosylation sites located on the heavy chain of the plantibody Guy's 13 are N-glycosylated as in mouse. However, the number of Guy's 13 glycoforms is higher in the plant than in the mammalian expression system. Despite the high structural diversity of the plantibody N-glycans, glycosylation appears to be sufficient for the production of a soluble and biologically active IgG in the plant system. Since plant glycoproteins display different glycosylation patterns to those exhibited by mammalian glycoproteins, the potential of these plant recombinant antibodies to induce undesirable immune responses in mammals was investigated. Analyses showed undetectable levels of antibody directed against both the protein and the glycan part of the plant recombinant antibody. These results have a direct relevance for the application of plant recombinant proteins as therapeutic agents and vaccines in humans (47).

As mentioned although plants glycosylate human proteins at the correct position, the composition of fully processed complex plant glycans differ from mammalian N-linked glycans. Plant glycans do not have the terminal sialic acid residue or galactose residues common in animal glycans and often contain a xylose or fucose residue with a linkage that is generally not found in mammals (Jenkins et al., 14 Nature Biotech 975-981 (1996); Chrispeels and Faye in transgenic plants pp. 99-114 (Owen, M. and Pen, J. eds. Wiley & Sons, N. Y. 1996; Russell 240 Curr. Top. Microbio. Immunol. (1999). Specifically, plants comprise additional beta 1-2 linked xylosyl- and alpha 1-3 linked fucosyl-residues which are not found in mammals. Conversely they do not comprise fucosyl-1-6-residues which are present in mammals. Thus, the present invention teaches of antibodies, preferably of the IgG4 isotype with a plant glycosylation pattern.

As used herein a plant glycosylation pattern comprises at least one beta 1-2 linked xylosyl or at least one alpha 1-3 linked fucosyl-residue. The glycosylation pattern may also partly comprise a human glycosylation pattern—e.g., galactose or sialic acid residues.

It will be appreciated that sialic acid residues are required for pharmacokinetic reasons extending the in-vivo half-life of the associated polypeptide in the human recipient. Thus, the present invention contemplates for example, the use of various strategies to address the issue of "humanization" of glycans of antibody products synthesized in plants so that the antibody product preferably comprises a part plant glycosylation pattern and a part human glycosylation pattern (described in length hereinabove).

Expression of IgG4 antibodies has been described in milk of transgenic goats and in the mouse myeloma cell line NSO (48,49). Anti TGFbeta2 IgG4 expressed in NSO cells has high affinity to TGFbeta2 and neutralizes the anti-proliferative effect of TGFbeta2, and has been suggested in therapy of fibrotic diseases mediated by TGFbeat2. However, the glycosylation pattern of proteins produced in NSO cells differs from that in humans. For example, the glycoside structure includes an additional galactose alpha(1-3) structure that represents an immunogenic epitope. It is estimated that 1% of circulating IgG is a specific antibody directed against this epitope. Infusion of recombinant antibody bearing that epitope would therefore lead to the formation of immune complexes and provoke systemic inflammatory response (49) (50).

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

Following is a non limiting description of terms used throughout the application.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

It must be noted that, as used in this specification and the appended claims, the singular forms "a", "an" and "the" include plural referents unless the content clearly dictates otherwise.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLE 1

Production of an Antibody in the System of the Present Invention

This Example describes the production of an illustrative antibody in the system according to the present invention.
Materials and Methods:
Synthetic Genes Recombinant human IgG sequences were received from CureTech and are shown with regard to FIG. 1. Vectors termed pG1KD210 and pG4KD110 contain both heavy and light chain sequences. pG1KD210 codes for heavy chain γ1 and pG4KD110 codes for heavy chain γ4 (see FIG. 1). All genes contained introns. Using databases and molecular biology programs that are publicly available, the coding regions of the heavy and light chains and the splice sites of the antibody genes were mapped.

Prediction of splice sites was performed by using the NetGene2 program found at: www.cbs.dtu.dk/services/NetGene2/(see also the following references: S. M. Hebsgaard, P. G. Korning, N. Tolstrup, J. Engelbrecht, P. Rouze, S. Brunak: Splice site prediction in *Arabidopsis thaliana* DNA by combining local and global sequence information, 1996, *Nuc. Acids Res.*, 24:3439-3452; Brunak, S., Engelbrecht, J., and Knudsen, S.: Prediction of Human mRNA Donor and Acceptor Sites from the DNA Sequence, 1991 *J. Mol. Biol.*, 220: 49-65).

This was required in order to prepare a synthetic gene without introns that would code for the same amino acid sequence as the original human antibody amino acid sequence, since the human introns might be incorrectly recognized in plants.

After verifying the protein sequences with Curetech (the originators of the human antibody), the sequences were reverse translated using the carrot optimal codon usage. The DNA sequences were modified to avoid restriction sites and sequences that might interfere with high level expression, without modifying the protein sequence.

The codon usage per organism can be found in the Codon Usage Database (www.kazusa.or.jp/codon/). Usually, the frequency of the codon usage reflects the abundance of their cognate tRNAs. Therefore, when the codon usage of your target protein differs significantly from the average codon usage of the expression host, this could cause problems during expression. The following problems are often encountered:

Decreased mRNA stability (by slowing down translation)
Premature termination of transcription and/or translation, which leads to a variety of truncated protein products
Frameshifts, deletions and misincorporations (e.g. lysine for arginine).
Inhibition of protein synthesis and cell growth.

As a consequence, the observed levels of expression are often low or there will be no expression at all, especially in cases where rare codons are present at the 5'-end of the mRNA or in clusters. This causes expression levels to be low, and truncated protein products are found.

The expressed levels can be improved by replacing codons that are rarely found in highly expressed carrot genes with more favorable (frequently used in carrot cells) codons throughout the whole gene.

Restriction sites were introduced before and after the sequences coding for the three antibody chains (γ1, γ4, and κ) to facilitate easy cloning, as shown with regard to FIG. 2. Different modifications of the sequences were performed to permit the recombinant antibody to be targeted to different organelles in the plant cells, in order to examine where maximal expression levels and alternative glycosylation patterns may be achieved (33-36). For this purpose additional constructs were prepared, in which restriction sites were introduced instead of the sequences coding for the original native human signal peptide, in order to replace the signal peptide with a sequence for a plant signal peptide. In order to target the antibodies to the ER, the stop codon was removed to facilitate fusion with the ER retention signal. Targeting to the vacuole was achieved by incorporating a sequence coding for the vacuolar sorting signal GLLVDTM (seq id no: 13) before the stop codon.

The constructs were synthesized by Thermo Hybaid GmbH (Ulm, Germany).

Plasmid vectors

CE-K—Was constructed from plasmid CE obtained from Prof. Galili [U.S. Pat. No. 5,367,110 Nov. 22, (1994)]. Plasmid CE was digested with SalI.

The SalI cohesive end was made blunt-ended using the large fragment of DNA polymerase I. Then the plasmid was digested with PstI and ligated to a DNA fragment coding for the ER targeting signal from the basic endochitinase gene [*Arabidopsis thaliana*]ATGAAGAC-TAATCTTTTTCTCTTTCT-CATCTTTTCACTTCTCCTATC ATTATCCTCGGC-CGAATTC (seq id no: 14), and ER Retention signal KDEL (37) digested with SmaI and PstI.

pGREENII—obtained from Dr. P. Mullineaux (38). Expression from the pGREEN II vector is controlled by the 35S promoter from Cauliflower Mosaic Virus, the TMV (Tobacco Mosaic Virus) omega translational enhancer element and the octopine synthase terminator sequence from *Agrobacterium tumefaciens*.

Construction of Expression Plasmid

The synthetic genes were digested with endonucleases EcoRI and SalI, beside gene 11 light chain ER that was digested with EcoRI and Xho I (see recognition sequences underlined in the synthetic genes). The genes coding for heavy chains were ligated into the binary vector pGREENII carrying the expression cassette digested with EcoRI and SalI. The genes coding for light chains were ligated into an intermediate vector (CEK) carrying the expression cassette and digested with EcoRI and SalI. The expression cassette with the synthetic light chain gene was cut and eluted from the intermediate vector and ligated into the binary vector carrying the corresponding heavy chain, forming the final expression vector (FIG. 3). Kanamycin resistance is conferred by the NPTII gene driven by the nos promoter obtained together with the pGREEN vector (FIG. 3). The resulting expression cassette is shown in FIG. 3.

Table 1 summarizes the different constructs and their designation.

TABLE 1

Construct summary

| Designation | IgG Type | Target signal |
|---|---|---|
| 1 + 9 | Hγ1 + L | in their native form (original signal sequences) |
| 2 + 10 | Hγ1 + L | targeted to the apoplast |
| 3 + 11 | Hγ1 + L | targeted to the endoplasmic reticulum |
| 4 + 12 | Hγ1 + L | targeted to the vacuole |
| 5 + 9 | Hγ4 + L | in their native form (original signal sequences) |
| 6 + 10 | Hγ4 + L | targeted to the apoplast |
| 7 + 11 | Hγ4 + L | targeted to the endoplasmic reticulum |
| 8 + 12 | Hγ4 + L | targeted to the vacuole |

Establishment of Carrot Callus and Cell Suspension Cultures

Establishment of carrot callus and cell suspension cultures was performed as described previously by Torres K. C. (Tissue culture techniques for horticular crops, p.p. 111, 169).

Transformation of Carrot Cells and Isolation of Transformed Cells.

Transformation of carrot cells was preformed using *Agrobacterium tumefaciens* transformation by an adaptation of a method described previously (39) (40). Cells growing in liquid media were used throughout the process instead of calli.

Incubation and growth times were adapted for transformation of cells in liquid culture. Briefly, *Agrobacteria* were transformed with the pGREEN II vector system by electroporation, and then selected using 30 mg/ml paromomycine antibiotic. Carrot cells were transformed with *Agrobacteria* and selected using 60 mg/ml of paromomycine antibiotics in liquid media.

Screening of Transformed Carrot Cells for Isolation of Calli Expressing High Levels of IgG1 and IgG4

14 days following transformation, cells from culture were plated on solid media at dilution of 3% packed cell volume for the formation of calli from individual clusters of cells. When individual calli reached 1-2 cm in diameter, the cells were homogenized in extraction buffer and the resulting protein extracts were separated on SDS-PAGE and transferred to nitrocellulose membrane (hybond C nitrocellulose, 0.45 micron: Amersham Life Science). Western blot for detection of heavy and light chains was preformed using anti FC (Sigma A-0170) and anti Kappa (Sigma A-7164) antibodies. Commercial hIgG1 (Sigma 15154) and hIgG4 (Sigma 14639) antibodies were used as standard. Calli expressing significant levels of IgG1 or IgG4 were expanded and transferred to growth in liquid media for scale up, protein purification and analysis.

Upscale Culture Growth in Protalix's Bioreactors

An individual callus, 1-2 cm in diameter, of genetically modified carrot cells expressing IgG4 or IgG1 was plated onto Murashige and Skoog (MS) 9 cm diameter agar medium plate containing 4.4 gr/l MSD medium (Duchefa), 9.9 mg/l thiamin HCl (Duchefa), 0.5 mg folic acid (Sigma) 0.5 mg/l biotin (Duchefa), 30 g/l sugar, and 0.2 mg/l 2-4 D (Sigma). The callus were subcultured every 2-3 weeks, and grown at 25° C.

Suspension cell culture was prepared by sub-culturing the transformed callus in MSD liquid medium. The suspension cells were cultivated in 250 ml Erlenmeyer flask (working volume starts with 25 ml and after 7 days fresh medium was added to 50 ml) at 25° C. with shaking speed of 120 RPM. Subsequently, cells were sub-cultured every 7 days in fresh media. Inoculum of the small bio-reactor (10 L) containing 4 L MSD medium, was obtained by addition of 400 ml of suspension cells derived from seven-day cell culture. After a week of cultivation at 25° C. with 1 Lpm airflow, MSD medium was added up to 10 L and the cultivation continued under the same conditions. After additional seven days of cultivation, cells were harvested and collected by passing the cell media through 100 mesh net. The access medium was squeezed out and the packed cell cake was stored at −70° C.

SDS-PAGE, Western Blot Analysis and Coomassie Blue Staining

Protein samples were separated by SDS polyacrylamide gel electrophoresis (41) under reducing or non reducing conditions. The gels were either stained with Coomassie blue staining solution (Bio Safe Coomassie Cat. 161-0786, Bio-Rad), or transferred to nitrocellulose membrane (Schleicher and Schuell, Dassel) for western blot analysis.

After transfer to nitrocellulose membranes, free binding sites on the nitrocellulose were saturated at 4° C. over-night with blocking buffer containing 1% dry milk (Dairy America), and 0.1% Tween 20 (Sigma Cat P1379) diluted with phosphate buffer (Riedel deHaen, catalog number 30435). The blots were incubated with an HPR-conjugated antibody (anti FC (Sigma A-0170) and/or anti Kappa (Sigma A-7164), dilution, 1:6500 in phosphate buffer containing 1% dry milk and 0.1% Tween 20 as above, pH 7.5, at 25° C. for 1.5 hour.

After incubation with the antibody, the blots were washed three times for in each case 10 minutes with PBS with 0.05% Tween 20, and three times with PBS. The blot strips were stained with ECL developer reagents (Amersham RPN 2209). After immersing the blots in the ECL reagents the blots were exposed to X-ray film FUJI Super RX 18x24, and developed with FUJI-ANATOMIX developer and fixer (FUJI-X fix cat# FIXRTU 1 out of 2) The bands featuring proteins that were bound by the antibody became visible after this treatment.

Protein Purification

The purification procedure was the same for both IgG1 and IgG4. For IgG purification, frozen cell cake containing about 1 kg wet weight cells was thawed, and the IgG was extracted by homogenization of the cells in 1 L extraction buffer (20 mM sodium phosphate pH 7.4, 20 mM EDTA, 0.1 mM PMSF, 20 mM ascorbic acid, 0.1 mM DTT). The homogenate was clarified by centrifugation at 17000 g for 20 min at 4° C. The pellet was discarded and the supernatant was concentrated by ultrafiltration with 30K MWCO membrane. The pH of the 30K retentate was adjusted to pH 5.5 by addition of concentrated citric acid. Turbidity generated after pH adjustment was clarified by centrifugation under the same conditions described above.

Further purification was performed by chromatography columns as follows: 1250 ml of clarified extract were loaded on 135 ml strong cation exchange resin (Macro-Prep high-S support, Bio-Rad) equilibrated in 25 mM sodium citrate buffer pH 5.5, packed in a XK column (2.6×20 cm). The column was integrated with an AKTA prime system (Amersham Pharmacia Biotech) that allowed monitoring of the conductivity, pH and absorbency at 280 nm. The sample was loaded at 45 ml/min, afterwards the column was washed with equilibration buffer (25 mM sodium citrate buffer pH 5.5) at flow rate of 45 ml/min until UV absorbency reached the base line. Elution of the IgG4 was performed with equilibration buffer containing 1M NaCl. Fractions collected during the run were run on non-reducing SDS-PAGE and analyzed by western blot analysis. Fractions containing IgG were pooled. pH of pooled samples was adjusted to 7.5 with NaOH.

Sample containing the IgG was applied to a 10 ml protein A sepharose column. Sample was loaded at 10 ml/min followed by washing with equilibration buffer (100 mM Citrate phosphate buffer pH=7.5) until the UV absorbance reached the baseline. The purified assembled IgG was eluted with 0.1M Citrate buffer pH=3.4, and fractions containing IgG were pooled. The pH of the elution pool was adjusted to pH=7.5 with 1M Tris (Sigma T-6066) pH 8 and stored at −20° C.

Determination of Total Protein Concentration

Protein concentrations in cell extracts and fractions were assayed by the method of Lowry/Bradford (Bio Rad protein assay Cat. 500-0006) (42), using a bovine serum albumin standard (BSA fraction V Sigma A-2153). Alternatively, concentration of homogenous protein samples was determined by absorption at 280 nm, 1 mg/ml=1.4 $O.D._{280}$. Purity was determined by 280/260 nm ratio.

Mammalian Cell Culture

Jurkat cells, clone E6-1 (ATCC Catalog No. TIB-152), were grown in RPMI medium (Biological industries 01-104-1A) supplemented with 10% FCS (Biological industries 04-121-1A), 2 mM L-glutamine (Biological industries 03-020-1B), 1 mM Na-pyruvate (Biological industries 03-042-1B), 10 mM Hepes (Biological industries 03-025-1C), Pen-Strep-Nys (Biological industries 03-032-1B). Cells were grown in incubator at 37° C. with 5% $CO_2$. These cells were chosen since they apparently express the antigen of these antibodies on the cell surface.

Determination of IgG1 and IgG4 Binding to Jurkat Cells by Fluorescent Staining and FACS Analysis.

$5\times10^5$–$1\times10^6$ Jurkat cells expressing specific surface antigen (recognized by the previously described antibodies) were centrifuged for 7 min at 1500 rpm, the media was removed and cells were washed 3 times with 0.5 ml wash buffer (PBS with 5% FCS and 0.05% Sodium Azide (Sigma S-2002)) and incubated with 0.1 ml of purified antibody at 50 μg/ml. After 45 min incubation on ice, cells were washed twice with wash buffer. Bound antibody was detected using biotinylated anti human IgG antibody (SBA Cat. 2040-08) diluted 1:100 in wash buffer, 100 μl/sample for 45 min on ice. Cells were then washed twice with wash buffer followed by incubation with PE-conjugated Streptavidin (R-Phycoenythrin conjugated streptavidin, Jackson Cat. 016-110-084) diluted 1:100, 100 μl/sample for 30 min on ice in the dark. Unlabeled cells and cells stained only with PE-conjugated streptavidin were used as control. The cells were then washed twice with wash buffer and suspended in 1 ml wash buffer. FACS analysis was preformed on a Beckenton-Dickinson FACS-Caliber machine with Cellquest software.

Results:

Expression of IgG1 and IgG4 Heavy and Light Chains in Transformed Carrot Cells with Different Organelle Targeting.

The recombinant antibody was targeted into different organelles to achieve maximal expression levels and alternative glycosylation patterns. For this purpose additional constructs were prepared in which the original native human signal peptide was replaced by a plant signal peptide. Antibodies with the ER retention signal, the vacuolar sorting signal, and a construct devoid of C terminal targeting sequence that targets the recombinant protein for secretion (apoplast) were all prepared.

Following transformation of carrot cells by *Agrobacterium* transformation, expression of heavy and light chains was examined. Interestingly, screening of cells transformed with the different constructs demonstrated that the construct having the human natural antibody signal sequence of both IgG1 and IgG4 (corresponding to constructs Genes 1 and 9, and Genes 5 and 9 [Seq id no's: 3 and 7, and 11 and 7 respectively]) were the most potent constructs, while the others exhibited undetectable levels of IgG (data not shown; without wishing to be limited by a single hypothesis, the expression levels may have been very low and/or the resultant proteins may be unstable and so degraded).

Expression of IgG1 (FIG. 4A) and IgG4 (FIG. 4B) heavy and light chains by Western blot analysis is presented in FIG. 4, which features a random screening of calli (about 100 calli were screened for each construct).

Furthermore, it is clear from FIG. 4 that there are different levels of expression of the heavy and light chains. Further screening was done to assess the amount of assembled IgG expressed and the level of secretion to the medium. Of the various calli tested, one from each line were selected for scale-up growth and protein purification.

FIG. 5 shows a Western blot analysis of antibodies produced with productive cell lines according to the present invention. Selected calli from the initial screening (FIG. 4) were transferred to liquid medium for growth and expansion. Cell suspensions of selected calli were analyzed for assembled IgG1 or IgG4 production and secretion to growth medium. FIG. 5A (IgG1) shows that although some protein was found in the medium, more was found in the extracted fractions. FIG. 5B (IgG4) shows little to no protein in the medium, with some in the extracted fractions.

Purification of IgG1 and IgG4 from Transformed Carrot Cells

The purification procedure was the same for both IgG1 and IgG4. Following homogenization, soluble IgGs were purified using chromatography techniques, including cation exchange and Protein A affinity columns, as described in materials and methods.

FIGS. 6A and 7A show the results of a typical run of clarified protein extract of IgG1 and IgG4 on the cation exchange column. Fractions collected during the run were run on non-reducing SDS-PAGE and analyzed by western blot analysis, as seen in FIG. 6B and FIG. 7B.

The IgG elution pool from the cation exchange column was purified on Protein A affinity column. FIGS. 8 and 9 represent a typical run on protein A of IgG1 (FIG. 8A) and IgG4 (FIG. 9A), along with western blot analysis of selected fractions (FIG. 8B and FIG. 9B).

Western blot and Coomassie staining of the purified IgG1 and IgG4 proteins shown in FIGS. 10 and 11 demonstrate that the IgGs produced in plant cells exhibit several major protein bands. While the expected size of IgGs run under non-reducing conditions on SDS-PAGE is >175 kDa, as demonstrated by the commercial standard human IgG1 and IgG4, plant cell expressed IgG1 exhibits another major band at 150 kDa and IgG4 exhibits two additional bands at 150 kDa and 50 kDa. These additional bands may be result of dis or mis assembly, as well as of degradation, without wishing to be limited by a single hypothesis.

Assembled antibodies consist of 2 heavy chains and 2 light chains, they are held together by disulphide bridges and other protein-protein interactions. However, in some cases the bonds can break and form again resulting in different combinations of heavy-heavy, heavy light or light-light that have different sizes and will show different bands in SDS-PAGE and western blot analysis.

Degradation is less likely since these bands appear even in preparations that are directly eluted from Protein A column, which are specific to assembled IgG. Evidence of in vivo exchange of IgG half-molecules (one heavy and one light chain) among IgG4, due to changes between interchain and intrachain disulphide bridges (43). The heavy and light chins are held together by disulphide bonds—called interchain, but there are also bonds within the heavy and light chains themselves—intrachain.

Determination of IgG1 and IgG4 Binding to Jurkat Cells by Fluorescent Staining and FACS Analysis.

CureTech's IgG1 was raised against membranes from B cell leukemia, Daudi cells, and their reported target and activity is on T cells. The ability of antibodies IgG1 and IgG4, produced in the cell culture system according to the present invention, to bind the specific antigen present on Jurkat cells (acute T cell leukemia) to which the original IgG1 antibody bound was determined. Results of FACS analysis, presented in FIG. 12, show a shift in fluorescent intensity of cells incubated with Protalix's IgG1, IgG4 and CureTech's IgG1. The increase in mean fluorescence of Protalix's IgGs compared to CureTech's IgG1 presented in FIG. 12B indicate that the binding of plant cell expressed IgG1 and IgG4 to target is at higher affinity than mammalian CHO cell expressed IgG1.

Discussion:

The recombinant antibody was targeted into different organelles according to the present invention to achieve maximal expression levels and alternative glycosylation patterns. Interestingly, screening of cells transformed with the different constructs, demonstrated that the constructs containing the native ER signal of both IgG1 and IgG4 were the most potent constructs in terms of quantity. This implies that plant cells are able to utilize the "built in" targeting signals that are part of the human antibody heavy and light chain genes.

The possibility of acquiring different glycosylation patterns on the same protein by manipulation of intracellular traffic (and hence the resultant glycosylation) can serve as a tool for producing proteins with different glycosylation structures that will provide information about the role of carbohydrate in protein function, and insights into how changes in carbohydrate structure affect protein conformation.

The present invention demonstrates that using the native human leader peptide, the antibodies are accumulated in the cells as well as secreted to the medium (data not shown). Purification of the antibodies from plant cell material utilized state of the art extraction and chromatography techniques which advantageously use the unique behavior of plant cell host proteins in these methodologies. For example, under certain conditions, most of the carrot host cell protein did not bind to the ion exchange chromatography column, while the IgGs did bind to the column. This allowed for rapid purification of antibodies from the plant cell proteins, after which the assembled antibodies were further purified on protein A. It is still to be determined if the glycosylation pattern of these antibodies expressed in plant cells is similar to that of the native protein, although it presumably is because of the stability and functional behavior of the antibodies.

The ability of plant cell expressed antibodies to bind to their antigen at comparative levels with the mammalian cell expressed antibody has been demonstrated (18,46). Affinity of purified plant-cell expressed antibody C5-1 for its antigen was compared to that of hybridoma expressed antibody C5-1 by measuring the dissociation constants at equilibrium, results were $4.7 \times 10^{-10}$M and $4.6 \times 10^{-10}$M respectively. Stability and blood clearance rates were also compared and were found to be similar for both plant cell and mammalian cell expressed antibody (46).

By contrast, the results with the system and method according to the present invention show that surprisingly the binding of plant cell expressed IgG1 and IgG4 antibodies to their antigen occurred with a higher affinity compared to IgG1 expressed in CHO cells. The binding of IgG4 to antigen was even stronger than IgG1, indicating a higher affinity of this antibody subclass. Expression levels of IgG4 in this plant based system are much higher than those seen in mammalian cell expression system (data not shown). This further strengthens the unique abilities of the plant cell system.

Production of recombinant human IgG1 and IgG4 molecules in plant cell suspension, that are properly assembled and able to recognize their epitope, introduces a new technique that combined with Protalix's proprietary bioreactor configuration will allow production of recombinant human antibodies of different isotopes on a commercial scale.

Thus, the present invention provides a novel, scaleable, cost-effective production and purification process for recombinant human antibodies produced in transgenic plant cells in suspension, such as transgenic carrot cells.

EXAMPLE 2

Treatment with the Present Invention

The recombinant protein produced according to the present invention preferably comprises an antibody produced by a plant cell culture, which is preferably IgG4 but which may optionally be IgG1.

According to preferred embodiments herein, the antibody produced according to the present invention is suitable for treatment of a disease which is susceptible to treatment with such an antibody.

The method of treatment optionally and preferably comprises: (a) providing a recombinant biologically active antibody purified from transformed plant root cells, and capable of efficiently targeting an antigen. In a preferred embodiment, the recombinant antibody used by the method of the invention may be produced by the host cell of the invention. Preferably, this host cell is a carrot cell.

By "mammalian subject" or "mammalian patient" is meant any mammal for which therapy is desired, including human, bovine, equine, canine, and feline subjects, most preferably, a human subject.

It should be noted that the term "treatment" also includes amelioration or alleviation of a pathological condition and/or one or more symptoms thereof, curing such a condition, or preventing the genesis of such a condition.

In another preferred embodiment, antibody is an IgG4 having stronger binding capability for an antigen than the equivalent IgG4 produced in mammalian cell culture. Therefore, each dose may optionally be less than the dose of the antibody that would otherwise be administered in a similar manner to achieve the therapeutic effect. Alternatively, the antibody may be administered in a similar dose to achieve a higher therapeutic effect.

The protein (antibody) of the present invention can be used to produce a pharmaceutical composition. Thus, according to another aspect of the present invention there is provided a pharmaceutical composition which includes, as an active ingredient thereof, a protein and a pharmaceutical acceptable carrier. As used herein a "pharmaceutical composition" refers to a preparation of one or more of the active ingredients described herein, such as a recombinant protein, with other chemical components such as traditional drugs, physiologically suitable carriers and excipients. The purpose of a pharmaceutical composition is to facilitate administration of a protein or cell to an organism. Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

In a preferred embodiment, the term "pharmaceutically acceptable" means approved by a regulatory agency of the Federal or a state government or listed in the U.S. Pharmacopeia or other generally recognized pharmacopeia for use in animals, and more particularly in humans. Hereinafter, the phrases "physiologically suitable carrier" and "pharmaceutically acceptable carrier" are interchangeably used and refer to an approved carrier or a diluent that does not cause significant irritation to an organism and does not abrogate the biological activity and properties of the administered conjugate.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the protein, preferably in purified form, together with a suitable amount of carrier so as to provide the form for proper administration to the patient. The formulation should be suitable for the mode of administration.

Herein the term "excipient" refers to an inert substance added to a pharmaceutical composition to further facilitate processes and administration of the active ingredients. Examples, without limitation, of excipients include calcium carbonate, calcium phosphate, various sugars and types of starch, cellulose derivatives, gelatin, vegetable oils and polyethylene glycols.

Further techniques for formulation and administration of active ingredients may be found in "Remington's Pharmaceutical Sciences," Mack Publishing Co., Easton, Pa., latest edition, which is incorporated herein by reference as if fully set forth herein.

The pharmaceutical compositions herein described may also comprise suitable solid or gel phase carriers or excipients. Examples of such carriers or excipients include, but are not limited to, calcium carbonate, calcium phosphate, various sugars, starches, cellulose derivatives, gelatin and polymers such as polyethylene glycols.

Suitable routes of administration may, for example, include oral, rectal, transmucosal, transdermal, intestinal or parenteral delivery, including intramuscular, subcutaneous and intramedullary injections as well as intrathecal, direct intraventricular, intravenous, intraperitoneal, intranasal, or intraocular injections.

Pharmaceutical compositions for use in accordance with the present invention thus may be formulated in conventional manner using one or more pharmaceutically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological saline buffer. For transmucosal administration, penetrants are used in the formulation. Such penetrants are generally known in the art.

For oral administration, the active ingredients can be optionally formulated through administration of the whole cells producing an antibody according to the present invention. The active ingredients can also be formulated by combining the active ingredients and/or the cells with pharmaceutically acceptable carriers well known in the art. Such carriers enable the active ingredients of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active ingredient doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the active ingredient and a suitable powder base such as lactose or starch.

The active ingredients described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

In a preferred embodiment, the composition is formulated in accordance with routine procedures as a pharmaceutical composition adapted for intravenous administration to human beings. Typically, pharmaceutical compositions for intravenous administration are solutions in sterile isotonic aqueous buffer. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The active ingredients of the present invention may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

The topical route is optionally performed, and is assisted by a topical carrier. The topical carrier is one which is generally suited for topical active ingredient administration and includes any such materials known in the art. The topical carrier is selected so as to provide the composition in the desired form, e.g., as a liquid or non-liquid carrier, lotion, cream, paste, gel, powder, ointment, solvent, liquid diluent, drops and the like, and may be comprised of a material of either naturally occurring or synthetic origin. It is essential, clearly, that the selected carrier does not adversely affect the active agent or other components of the topical formulation, and which is stable with respect to all components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like. Preferred formulations herein are colorless, odorless ointments, liquids, lotions, creams and gels.

Ointments are semisolid preparations, which are typically based on petrolatum or other petroleum derivatives. The specific ointment base to be used, as will be appreciated by those skilled in the art, is one that will provide for optimum active ingredients delivery, and, preferably, will provide for other desired characteristics as well, e.g., emolliency or the like. As with other carriers or vehicles, an ointment base should be inert, stable, nonirritating and nonsensitizing. As explained in Remington: The Science and Practice of Pharmacy, 19th Ed. (Easton, Pa.: Mack Publishing Co., 1995), at pages 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight; again, reference may be made to Remington: The Science and Practice of Pharmacy for further information.

Lotions are preparations to be applied to the skin surface without friction, and are typically liquid or semiliquid preparations, in which solid particles, including the active agent, are present in a water or alcohol base. Lotions are usually suspensions of solids, and may comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as active ingredients useful for localizing and holding the active agent in contact with the skin, e.g., methylcellulose, sodium carboxymethylcellulose, or the like.

Creams containing the selected active ingredients are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington, supra, is generally a nonionic, anionic, cationic or amphoteric surfactant.

Gel formulations are preferred for application to the scalp. As will be appreciated by those working in the field of topical active ingredients formulation, gels are semisolid, suspension-type systems. Single-phase gels contain organic macromolecules distributed substantially uniformly throughout the carrier liquid, which is typically aqueous, but also, preferably, contain an alcohol and, optionally, an oil.

Various additives, known to those skilled in the art, may be included in the topical formulations of the invention. For example, solvents may be used to solubilize certain active ingredients substances. Other optional additives include skin permeation enhancers, opacifiers, anti-oxidants, gelling agents, thickening agents, stabilizers, and the like.

The topical compositions of the present invention may also be delivered to the skin using conventional dermal-type patches or articles, wherein the active ingredients composition is contained within a laminated structure, that serves as a drug delivery device to be affixed to the skin. In such a structure, the active ingredients composition is contained in a layer, or "reservoir", underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during active ingredients delivery. Examples of suitable skin contact adhesive materials include, but are not limited to, polyethylenes, polysiloxanes, polyisobutylenes, polyacrylates, polyurethanes, and the like. The particular polymeric adhesive selected will depend on the particular active ingredients, vehicle, etc., i.e., the adhesive must be compatible with all components of the active ingredients-containing composition. Alternatively, the active ingredients-containing reservoir and skin contact adhesive are present as separate and distinct layers, with the adhesive underlying the reservoir which, in this case, may be either a polymeric matrix as described above, or it may be a liquid or hydrogel reservoir, or may take some other form.

The backing layer in these laminates, which serves as the upper surface of the device, functions as the primary structural element of the laminated structure and provides the device with much of its flexibility. The material selected for the backing material should be selected so that it is substantially impermeable to the active ingredients and to any other components of the active ingredients-containing composition, thus preventing loss of any components through the upper surface of the device. The backing layer may be either occlusive or non-occlusive, depending on whether it is desired that the skin become hydrated during active ingredients delivery. The backing is preferably made of a sheet or film of a preferably flexible elastomeric material. Examples of polymers that are suitable for the backing layer include polyethylene, polypropylene, and polyesters.

During storage and prior to use, the laminated structure includes a release liner. Immediately prior to use, this layer is removed from the device to expose the basal surface thereof, either the active ingredients reservoir or a separate contact adhesive layer, so that the system may be affixed to the skin. The release liner should be made from an active ingredients/vehicle impermeable material.

Such devices may be fabricated using conventional techniques, known in the art, for example by casting a fluid admixture of adhesive, active ingredients and vehicle onto the backing layer, followed by lamination of the release liner. Similarly, the adhesive mixture may be cast onto the release liner, followed by lamination of the backing layer. Alternatively, the active ingredients reservoir may be prepared in the absence of active ingredients or excipient, and then loaded by "soaking" in an active ingredients/vehicle mixture.

As with the topical formulations of the invention, the active ingredients composition contained within the active ingredients reservoirs of these laminated system may contain a number of components. In some cases, the active ingredients may be delivered "neat," i.e., in the absence of additional liquid. In most cases, however, the active ingredients will be dissolved, dispersed or suspended in a suitable pharmaceutically acceptable vehicle, typically a solvent or gel. Other components, which may be present, include preservatives, stabilizers, surfactants, and the like.

It should be noted that the antibody of the invention is preferably administered to the patient in need in an effective amount. As used herein, "effective amount" means an amount necessary to achieve a selected result. For example, an effective amount of the composition of the invention may be selected for being useful for the treatment of cancer.

Pharmaceutical compositions suitable for use in context of the present invention include compositions wherein the active ingredients are contained in an amount effective to achieve the intended purpose. More specifically, a therapeutically effective amount means an amount of active ingredient effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any active ingredient used in the methods of the invention, the therapeutically effective amount or dose can be estimated initially from activity assays in animals. For example, a dose can be formulated in animal models to achieve a circulating concentration range that includes the $IC_{50}$ as determined by activity assays.

Toxicity and therapeutic efficacy of the active ingredients described herein can be determined by standard pharmaceutical procedures in experimental animals, e.g., by determining the $IC_{50}$ and the $LD_{50}$ (lethal dose causing death in 50% of the tested animals) for a subject active ingredient. The data obtained from these activity assays and animal studies can be used in formulating a range of dosage for use in humans.

The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma levels of the active moiety which are sufficient to maintain the modulating effects, termed the minimal effective concentration (MEC). The MEC will vary for each preparation, but may optionally be estimated from whole animal data.

Dosage intervals can also be determined using the MEC value. Preparations may optionally be administered using a regimen, which maintains plasma levels above the MEC for 10-90% of the time, preferable between 30-90% and most preferably 50-90%.

Depending on the severity and responsiveness of the condition to be treated, dosing can also be a single administration of a slow release composition described hereinabove, with course of treatment lasting from several days to several weeks or until cure is effected or diminution of the disease state is achieved.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising an active ingredient of the invention formulated in a compatible pharmaceutical carrier may also be prepared, placed in an appropriate container, and labeled for treatment of an indicated condition.

As used herein, the term "modulate" includes substantially inhibiting, slowing or reversing the progression of a disease, substantially ameliorating clinical symptoms of a disease or condition, or substantially preventing the appearance of clinical symptoms of a disease or condition. A "modulator" therefore includes an agent which may modulate a disease or condition.

REFERENCES 1. van Engelen F A, S. A., Molthoff J W, Roosien J, Salinas J, Dirkse W G, Schots A, Bakker J, Gommers F J, Jongsma M A, et al. (1994) *Plant Mol. Biol.* 26,
2. Ma, J. K., Hiatt, A., Hein, M., Vine, N. D., Wang, F., Stabila, P., van Dolleweerd, C., Mostov, K., and Lehner, T. (1995) *Science* 268, 716-719
3. Ma, J. K., Hikmat, B. Y., Wycoff, K., Vine, N. D., Chargelegue, D., Yu, L., Hein, M. B., and Lehner, T. (1998) *Nat Med* 4, 601-606
4. Ma J K, D. P., Christou P. (2003) *Nat Rev Genet.* 4, 794-805.
5. Fischer, R., Emans, N., Schuster, F., Hellwig, S., and Drossard, J. (1999) *Biotechnol Appl Biochem* 30 (Pt 2), 109-112
6. Hiatt A, C. R., Bowdish K. (1989) *Nature* 342, 76-78
7. De Neve M, D. L. M., Jacobs A, Van Houdt H, Kaluza B, Weidle U, Van Montagu M, Depicker A. (1993) *Transgenic Res.* 2, 227-237
8. De Wilde, C., De Rycke, R., Beeckman, T., De Neve, M., Van Montagu, M., Engler, G., and Depicker, A. (1998) *Plant Cell Physiol* 39, 639-646
9. Ramirez N, R. M., Ayala M, Cremata J, Perez M, Martinez A, Linares M, Hevia Y, Paez R, Valdes R, Gavilondo J V, Selman-Housein G. (2003) *Biotechnol Appl Biochem.* 38, 223-230
10. Larrick, J. W., Yu, L., Naftzger, C., Jaiswal, S., and Wycoff, K. (2001) *Biomol Eng* 18, 87-94
11. Schillberg, S., Fischer, R., and Emans, N. (2003) *Cell Mol Life Sci* 60,
12. Schillberg, S., Fischer, R., and Emans, N. (2003) *Naturwissenschaften* 90, 145-155
13. Schillberg, S., Zimmermann, S., Voss, A., and Fischer, R. (1999) *Transgenic Res* 8, 255-263
14. Fischer, R., Hoffmann, K., Schillberg, S., and Emans, N. (2000) *J Biol Regul Homeost Agents* 14, 83-92
15. Fischer, R., Liao, Y. C., Hoffmann, K., Schillberg, S., and Emans, N. (1999) *Biol Chem* 380, 825-839
16. Fischer, R., Drossard, J., Commandeur, U., Schillberg, S., and Emans, N. (1999) *Biotechnol Appl Biochem* 30 (Pt 2), 101-108
17. Fischer, R., Drossard, J., Emans, N., Commandeur, U., and Hellwig, S. (1999) *Biotechnol Appl Biochem* 30 (Pt 2), 117-120
18. Fischer, R., Liao, Y. C., and Drossard, J. (1999) *J Immunol Methods* 226, 1-10
19. Stoger, E., Sack, M., Fischer, R., and Christou, P. (2002) *Curr Opin Biotechnol* 13, 161-166
20. Chadd H E, C. S. (2001) *Curr Opin Biotechnol.* 12, 188-194
21. Jefferis R, G. M., Tishchenko V, Nash P, Lund J. (1995) *Adv Exp Med Biol* 376, 153
22. Jefferis R, L. J., Pound J D. (1998) *Immunol Rev.* 163, 59-76
23. Jefferis R, L. J., Goodall M. (1995) *Immunol Lett.* 44, 111-117
24. Lund J, T. N., Goodall M, Pound J D, Jefferis R. (1995) *Biochem Soc Trans* 23, 102S
25. Lund J, T. N., Pound J D, Goodall M, Nakagawa H, Jefferis R. (1995) *FASEB J* 9, 115-119
26. Tsuchiya N, E. T., Matsuta K, Yoshinoya S, Aikawa T, Kosuge E, Takeuchi F, Miyamoto T, Kobata A. (1989) *J Rheumatol.* 16, 285-290
27. Wright A, M. S. (1994) *J Exp Med.* 180, 1087-1096
28. Bakker, H., Bardor, M., Molthoff, J. W., Gomord, V., Elbers, I., Stevens, L. H., Jordi, W., Lommen, A., Faye, L., Lerouge, P., and Bosch, D. (2001) *Proc Natl Acad Sci USA* 98, 2899-2904
29. Cabanes-Macheteau, M., Fitchette-Laine, A. C., Loutelier-Bourhis, C., Lange, C., Vine, N. D., Ma, J. K., Lerouge, P., and Faye, L. (1999) *Glycobiology* 9,
30. Lerouge P, C.-M. M., Rayon C, Fischette-Laine A C, Gomord V, Faye L. (1998) *Plant Mol. Biol.* 38, 31-48

31. Dwek R A, B. T., Platt F M, Zitzmann N. (2002) *Nat Rev Drug Discov.* 1, 65-75

32. Ko, K., Tekoah, Y., Rudd, P. M., Harvey, D. J., Dwek, R. A., Spitsin, S., Hanlon, C. A., Rupprecht, C., Dietzschold, B., Golovkin, M., and Koprowski, H. (2003) *Proc Natl Acad Sci USA* 100, 8013-8018

33. Neuhaus, J. M., Rogers, J. C. (1998) *Plant Mol Biol* 38, 127-144

34. Frigerio, L., Pastres, A., Prada, A., and Vitale, A. (2001) *Plant Cell* 13, 35. Frigerio, L., Vine, N. D., Pedrazzini, E., Hein, M. B., Wang, F., Ma, J. K., and Vitale, A. (2000) *Plant Physiol* 123, 1483-1494

36. Hadlington J L, D. J. (2000) *Curr Opin Plant Biol.* 3, 461-468.

37. Okamoto, T., Shimada, T., Hara-Nishimura, I., Nishimura, M., and Minamikawa, T. (2003) *Plant Physiol.* 132, 1892-1900

38. Hellens, R., Edwards, E A., Leyland, N. R., Bean, S., Mullineaux, P. M. (2000) *Plant Mol Biol* 42, 819-832

39. den Dulk-Ras, A., Hooykaas, P. J. (1995) *Methods Mol. Biol.* 55, 63-72

40. Wurtele, E. S., Bulka, K. (1989) *Plant Sci* 61, 253-262

41. Laemmli, U. K. (1970) *Nature reviews* 227, 680-685

42. Bradford, M. M. (1976) *Anal Biochem* 72, 248-254

43. Aalberse, R. C., and Schuurman, J. (2002) *Immunology* 105, 9-19

44. Manohar V, H. T. (1992) *Trends Biotechnol.* 10, 305-309

45. Hiatt A, M. J. (1993) *Int Rev Immunol* 10, 139-152

46. Khoudi, H., Laberge, S., Ferullo, J. M., Bazin, R., Darveau, A., Castonguay, Y., Allard, G., Lemieux, R., and Vezina, L. P. (1999) *Biotechnol Bioeng* 64, 135-143

47. Chargelegue, D., Vine, N. D., van Dolleweerd, C. J., Drake, P. M., and Ma, J. K. (2000) *Transgenic Res* 9, 187-194

48. Pollock D P, K. J., Birck-Wilson E, Williams J L, Echelard Y, Meade H M. (1999) *J Immunol Methods* 231, 147-157

49. Thompson J E, V. T., Williams A J, Wilton J, Johnson K S, Bacon L, Green J A, Field R, Ruddock S, Martins M, Pope A R, Tempest P R, Jackson R H. (1999) *J Immunol Methods* 227, 17-29

50. Rossmann C, S. N., Allen G, Gewert D. (1996) *Protein Expr Purif.* 7,

51. Bardor, M., Faveeuw, C., Fitchette, A.-C., Gilbert, D., Galas, L., Trottein, F., Faye, L., and Lerouge, P. (2003) *Glycobiology* 13, 427-434

---

What is claimed is:

1. A carrot root host cell producing a human IgG4 antibody, comprising a recombinant polynucleotide encoding the human IgG4 antibody, wherein said recombinant polynucleotide comprises a human heavy chain coding sequence as set forth in SEQ ID NO: 9 and a human light chain coding sequence as set forth in SEQ ID NO: 5.

2. The carrot root host cell according to claim 1, wherein said host cell is transfected or transformed with a prokaryotic cell.

3. The carrot root host cell according to claim 2, wherein said prokaryotic cell is a bacterial cell, preferably an *Agrobacterium tumefaciens* cell.

4. The carrot root host cell according to claim 3, wherein said recombinant polynucleotide further comprises a promoter that is functional in plant cells, wherein said promoter is operably linked to said recombinant polynucloetide.

5. The carrot root host cell according to claim 4, wherein said recombinant polynucleotide further comprises a terminator that is functional in plant cells, wherein said terminator is operably linked to said recombinant polynucleotide.

6. The carrot root host cell according to claim 5, wherein said recombinant polynucleotide optionally further comprises additional control, promoting and regulatory elements and/or selectable markers, wherein said regulatory elements are operably linked to said recombinant polynucleotide.

7. A method of producing a recombinant antibody, the method comprising:
   (a) generating a suspension culture comprising carrot root cells being genetically modified with a nucleic acid construct comprising the polynucleotides as set forth in SEQ ID NO: 5 and SEQ ID NO: 9 and expressing the recombinant antibody; and optionally
   (b) recovering the recombinant antibody from said suspension culture thereby producing the recombinant antibody;
   wherein said carrot root cells express fully assembled, functional human IgG4 antibodies, wherein said antibodies comprise fully processed human natural light and heavy chain amino acid sequence, and wherein said antibodies have a higher level of binding affinity for an antigen than a corresponding antibody produced in mammalian cell culture.

8. The method of claim 7, further comprising:
purifying said antibodies following culturing.

* * * * *

SEQUENCE LISTING

<160> NUMBER OF SEQ ID NOS: 28

<210> SEQ ID NO 1
<211> LENGTH: 1413
<212> TYPE: DNA
<213> ORGANISM: Artificial sequence
<220> FEATURE:
<223> OTHER INFORMATION: Synthetic gene coding for an Ab heavy chain

<400> SEQUENCE: 1

```
gtcgacatgg actggacctg gaggattctg ttcctcgttg ctgctgcaac aggtgctcat      60
tctcaggttc aacttgtgca gtcaggttct gagttgaaga agccaggagc ctcagtcaaa     120
atttcttgta aggctagtgg ttacactttc accaactacg gaatgaactg ggttaggcaa     180
gcacctggac agggtcttca gtggatggga tggatcaaca ctgattctgg tgagtcaaca     240
tacgctgagg agttcaaggg aaggttcgtg ttctctctcg acacctcagt caacaccgca     300
taccttcaga tcacctcttt gactgctgag gacaccggta tgtacttctg cgtgagggtc     360
ggctatgatg ccctcgacta ctggggtcag ggaactctgg tgacagtgag ttctgcttca     420
actaagggtc catcagtgtt ccctctcgct ccatctagta agtctacatc aggtggaact     480
gctgcccttg gatgccttgt caaggactac ttccctgagc cagttacagt tcatggaac      540 agtggagcct tgacctctgg tgtgcacact tttcctgctg tcctgcaatc aagtggtctc     600
tactctttgt cttctgttgt tactgtgcca tcatcatctc tcggaaccca aacatatatc     660
tgtaatgtca accataagcc ttcaaatacc aaggttgaca agaaggtgga gcctaagtct     720
tgcgacaaga cccacacctg cccaccttgt cctgctccag agttccttgg aggtccttct     780
gtgtttctct tcccacctaa gccaaaagat acactgatga tcagtagaac acctgaagtt     840
acctgcgttg tggtcgatgt ttctcacgag gacccagaag tgaagttcaa ctggtacgtc     900
gatggagttg aggtgcataa cgcaaagaca aagcctagag aggaacagta caattcaacc     960
tacagagttg tgtctgtctt gaccgttctt caccaagatt ggcttaacgg taaggagtat    1020
aagtgtaagg tttctaacaa ggctttgcca gccccatcg agaaaactat ctcaaaggca    1080
```

```
aagggacagc ctagggaacc acaggtgtac accttgccac cttctaggga ggaaatgacc      1140
aagaaccaag tctcactcac ttgccttgtt aaaggtttct accccttcaga cattgctgtt     1200 gagtgggaat ccaacggtca accagagaat aactacaaga ctacaccacc tgtgctggac     1260
tcagatggat ctttcttttt gtattctaag ctgacagtcg ataagagtag atggcagcaa     1320
ggtaatgtgt tttcatgttc tgtcatgcat gaggctctcc acaatcatta cactcagaaa     1380
tctctctcat tgtctcccgg aaagtaagaa ttc                                  1413
```

<210> SEQ ID NO 2
<211> LENGTH: 1356
<212> TYPE: DNA
<213> ORGANISM: Artificial sequence
<220> FEATURE:
<223> OTHER INFORMATION: Synthetic gene coding for an Ab heavy chain fused to Apo signal

<400> SEQUENCE: 2

```
gaattccagg ttcaacttgt gcagtcaggt tctgagttga agaagccagg agcctcagtc       60
aaaatttctt gtaaggctag tggttacact ttcaccaact acggaatgaa ctgggttagg      120
caagcacctg gacagggtct tcagtggatg ggatggatca cactgattc tggtgagtca       180 acatacgctg aggagttcaa gggaaggttc gtgttctctc tcgacacctc agtcaacacc     240
gcataccttc agatcaccct ctttgactgct gaggacaccg gtatgtactt ctgcgtgagg    300
gtcggctatg atgccctcga ctactgggg cagggaactc tggtgacagt gagttctgct     360
tcaactaagg gtccatcagt gttccctctc gctccatcta gtaagtctac atcaggtgga    420
actgctgccc ttggatgcct tgtcaaggac tacttccctg agccagttac agtttcatgg   480
aacagtggag ccttgacctc tggtgtgcac acttttcctg ctgtcctgca atcaagtggt   540
ctctactctt tgtcttctgt tgttactgtg ccatcatcat ctctcggaac ccaaacatat    600
atctgtaatg tcaaccataa gccttcaaat accaaggttg acaagaaggt ggagcctaag   660
tcttgcgaca agacccacac ctgcccacct tgtcctgctc cagagttcct tggaggtcct   720
tctgtgtttc cttcccacc taagccaaaa gatacactga tgatcagtag aacacctgaa   780
gttacctgcg ttgtggtcga tgtttctcac gaggacccag aagtgaagtt caactggtac   840
gtcgatggag ttgaggtgca taacgcaaag acaaagccta gagaggaaca gtacaattca   900
acctacagag ttgtgtctgt cttgaccgtt cttcaccaag attggcttaa cggtaaggag   960
tataagtgta aggtttctaa caaggctttg ccagccccca tcgagaaaac tatctcaaag  1020
gcaaagggac agcctaggga accacaggtg tacaccttgc caccttctag ggaggaaatg  1080
accaagaacc aagtctcact cacttgcctt gttaaaggtt ctacccttc agacattgct   1140 gttgagtggg aatccaacgg tcaaccagag aataactaca agactacacc acctgtgctg  1200
gactcagatg gatctttctt tttgtattct aagctgacag tcgataagag tagatggcag  1260
caaggtaatg tgttttcatg ttctgtcatg catgaggctc tccacaatca ttacactcag  1320
aaatctctct cattgtctcc cggaaagtaa gtcgac                            1356
```

<210> SEQ ID NO 3
<211> LENGTH: 1352
<212> TYPE: DNA
<213> ORGANISM: Artificial sequence
<220> FEATURE:
<223> OTHER INFORMATION: Synthetic gene coding for an Ab heavy chain fused to ER signal

<400> SEQUENCE: 3

```
gaattccagg ttcaacttgt gcagtcaggt tctgagttga agaagccagg agcctcagtc      60
aaaatttctt gtaaggctag tggttacact ttcaccaact acggaatgaa ctgggttagg     120
caagcacctg gacagggtct tcagtggatg ggatggatca acactgattc tggtgagtca     180
acatacgctg aggagttcaa gggaaggttc gtgttctctc tcgacacctc agtcaacacc     240
gcataccttc agatcaccct ctttgactgc tgaggacaccg gtatgtactt ctgcgtgagg     300
gtcggctatg atgccctcga ctactggggt cagggaactc tggtgacagt gagttctgct     360
tcaactaagg gtccatcagt gttccctctc gctccatcta gtaagtctac atcaggtgga     420
actgctgccc ttggatgcct tgtcaaggac tacttccctg agccagttac agtttcatgg     480
aacagtggag ccttgacctc tggtgtgcac acttttcctg ctgtcctgca atcaagtggt     540
ctctactctt tgtcttctgt tgttactgtg ccatcatcat ctctcggaac ccaaacatat     600
atctgtaatg tcaaccataa gccttcaaat accaaggttg acaagaaggt ggagcctaag     660
tcttgcgaca gacccacac ctgcccacct tgtcctgctc cagagttcct tggaggtcct     720
tctgtgtttc tcttcccacc taagccaaaa gatacactga tgatcagtag aacacctgaa     780
gttacctgcg ttgtggtcga tgtttctcac gaggacccag aagtgaagtt caactggtac     840
gtcgatggag ttgaggtgca taacgcaaag acaaagccta gagaggaaca gtacaattca     900
acctacagag ttgtgtctgt cttgaccgtt cttcaccaag attggcttaa cggtaaggag     960
tataagtgta aggtttctaa caaggctttg ccagccccca tcgagaaaac tatctcaaag    1020
gcaaagggac agcctaggga accacaggtg tacaccttgc caccttctag ggaggaaatg    1080
accaagaacc aagtctcact cacttgcctt gttaaaggtt ctaccccttc agacattgct    1140
gttgagtggg aatccaacgg tcaaccagag aataactaca agactacacc acctgtgctg    1200
gactcagatg gatctttctt tttgtattct aagctgacag tcgataagag tagatggcag    1260
caaggtaatg tgttttcatg ttctgtcatg catgaggctc tccacaatca ttacactcag    1320
aaatctctct cattgtctcc cggaaagtcg ac                                   1352

<210> SEQ ID NO 4
<211> LENGTH: 1377
<212> TYPE: DNA
<213> ORGANISM: Artificial sequence
<220> FEATURE:
<223> OTHER INFORMATION: Synthetic gene coding for an Ab heavy chain
      fused to Vac signal

<400> SEQUENCE: 4
gaattccagg ttcaacttgt gcagtcaggt tctgagttga agaagccagg agcctcagtc      60
aaaatttctt gtaaggctag tggttacact ttcaccaact acggaatgaa ctgggttagg     120
caagcacctg gacagggtct tcagtggatg ggatggatca acactgattc tggtgagtca     180
acatacgctg aggagttcaa gggaaggttc gtgttctctc tcgacacctc agtcaacacc     240
gcataccttc agatcaccct ctttgactgc tgaggacaccg gtatgtactt ctgcgtgagg     300
gtcggctatg atgccctcga ctactggggt cagggaactc tggtgacagt gagttctgct     360
tcaactaagg gtccatcagt gttccctctc gctccatcta gtaagtctac atcaggtgga     420
actgctgccc ttggatgcct tgtcaaggac tacttccctg agccagttac agtttcatgg     480
aacagtggag ccttgacctc tggtgtgcac acttttcctg ctgtcctgca atcaagtggt     540
ctctactctt tgtcttctgt tgttactgtg ccatcatcat ctctcggaac ccaaacatat     600
atctgtaatg tcaaccataa gccttcaaat accaaggttg acaagaaggt ggagcctaag     660
```

```
tcttgcgaca agacccacac ctgcccacct tgtcctgctc cagagttcct tggaggtcct    720
tctgtgtttc tcttcccacc taagccaaaa gatacactga tgatcagtag aacacctgaa    780
gttacctgcg ttgtggtcga tgtttctcac gaggacccag aagtgaagtt caactggtac    840
gtcgatggag ttgaggtgca taacgcaaag acaaagccta gagaggaaca gtacaattca    900
acctacagag ttgtgtctgt cttgaccgtt cttcaccaag attggcttaa cggtaaggag    960
tataagtgta aggtttctaa caaggctttg ccagccccca tcgagaaaac tatctcaaag   1020
gcaaagggac agcctaggga accacaggtg tacaccttgc caccttctag ggaggaaatg   1080
accaagaacc aagtctcact cacttgcctt gttaaaggtt ctacccttc agacattgct    1140 gttgagtggg aatccaacgg tcaaccagag aataactaca agactacacc acctgtgctg   1200
gactcagatg gatctttctt tttgtattct aagctgacag tcgataagag tagatggcag   1260
caaggtaatg tgttttcatg ttctgtcatg catgaggctc tccacaatca ttacactcag   1320
aaatctctct cattgtctcc cggaaaaggc cttttagtcg atactatgta agtcgac      1377

<210> SEQ ID NO 5
<211> LENGTH: 720
<212> TYPE: DNA
<213> ORGANISM: Artificial sequence
<220> FEATURE:
<223> OTHER INFORMATION: Synthetic gene coding for an Ab light chain

<400> SEQUENCE: 5
gtcgacatgg atatgagagt tccagctcag cttttgggac tcttgctctt gtggctccca     60
ggtgctaagt gtgagattgt tcttactcaa tctccttctt cactgtcagc atccgtggga    120
gatagggtta caattacttg ctctgccaga tcatccgtct cttatatgca ttggtttcag    180
cagaagcctg gtaaagctcc aaagctgtgg atttacagga cttcaaatct cgcttctgga    240
gtgccttcca gattctcagg atctggttct ggaacatcat attgtcttac tattaattct    300
ttgcagccag aagattttgc aacctattac tgccaacaga ggtcttcatt ccctcttact    360
ttcggcggag gtacaaaatt ggagatcaag agaactgttg ctgccccatc cgttttcatc    420
tttcctccat ctgacgaaca actcaagtca ggaacagcat cagtggtttg tctgcttaat    480 aactttttacc caagagaggc taaagttcag tggaaggtgg ataatgcttt gcaatccggt    540
aactctcagg aatcagtcac cgagcaggat tcaaagatt ctacttattc actttcctct    600
acacttactc tttctaaggc agactacgaa aagcataaag tttatgcctg tgaggtgacc    660
catcaaggct gtcctctcc tgtcactaag tcattcaata ggggagaatg ctaagaattc    720

<210> SEQ ID NO 6
<211> LENGTH: 654
<212> TYPE: DNA
<213> ORGANISM: Artificial sequence
<220> FEATURE:
<223> OTHER INFORMATION: Synthetic gene coding for an Ab light chain
     fused to Apo signal

<400> SEQUENCE: 6
gaattcgaga ttgttcttac tcaatctcct tcttcactgt cagcatccgt gggagatagg     60
gttacaatta cttgctctgc cagatcatcc gtctcttata tgcattggtt tcagcagaag    120
cctggtaaag ctccaaagct gtggatttac aggacttcaa atctcgcttc tggagtgcct    180
tccagattct caggatctgg ttctggaaca tcatattgtc ttactattaa ttctttgcag    240
ccagaagatt ttgcaaccta ttactgccaa cagaggtctt cattccctct tacttcggc    300 ggaggtacaa aattggagat caagagaact gttgctgccc catccgtttt catcttcct    360
```

```
ccatctgacg aacaactcaa gtcaggaaca gcatcagtgg tttgtctgct taataacttt    420
tacccaagag aggctaaagt tcagtggaag gtggataatg ctttgcaatc cggtaactct    480
caggaatcag tcaccgagca ggattcaaaa gattctactt attcactttc ctctacactt    540
actctttcta aggcagacta cgaaaagcat aaagtttatg cctgtgaggt gacccatcaa    600
ggcttgtcct ctcctgtcac taagtcattc aataggggag aatgctaagt cgac          654
```

<210> SEQ ID NO 7
<211> LENGTH: 650
<212> TYPE: DNA
<213> ORGANISM: Artificial sequence
<220> FEATURE:
<223> OTHER INFORMATION: Synthetic gene coding for an Ab light chain
      fused to ER signal

<400> SEQUENCE: 7

```
gaattcgaga ttgttcttac tcaatctcct tcttcactgt cagcatccgt gggagatagg     60
gttacaatta cttgctctgc cagatcatcc gtctcttata tgcattggtt tcagcagaag    120
cctggtaaag ctccaaagct gtggatttac aggacttcaa atctcgcttc tggagtgcct    180
tccagattct caggatctgg ttctggaaca tcatattgtc ttactattaa ttctttgcag    240
ccagaagatt ttgcaaccta ttactgccaa cagaggtctt cattccctct tactttcggc    300
ggaggtacaa aattggagat caagagaact gttgctgccc catccgtttt catctttcct    360
ccatctgacg aacaactcaa gtcaggaaca gcatcagtgg tttgtctgct taataacttt    420
tacccaagag aggctaaagt tcagtggaag gtggataatg ctttgcaatc cggtaactct    480
caggaatcag tcaccgagca ggattcaaaa gattctactt attcactttc ctctacactt    540
actctttcta aggcagacta cgaaaagcat aaagtttatg cctgtgaggt gacccatcaa    600
ggcttgtcct ctcctgtcac taagtcattc aataggggag aatgctcgag               650
```

<210> SEQ ID NO 8
<211> LENGTH: 675
<212> TYPE: DNA
<213> ORGANISM: Artificial sequence
<220> FEATURE:
<223> OTHER INFORMATION: Synthetic gene coding for an Ab light chain
      fused to Vac signal

<400> SEQUENCE: 8

```
gaattcgaga ttgttcttac tcaatctcct tcttcactgt cagcatccgt gggagatagg     60
gttacaatta cttgctctgc cagatcatcc gtctcttata tgcattggtt tcagcagaag    120
cctggtaaag ctccaaagct gtggatttac aggacttcaa atctcgcttc tggagtgcct    180
tccagattct caggatctgg ttctggaaca tcatattgtc ttactattaa ttctttgcag    240
ccagaagatt ttgcaaccta ttactgccaa cagaggtctt cattccctct tactttcggc    300
ggaggtacaa aattggagat caagagaact gttgctgccc catccgtttt catctttcct    360
ccatctgacg aacaactcaa gtcaggaaca gcatcagtgg tttgtctgct taataacttt    420
tacccaagag aggctaaagt tcagtggaag gtggataatg ctttgcaatc cggtaactct    480
caggaatcag tcaccgagca ggattcaaaa gattctactt attcactttc ctctacactt    540
actctttcta aggcagacta cgaaaagcat aaagtttatg cctgtgaggt gacccatcaa    600
ggcttgtcct ctcctgtcac taagtcattc aataggggag aatgcggcct tttagtcgat    660
actatgtaag tcgac                                                     675
```

```
<210> SEQ ID NO 9
<211> LENGTH: 1404
<212> TYPE: DNA
<213> ORGANISM: Artificial sequence
<220> FEATURE:
<223> OTHER INFORMATION: Synthetic gene coding for an Ab heavy chain

<400> SEQUENCE: 9
gtcgacatgg actggacctg gagaatcctg ttcctcgttg ctgctgcaac aggtgctcat      60
tctcaggttc aacttgtgca gtcaggttct gagttgaaga agccaggagc ctcagtcaaa     120
atttcttgta aggctagtgg ttacactttc accaactacg gaatgaactg ggttaggcaa     180
gcacctggac agggtcttca gtggatggga tggatcaaca ctgattctgg tgagtcaaca     240
tacgctgagg agttcaaggg aaggttcgtg ttctctctcg acacctcagt caacaccgca     300
taccttcaga tcacctcttt gactgctgag gacaccggta tgtacttctg cgtgagggtc     360
ggctatgatg ccctcgacta ctggggtcag ggaactctgg tgacagtgag ttctgcttca     420
actaagggtc catcagtgtt ccctctcgct ccatgtagta ggtctacatc agagtctact     480
gcagcccttg gatgccttgt caaggactac ttccctgagc cagttacagt tcatggaac      540 agtggagcct tgacctctgg tgtgcacact tttcctgctg tcctgcaatc aagtggtctc     600
tactctttgt cttctgttgt tactgtgcca tcatcatctc tcggaaccaa aacatatact     660
tgtaatgtcg atcataagcc ttcaaatacc aaggttgaca gagggtgga gtcaaagtat     720 ggtccacctt gcccaagttg tcctgctcca gagttccttg aggtccttc tgtgtttctc     780 ttcccaccta agccaaaaga tacactgatg atcagtagaa cacctgaagt tacctgcgtt     840
gtggtcgatg tttctcagga ggacccagaa gtgcagttca actggtacgt cgatggagtt     900
gaggtgcata acgcaaagac aaagcctaga gaggaacagt ttaattcaac ctacagagtt     960
gtgtctgtct tgaccgttct tcaccaagat tggcttaacg gtaaggagta taagtgtaag    1020
gtttctaaca agggattgcc atcatctatc gagaaaacta tctcaaaggc aaagggacag    1080
cctagggaac cacaggtgta caccttgcca ccttctcaag aggaaatgac caagaaccaa    1140
gtctcactca cttgccttgt taaaggtttc tacccttcag acattgctgt tgagtgggaa    1200
tccaacggtc aaccagagaa taactacaag actacaccac ctgtgctgga ctcagatgga    1260
tcttctcttt tgtattctag gctgacagtc gataagagta gatggcagga aggtaatgtg    1320
ttttcatgtt ctgtcatgca tgaggctctc cacaatcatt acactcagaa atctctctca    1380
ttgtctcttg gaaagtaaga attc                                           1404

<210> SEQ ID NO 10
<211> LENGTH: 1347
<212> TYPE: DNA
<213> ORGANISM: Artificial sequence
<220> FEATURE:
<223> OTHER INFORMATION: Synthetic gene coding for an Ab heavy chain
      fused to Apo signal

<400> SEQUENCE: 10
gaattccagg ttcaacttgt gcagtcaggt tctgagttga agaagccagg agcctcagtc      60
aaaatttctt gtaaggctag tggttacact ttcaccaact acggaatgaa ctgggttagg     120
caagcacctg gacagggtct tcagtggatg ggatggatca cactgattc tggtgagtca     180 acatacgctg aggagttcaa gggaaggttc gtgttctctc tcgacacctc agtcaacacc     240
gcataccttc agatcacctc tttgactgct gaggacaccg gtatgtactt ctgcgtgagg     300
gtcggctatg atgccctcga ctactggggt cagggaactc tggtgacagt gagttctgct     360
```

```
tcaactaagg gtccatcagt gttccctctc gctccatgta gtaggtctac atcagagtct    420
actgctgccc ttggatgcct tgtcaaggac tacttccctg agccagttac agtttcatgg    480
aacagtggag ccttgacctc tggtgtgcac acttttcctg ctgtcctgca atcaagtggt    540
ctctactctt tgtcttctgt tgttactgtg ccatcatcat ctctcggaac caaaacatat    600
acttgtaatg tcgatcataa gccttcaaat accaaggttg acaagagggt ggagtcaaag    660
tatggtccac cttgcccaag ttgtcctgct ccagagttcc ttggaggtcc ttctgtgttt    720
ctcttcccac ctaagccaaa agatacactg atgatcagta gaacacctga gttacctgc     780 gttgtggtcg atgtttctca ggaggaccca gaagtgcagt tcaactggta cgtcgatgga    840
gttgaggtgc ataacgcaaa gacaaagcct agagaggaac agtttaattc aacctacaga    900
gttgtgtctg tcttgaccgt tcttcaccaa gattggctta acggtaagga gtataagtgt    960
aaggtttcta acaagggatt gccatcatct atcgagaaaa ctatctcaaa ggcaaaggga   1020
cagcctaggg aaccacaggt gtacaccttg ccaccttctc aagaggaaat gaccaagaac   1080
caagtctcac tcacttgcct tgttaaaggt ttctacccct tcagacattgc tgttgagtgg   1140 gaatccaacg gtcaaccaga gaataactac aagactacac cacctgtgct ggactcagat   1200
ggatctttct ttttgtattc taggctgaca gtcgataaga gtagatggca ggaaggtaat   1260
gtgttttcat gttctgtcat gcatgaggct ctccacaatc attacactca gaaatctctc   1320
tcattgtctc ttggaaagta agtcgac                                       1347
```

<210> SEQ ID NO 11
<211> LENGTH: 1347
<212> TYPE: DNA
<213> ORGANISM: Artificial sequence
<220> FEATURE:
<223> OTHER INFORMATION: Synthetic gene coding for an Ab heavy chain fused to ER signal

<400> SEQUENCE: 11

```
gaattccagg ttcaacttgt gcagtcaggt tctgagttga agaagccagg agcctcagtc     60
aaaatttctt gtaaggctag tggttacact ttcaccaact acggaatgaa ctgggttagg    120
caagcacctg gacagggtct tcagtggatg ggatggatca cactgattc tggtgagtca     180 acatacgctg aggagttcaa gggaaggttc gtgttctctc tcgacacctc agtcaacacc    240
gcataccttc agatcaccctc tttgactgct gaggacaccg gtatgtactt ctgcgtgagg    300
gtcggctatg atgccctcga ctactgggt caggaactc tggtgacagt gagttctgct      360
tcaactaagg gtccatcagt gttccctctc gctccatgta gtaggtctac atcagagtct    420
actgctgccc ttggatgcct tgtcaaggac tacttccctg agccagttac agtttcatgg    480
aacagtggag ccttgacctc tggtgtgcac acttttcctg ctgtcctgca atcaagtggt    540
ctctactctt tgtcttctgt tgttactgtg ccatcatcat ctctcggaac caaaacatat    600
acttgtaatg tcgatcataa gccttcaaat accaaggttg acaagagggt ggagtcaaag    660
tatggtccac cttgcccaag ttgtcctgct ccagagttcc ttggaggtcc ttctgtgttt    720
ctcttcccac ctaagccaaa agatacactg atgatcagta gaacacctga gttacctgc     780 gttgtggtcg atgtttctca ggaggaccca gaagtgcagt tcaactggta cgtcgatgga    840
gttgaggtgc ataacgcaaa gacaaagcct agagaggaac agtttaattc aacctacaga    900
gttgtgtctg tcttgaccgt tcttcaccaa gattggctta acggtaagga gtataagtgt    960
aaggtttcta acaagggatt gccatcatct atcgagaaaa ctatctcaaa ggcaaaggga   1020
cagcctaggg aaccacaggt gtacaccttg ccaccttctc aagaggaaat gaccaagaac   1080
```

```
caagtctcac tcacttgcct tgttaaaggt ttctacccct cagacattgc tgttgagtgg    1140
gaatccaacg gtcaaccaga gaataactac aagactacac cacctgtgct ggactcagat    1200
ggatctttct ttttgtattc taggctgaca gtcgataaga gtagatggca ggaaggtaat    1260
gtgttttcat gttctgtcat gcatgaggct ctccacaatc attacactca gaaatctctc    1320
tcattgtctc ttggaaagtc gaccaag                                         1347
```

<210> SEQ ID NO 12
<211> LENGTH: 1368
<212> TYPE: DNA
<213> ORGANISM: Artificial sequence
<220> FEATURE:
<223> OTHER INFORMATION: Synthetic gene coding for an Ab heavy chain
      fused to Vac signal

<400> SEQUENCE: 12

```
gaattccagg ttcaacttgt gcagtcaggt tctgagttga agaagccagg agcctcagtc      60
aaaatttctt gtaaggctag tggttacact ttcaccaact acggaatgaa ctgggttagg     120
caagcacctg gacagggtct tcagtggatg ggatggatca acactgattc tggtgagtca     180
acatacgctg aggagttcaa gggaaggttc gtgttctctc tcgacacctc agtcaacacc     240
gcataccttc agatcaccct ctttgactgc gaggacaccg gtatgtactt ctgcgtgagg     300
gtcggctatg atgccctcga ctactggggt cagggaactc tggtgacagt gagttctgct     360
tcaactaagg gtccatcagt gttccctctc gctccatgta gtaggtctac atcagagtct     420
actgctgccc ttggatgcct tgtcaaggac tacttccctg agccagttac agtttcatgg     480
aacagtggag ccttgacctc tggtgtgcac acttttcctg ctgtcctgca atcaagtggt     540
ctctactctt tgtcttctgt tgttactgtg ccatcatcat ctctcggaac caaaacatat     600
acttgtaatg tcgatcataa gccttcaaat accaaggttg acaagagggt ggagtcaaag     660
tatggtccac cttgcccaag ttgtcctgct ccagagttcc ttggaggtcc ttctgtgttt     720
ctcttcccac ctaagccaaa agatacactg atgatcagta aacacctga gttacctgc      780 gttgtggtcg atgtttctca ggaggaccca gaagtgcagt tcaactggta cgtcgatgga     840
gttgaggtgc ataacgcaaa gacaaagcct agagaggaac agtttaattc aacctacaga     900
gttgtgtctg tcttgaccgt tcttcaccaa gattggctaa acggtaagga gtataagtgt     960
aaggtttcta caagggatt gccatcatct atcgagaaaa ctatctcaaa ggcaaaggga    1020
cagcctaggg aaccacaggt gtacaccttg ccaccttctc aagaggaaat gaccaagaac    1080
caagtctcac tcacttgcct tgttaaaggt ttctacccct cagacattgc tgttgagtgg    1140
gaatccaacg gtcaaccaga gaataactac aagactacac cacctgtgct ggactcagat    1200
ggatctttct ttttgtattc taggctgaca gtcgataaga gtagatggca ggaaggtaat    1260
gtgttttcat gttctgtcat gcatgaggct ctccacaatc attacactca gaaatctctc    1320
tcattgtctc ttggaaaagg ccttttagtc gatactatgt aagtcgac                 1368
```

<210> SEQ ID NO 13
<211> LENGTH: 7
<212> TYPE: PRT
<213> ORGANISM: Artificial sequence
<220> FEATURE:
<223> OTHER INFORMATION: Vacuolar soting pepide

<400> SEQUENCE: 13

```
Gly Leu Leu Val Asp Thr Met
1               5
```

<210> SEQ ID NO 14
<211> LENGTH: 66
<212> TYPE: DNA
<213> ORGANISM: Artificial sequence
<220> FEATURE:
<223> OTHER INFORMATION: Nucleic acid sequence coding for the ER
      targeting sequence from endochitinase and an ER retention signal

<400> SEQUENCE: 14

```
atgaagacta atctttttct ctttctcatc ttttcacttc tcctatcatt atcctcggcc      60
gaattc                                                                66
```

<210> SEQ ID NO 15
<211> LENGTH: 4560
<212> TYPE: DNA
<213> ORGANISM: Artificial sequence
<220> FEATURE:
<223> OTHER INFORMATION: pG1KD210.BAT-RHcRKd construct sequence

<400> SEQUENCE: 15

```
tccttgacac gcgtctcggg aagcttgccg ccaccatgga catgagggtc cccgctcagc      60
tcctggggct cctgctgctc tggctcccag gtgccaaatg tgaaattgtg ttgacgcagt     120
ctccatcctc cctgtctgca tctgtaggag acagagtcac catcacttgc agtgccaggt     180
caagtgtaag ttacatgcac tggttccagc agaaaccagg gaaagcccct aagctctgga     240
tctataggac atccaacctg gcttctgggg tcccatctag attcagcggc agtggatctg     300
ggacatctta ctgtctcacc atcaacagcc tgcagcctga agattttgca acttactatt     360
gccagcaaag gagtagtttc ccactcacgt tcggcggagg gaccaagctg gagatcaaac     420
gtgagtggat ccatctggga taagcatgct gttttctgtc tgtccctaac atgcctgtg      480 attatgcgca acaacacac ccaagggcag aactttgtta cttaaacacc atcctgtttg     540 cttcttttcct caggaactgt ggctgcacca tctgtcttca tcttcccgcc atctgatgag     600
cagttgaaat ctggaactgc ctctgttgtg tgcctgctga ataacttcta tcccagagag     660
gccaaagtac agtggaaggt ggataacgcc ctccaatcgg gtaactccca ggagagtgtc     720
acagagcagg acagcaagga cagcacctac agcctcagca gcaccctgac gctgagcaaa     780
gcagactacg agaaacacaa agtctacgcc tgcgaagtca cccatcaggg cctgagctcg     840
cccgtcacaa agagcttcaa caggggagag tgttagaggg agaagtgccc ccacctgctc     900
ctcagttcca gctgacccc ctcccatcct ttggcctctg accctttttc cacaggggac     960 ctaccccctat tgcggtcctc cagctcatct ttcacctcac cccctcctc ctccttggct    1020 ttaattatgc taatgttgga ggagaatgaa taaataaagt gaatctttgc acctgtggtg    1080
gatctaataa aagatattta ttttcattag atatgtgtgt tggttttttg tgtgcagtgc    1140
ctctatctgg aggccaggta gggctggcct tgggggaggg ggaggccaga atgactccaa    1200
gagctacagg aaggcaggtc agagaccca ctggacaaac agtggctgga ctctgcacca    1260
taacacacaa tcaacagggg agtgagctgg aaatttgcta cgaattcta ttaatagtaa    1320 tcaattacgg ggtcattagt tcatagccca tatatggagt tccgcgttac ataacttacg    1380
gtaaatggcc cgcctggctg accgcccaac gaccccgcc cattgacgtc aataatgacg    1440
tatgttccca tagtaacgcc aatagggact ttccattgac gtcaatgggt ggagtattta    1500
cggtaaactg cccacttggc agtacatcaa gtgtatcata tgccaagtac gccccctatt    1560
gacgtcaatg acggtaaatg gcccgcctgg cattatgccc agtacatgac cttatgggac    1620
```

```
tttcctactt ggcagtacat ctacgtatta gtcatcgcta ttaccatggt gatgcggttt      1680
tggcagtaca tcaatgggcg tggatagcgg tttgactcac ggggatttcc aagtctccac      1740
cccattgacg tcaatgggag tttgttttgg caccaaaatc aacgggactt tccaaaatgt      1800
cgtaacaact ccgccccatt gacgcaaatg ggcggtaggc gtgtacggtg ggaggtctat      1860
ataagcagag ctcgtttagt gaaccgtcag atcgcctgga gacgccatcc acgctgtttt      1920
gacctccata aagacaccg ggaccgatcc agcctccgcg gccgggaacg gtgcattgga       1980
acgcggattc cccgtgccaa gagtgacgta agtaccgcct atagagtcta taggcccacc      2040
cccttggctt cttatgcatg ctatactgtt tttggcttgg ggtctataca ccccgcttc       2100 ctcatgttat aggtgatggt atagcttagc ctataggtgt gggttattga ccattattga      2160
ccactcccct attggtgacg atactttcca ttactaatcc ataacatggc tctttgccac      2220
aactctcttt attggctata tgccaataca ctgtccttca gagactgaca cggactctgt      2280 attttacag gatggggtct catttattat ttacaaattc acatatacaa caccaccgtc       2340
cccagtgccc gcagttttta ttaaacataa cgtgggatct ccacgcgaat ctcgggtacg      2400
tgttccggac atgggctctt ctccggtagc ggcggagctt ctacatccga gccctgctcc      2460
catgcctcca gcgactcatg gtcgctcggc agctccttgc tcctaacagt ggaggccaga      2520
cttaggcaca gcacgatgcc caccaccacc agtgtgccgc acaaggccgt ggcggtaggg      2580
tatgtgtctg aaaatgagct cggggagcgg gcttgcaccg ctgacgcatt tggaagactt      2640
aaggcagcgg cagaagaaga tgcaggcagc tgagttgttg tgttctgata agagtcagag      2700
gtaactcccg ttgcggtgct gttaacggtg gagggcagtg tagtctgagc agtactcgtt      2760
gctgccgcgc gcgccaccag acataatagc tgacagacta acagactgtt cctttccatg      2820
ggtcttttct gcagtcaccg tccttgacac gcgtctcggg aagcttgccg ccaccatgga      2880
ctggacctgg aggatcctct tcttggtggc agcagcaaca ggtgcccact cccaggtgca      2940
gctggtgcaa tctgggtctg agcttaagaa gcctggggcc tcagtgaaga tctcctgcaa      3000
ggcttctgga tatactttca caaactatgg aatgaactgg gtgcgacagg cccctggaca      3060
agggcttcag tggatgggat ggataaacac cgacagtgga gagtcaacat atgctgaaga      3120
gttcaaggga cggtttgtct ctccttgga cacctctgtc aacacggcat atctgcagat       3180
caccagcctc acggctgagg acactggcat gtatttctgt gtgagagtcg gctacgatgc      3240
tttggactac tgggccagg gaaccctggt caccgtctcg agcgcctcca caagggccc       3300 atcggtcttc cccctggcac cctcctccaa gagcacctct gggggcacag cggccctggg      3360
ctgcctggtc aaggactact tccccgaacc ggtgacggtg tcgtggaact caggcgccct      3420
gaccagcggc gtgcacacct tcccggctgt cctacagtcc tcaggactct actccctcag      3480
cagcgtggtg accgtgccct ccagcagctt gggcacccag acctacatct gcaacgtgaa      3540
tcacaagccc agcaacacca aggtggacaa gaaagttgag cccaaatctt gtgacaaaac      3600
tcacacatgc ccaccgtgcc cagcacctga actcctgggg ggaccgtcag tcttcctctt      3660 cccccaaaa cccaaggaca ccctcatgat ctcccggacc cctgaggtca catgcgtggt      3720
ggtggacgtg agccacgaag accctgaggt caagttcaac tggtacgtgg acggcgtgga      3780
ggtgcataat gccaagacaa agccgcggga ggagcagtac aacagcacgt accgggtggt      3840
cagcgtcctc accgtcctgc accaggactg gctgaatggc aaggagtaca gtgcaaggt      3900 ctccaacaaa gccctcccag cccccatcga gaaaaccatc tccaaagcca aagggcagcc      3960
ccgagaacca caggtgtaca ccctgccccc atcccgggag gagatgacca agaaccaggt      4020
```

```
cagcctgacc tgcctggtca aaggcttcta tcccagcgac atcgccgtgg agtgggagag   4080
caatgggcag ccggagaaca actacaagac cacgcctccc gtgctggact ccgacggctc   4140
cttcttcctc tacagcaagc tcaccgtgga caagagcagg tggcagcagg ggaacgtctt   4200
ctcatgctcc gtgatgcatg aggctctgca caaccactac acgcagaaga gcctctccct   4260
gtctccgggt aaatgagtgc gacggccggc aagccccgct ccccgggctc tcgcggtcgc   4320
acgaggatgc ttggcacgta ccccctgtac atacttcccg ggcgcccagc atggaaataa   4380
agcaccggat ctaataaaag atatttattt tcattagata tgtgtgttgg ttttttgtgt   4440
gcagtgcctc tatctggagg ccaggtaggg ctggccttgg gggaggggga ggccagaatg   4500
actccaagag ctacaggaag gcaggtcaga gaccccactg acaaacagt ggctggactc    4560
```

<210> SEQ ID NO 16
<211> LENGTH: 4560
<212> TYPE: DNA
<213> ORGANISM: Artificial sequence
<220> FEATURE:
<223> OTHER INFORMATION: pG4KD110-BARHcRKd construct sequence

<400> SEQUENCE: 16

```
tccttgacac gcgtctcggg aagcttgccg ccaccatgga catgagggtc cccgctcagc     60
tcctggggct cctgctgctc tggctcccag gtgccaaatg tgaaattgtg ttgacgcagt    120
ctccatcctc cctgtctgca tctgtaggag acagagtcac catcacttgc agtgccaggt    180
caagtgtaag ttacatgcac tggttccagc agaaaccagg gaaagcccct aagctctgga    240
tctataggac atccaacctg gcttctgggg tcccatctag attcagcggc agtggatctg    300
ggacatctta ctgtctcacc atcaacagcc tgcagcctga agattttgca acttactatt    360
gccagcaaag gagtagtttc ccactcacgt tcggcggagg gaccaagctg gagatcaaac    420
gtgagtggat ccatctggga taagcatgct gttttctgtc tgtccctaac atgccctgtg    480
attatgcgca aacaacacac ccaagggcag aactttgtta cttaaacacc atcctgtttg    540
cttctttcct caggaactgt ggctgcacca tctgtcttca tcttcccgcc atctgatgag    600
cagttgaaat ctggaactgc ctctgttgtg tgcctgctga taacttcta tcccagagag     660 gccaaagtac agtggaaggt ggataacgcc ctccaatcgg gtaactccca ggagagtgtc    720
acagagcagg acagcaagga cagcacctac agcctcagca gcaccctgac gctgagcaaa    780
gcagactacg agaaacacaa agtctacgcc tgcgaagtca cccatcaggg cctgagctcg    840
cccgtcacaa agagcttcaa caggggagag tgttagaggg agaagtgccc ccacctgctc    900
ctcagttcca gcctgacccc ctcccatcct ttggcctctg acccttttt cacaggggac     960 ctaccccctat tgcggtcctc cagctcatct ttcacctcac ccccctcctc ctccttggct   1020
ttaattatgc taatgttgga ggagaatgaa taaataaagt gaatctttgc acctgtggtg   1080
gatctaataa aagatattta ttttcattag atatgtgtgt tggttttttg tgtgcagtgc   1140
ctctatctgg aggccaggta gggctggcct tgggggaggg ggaggccaga atgactccaa   1200
gagctacagg aaggcaggtc agagacccca ctggacaaac agtggctgga ctctgcacca   1260
taacacacaa tcaacagggg agtgagctgg aaatttgcta gcgaattcta ttaatagtaa   1320
tcaattacgg ggtcattagt tcatagccca tatatggagt tccgcgttac ataacttacg   1380
gtaaatggcc cgcctggctg accgcccaac gacccccgcc cattgacgtc aataatgacg   1440
tatgttccca tagtaacgcc aatagggact ttccattgac gtcaatgggt ggagtattta   1500
cggtaaactg cccacttggc agtacatcaa gtgtatcata tgccaagtac gccccctatt   1560
```

-continued

| | | | |
|---|---|---|---|
| gacgtcaatg acggtaaatg gcccgcctgg cattatgccc agtacatgac cttatgggac | 1620 |
| tttcctactt ggcagtacat ctacgtatta gtcatcgcta ttaccatggt gatgcggttt | 1680 |
| tggcagtaca tcaatgggcg tggatagcgg tttgactcac ggggatttcc aagtctccac | 1740 |
| cccattgacg tcaatgggag tttgttttgg caccaaaatc aacgggactt tccaaaatgt | 1800 |
| cgtaacaact ccgccccatt gacgcaaatg ggcggtaggc gtgtacggtg gaggtctat | 1860 |
| ataagcagag ctcgtttagt gaaccgtcag atcgcctgga gacgccatcc acgctgtttt | 1920 |
| gacctccata gaagacaccg ggaccgatcc agcctccgcg gccgggaacg gtgcattgga | 1980 |
| acgcggattc cccgtgccaa gagtgacgta agtaccgcct atagagtcta taggcccacc | 2040 |
| cccttggctt cttatgcatg ctatactgtt tttggcttgg ggtctataca ccccgcttc | 2100 |
| ctcatgttat aggtgatggt atagcttagc ctataggtgt gggttattga ccattattga | 2160 |
| ccactcccct attggtgacg atactttcca ttactaatcc ataacatggc tctttgccac | 2220 |
| aactctcttt attggctata tgccaataca ctgtccttca gagactgaca cggactctgt | 2280 |
| attttacag gatggggtct catttattat ttacaaattc acatatacaa caccaccgtc | 2340 |
| cccagtgccc gcagttttta ttaaacataa cgtgggatct ccacgcgaat ctcgggtacg | 2400 |
| tgttccggac atgggctctt ctccggtagc ggcggagctt ctacatccga gccctgctcc | 2460 |
| catgcctcca gcgactcatg gtcgctcggc agctccttgc tcctaacagt ggaggccaga | 2520 |
| cttaggcaca gcacgatgcc caccaccacc agtgtgccgc acaaggccgt ggcggtaggg | 2580 |
| tatgtgtctg aaaatgagct cggggagcgg gcttgcaccg ctgacgcatt tggaagactt | 2640 |
| aaggcagcgg cagaagaaga tgcaggcagc tgagttgttg tgttctgata agagtcagag | 2700 |
| gtaactcccg ttgcggtgct gttaacggtg gagggcagtg tagtctgagc agtactcgtt | 2760 |
| gctgccgcgc gcgccaccag acataatagc tgacagacta acagactgtt cctttccatg | 2820 |
| ggtcttttct gcagtcaccg tccttgacac gcgtctcggg aagcttgccg ccaccatgga | 2880 |
| ctggacctgg aggatcctct tcttggtggc agcagcaaca ggtgcccact cccaggtgca | 2940 |
| gctggtgcaa tctgggtctg agcttaagaa gcctggggcc tcagtgaaga tctcctgcaa | 3000 |
| ggcttctgga tatactttca caaactatgg aatgaactgg gtgcgacagg cccctggaca | 3060 |
| agggcttcag tggatgggat ggataaacac cgacagtgga gagtcaacat atgctgaaga | 3120 |
| gttcaaggga cggtttgtct ctccttgga cacctctgtc aacacggcat atctgcagat | 3180 |
| caccagcctc acggctgagg acactggcat gtatttctgt gtgagagtcg gctacgatgc | 3240 |
| tttggactac tggggccagg gaaccctggt caccgtctcc tcaggtgagt ggatccacgt | 3300 |
| gctagctggc gcgcctcgag tttaaacgta cgagctttct ggggcaggcc gggcctgact | 3360 |
| ttggctgggg gcagggaggg ggctaaggtg acgcaggtgg cgccagccag gtgcacaccc | 3420 |
| aatgcccatg agcccagaca ctggaccctg catggaccat cgcggataga caagaaccga | 3480 |
| ggggcctctg cgccctgggc ccagctctgt cccacaccgc ggtcacatgg cacctgtcga | 3540 |
| cctgcagctt ccaccaaggg cccatccgtc ttccccctgg cgccctgctc caggagcacc | 3600 |
| tccgagagca gccgcccct gggctgcctg gtcaaggact acttccccga accggtgacg | 3660 |
| gtgtcgtgga actcaggcgc cctgaccagc ggcgtgcaca ccttcccggc tgtcctacag | 3720 |
| tcctcaggac tctactccct cagcagcgtg gtgaccgtgc cctccagcag cttgggcacg | 3780 |
| aagacctaca cctgcaacgt agatcacaag cccagcaaca ccaaggtgga caagagagtt | 3840 |
| gagtccaaat atggtccccc atgcccatca tgcccagcac ctgagttcct ggggggacca | 3900 |
| tcagtcttcc tgttcccccc aaaacccaag gacactctca tgatctcccg gacccctgag | 3960 |

```
gtcacgtgcg tggtggtgga cgtgagccag aagaccccg aggtccagtt caactggtac    4020
gtggatggcg tggaggtgca taatgccaag acaaagccgc gggaggagca gttcaacagc    4080
acgtaccgtg tggtcagcgt cctcaccgtc ctgcaccagg actggctgaa cggcaaggag    4140
tacaagtgca aggtctccaa caaaggcctc ccgtcctcca tcgagaaaac catctccaaa    4200
gccaaagggc agccccgaga gccacaggtg tacaccctgc ccccatccca ggaggagatg    4260
accaagaacc aggtcagcct gacctgcctg gtcaaaggct tctacccag cgacatcgcc    4320 gtggagtggg agagcaatgg gcagccggag aacaactaca agaccacgcc tcccgtgctg    4380
gactccgacg gctccttctt cctctacagc aggctaaccg tggacaagag caggtggcag    4440 gagggaatg tcttctcatg ctccgtgatg catgaggctc tgcacaacca ctacacacag    4500
aagagcctct ccctgtctct gggtaaatga gtgccagggc cggcaagccc ccgctccccg    4560
```

<210> SEQ ID NO 17
<211> LENGTH: 466
<212> TYPE: PRT
<213> ORGANISM: Artificial sequence
<220> FEATURE:
<223> OTHER INFORMATION: Heavy chain 1 translated protein sequence

<400> SEQUENCE: 17

```
Met Asp Trp Thr Trp Arg Ile Leu Phe Leu Val Ala Ala Ala Thr Gly
1               5                   10                  15

Ala His Ser Gln Val Gln Leu Val Gln Ser Gly Ser Glu Leu Lys Lys
            20                  25                  30

Pro Gly Ala Ser Val Lys Ile Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Gln Trp Met Gly Trp Ile Asn Thr Asp Ser Gly Glu Ser Thr Tyr Ala
65                  70                  75                  80

Glu Glu Phe Lys Gly Arg Phe Val Phe Ser Leu Asp Thr Ser Val Asn
                85                  90                  95

Thr Ala Tyr Leu Gln Ile Thr Ser Leu Thr Ala Glu Asp Thr Gly Met
            100                 105                 110

Tyr Phe Cys Val Arg Val Gly Tyr Asp Ala Leu Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Phe Leu Gly Gly
                245                 250                 255

Pro Ser Val Phe Leu Phe Pro Pro Lys Pro Lys Asp Thr Leu Met Ile
            260                 265                 270
```

Ser Arg Thr Pro Glu Val Thr Cys Val Val Asp Val Ser His Glu
        275                 280                 285

Asp Pro Glu Val Lys Phe Asn Trp Tyr Val Asp Gly Val Glu Val His
        290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
            325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
            405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 18
<211> LENGTH: 449
<212> TYPE: PRT
<213> ORGANISM: Artificial sequence
<220> FEATURE:
<223> OTHER INFORMATION: Heavy chain 1 Apo translated protein sequence

<400> SEQUENCE: 18

Glu Phe Gln Val Gln Leu Val Gln Ser Gly Ser Glu Leu Lys Lys Pro
1               5                   10                  15

Gly Ala Ser Val Lys Ile Ser Cys Lys Ala Ser Gly Tyr Thr Phe Thr
            20                  25                  30

Asn Tyr Gly Met Asn Trp Val Arg Gln Ala Pro Gly Gln Gly Leu Gln
        35                  40                  45

Trp Met Gly Trp Ile Asn Thr Asp Ser Gly Glu Ser Thr Tyr Ala Glu
    50                  55                  60

Glu Phe Lys Gly Arg Phe Val Phe Ser Leu Asp Thr Ser Val Asn Thr
65                  70                  75                  80

Ala Tyr Leu Gln Ile Thr Ser Leu Thr Ala Glu Asp Thr Gly Met Tyr
            85                  90                  95

Phe Cys Val Arg Val Gly Tyr Asp Ala Leu Asp Tyr Trp Gly Gln Gly
            100                 105                 110

Thr Leu Val Thr Val Ser Ser Ala Ser Thr Lys Gly Pro Ser Val Phe
    115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 19
<211> LENGTH: 450
<212> TYPE: PRT
<213> ORGANISM: Artificial sequence
<220> FEATURE:
<223> OTHER INFORMATION: Heavy chain 1 ER translated protein sequence

<400> SEQUENCE: 19

Glu Phe Gln Val Gln Leu Val Gln Ser Gly Ser Glu Leu Lys Lys Pro
1               5                   10                  15

Gly Ala Ser Val Lys Ile Ser Cys Lys Ala Ser Gly Tyr Thr Phe Thr
            20                  25                  30

Asn Tyr Gly Met Asn Trp Val Arg Gln Ala Pro Gly Gln Gly Leu Gln
        35                  40                  45

Trp Met Gly Trp Ile Asn Thr Asp Ser Gly Glu Ser Thr Tyr Ala Glu
    50                  55                  60

Glu Phe Lys Gly Arg Phe Val Phe Ser Leu Asp Thr Ser Val Asn Thr
65                  70                  75                  80

```
Ala Tyr Leu Gln Ile Thr Ser Leu Thr Ala Glu Asp Thr Gly Met Tyr
                85                  90                  95

Phe Cys Val Arg Val Gly Tyr Asp Ala Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Ser
    450

<210> SEQ ID NO 20
<211> LENGTH: 456
<212> TYPE: PRT
<213> ORGANISM: Artificial sequence
<220> FEATURE:
<223> OTHER INFORMATION: Heavy chain 1 Vac translated protein sequence
```

<400> SEQUENCE: 20

```
Glu Phe Gln Val Gln Leu Val Gln Ser Gly Ser Glu Leu Lys Lys Pro
1               5                   10                  15
Gly Ala Ser Val Lys Ile Ser Cys Lys Ala Ser Gly Tyr Thr Phe Thr
            20                  25                  30
Asn Tyr Gly Met Asn Trp Val Arg Gln Ala Pro Gly Gln Gly Leu Gln
        35                  40                  45
Trp Met Gly Trp Ile Asn Thr Asp Ser Gly Glu Ser Thr Tyr Ala Glu
50                  55                  60
Glu Phe Lys Gly Arg Phe Val Phe Ser Leu Asp Thr Ser Val Asn Thr
65                  70                  75                  80
Ala Tyr Leu Gln Ile Thr Ser Leu Thr Ala Glu Asp Thr Gly Met Tyr
                85                  90                  95
Phe Cys Val Arg Val Gly Tyr Asp Ala Leu Asp Tyr Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
210                 215                 220
Thr His Thr Cys Pro Pro Cys Pro Ala Pro Glu Phe Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
```

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys Gly Leu Leu Val Asp Thr Met
    450                 455

<210> SEQ ID NO 21
<211> LENGTH: 463
<212> TYPE: PRT
<213> ORGANISM: Artificial sequence
<220> FEATURE:
<223> OTHER INFORMATION: Heavy chain 4 translated protein sequence

<400> SEQUENCE: 21

Met Asp Trp Thr Trp Arg Ile Leu Phe Leu Val Ala Ala Thr Gly
1               5                   10                  15

Ala His Ser Gln Val Gln Leu Val Gln Ser Gly Ser Glu Leu Lys Lys
            20                  25                  30

Pro Gly Ala Ser Val Lys Ile Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Gln Trp Met Gly Trp Ile Asn Thr Asp Ser Gly Glu Ser Thr Tyr Ala
65                  70                  75                  80

Glu Glu Phe Lys Gly Arg Phe Val Phe Ser Leu Asp Thr Ser Val Asn
                85                  90                  95

Thr Ala Tyr Leu Gln Ile Thr Ser Leu Thr Ala Glu Asp Thr Gly Met
            100                 105                 110

Tyr Phe Cys Val Arg Val Gly Tyr Asp Ala Leu Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Lys Thr Tyr Thr Cys Asn Val Asp His Lys
    210                 215                 220

Pro Ser Asn Thr Lys Val Asp Lys Arg Val Glu Ser Lys Tyr Gly Pro
225                 230                 235                 240

Pro Cys Pro Ser Cys Pro Ala Pro Glu Phe Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser Gln Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Tyr Arg Val Val Ser
305                 310                 315                 320

Val Leu Thr Val Leu His Gln Asp Trp Leu Asn Gly Lys Glu Tyr Lys
            325                 330                 335

Cys Lys Val Ser Asn Lys Gly Leu Pro Ser Ser Ile Glu Lys Thr Ile
            340                 345                 350

Ser Lys Ala Lys Gly Gln Pro Arg Glu Pro Gln Val Tyr Thr Leu Pro
            355                 360                 365

Pro Ser Gln Glu Glu Met Thr Lys Asn Gln Val Ser Leu Thr Cys Leu
        370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Arg Leu Thr Val Asp Lys Ser Arg
            420                 425                 430

Trp Gln Glu Gly Asn Val Phe Ser Cys Ser Val Met His Glu Ala Leu
        435                 440                 445

His Asn His Tyr Thr Gln Lys Ser Leu Ser Leu Ser Leu Gly Lys
    450                 455                 460

<210> SEQ ID NO 22
<211> LENGTH: 446
<212> TYPE: PRT
<213> ORGANISM: Artificial sequence
<220> FEATURE:
<223> OTHER INFORMATION: Heavy chain 4 Apo translated protein sequence

<400> SEQUENCE: 22

Glu Phe Gln Val Gln Leu Val Gln Ser Gly Ser Glu Leu Lys Lys Pro
1               5                   10                  15

Gly Ala Ser Val Lys Ile Ser Cys Lys Ala Ser Gly Tyr Thr Phe Thr
            20                  25                  30

Asn Tyr Gly Met Asn Trp Val Arg Gln Ala Pro Gly Gln Gly Leu Gln
        35                  40                  45

Trp Met Gly Trp Ile Asn Thr Asp Ser Gly Glu Ser Thr Tyr Ala Glu
    50                  55                  60

Glu Phe Lys Gly Arg Phe Val Phe Ser Leu Asp Thr Ser Val Asn Thr
65                  70                  75                  80

Ala Tyr Leu Gln Ile Thr Ser Leu Thr Ala Glu Asp Thr Gly Met Tyr
                85                  90                  95

Phe Cys Val Arg Val Gly Tyr Asp Ala Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Ser Cys Pro Ala Pro Glu Phe Leu Gly Gly Pro Ser Val Phe

```
                    225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
                275                 280                 285

Lys Pro Arg Glu Glu Gln Phe Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu Gly Lys
            435                 440                 445

<210> SEQ ID NO 23
<211> LENGTH: 449
<212> TYPE: PRT
<213> ORGANISM: Artificial sequence
<220> FEATURE:
<223> OTHER INFORMATION: Heavy chain 4 ER translated protein sequence

<400> SEQUENCE: 23

Glu Phe Gln Val Gln Leu Val Gln Ser Gly Ser Glu Leu Lys Lys Pro
1               5                   10                  15

Gly Ala Ser Val Lys Ile Ser Cys Lys Ala Ser Gly Tyr Thr Phe Thr
                20                  25                  30

Asn Tyr Gly Met Asn Trp Val Arg Gln Ala Pro Gly Gln Gly Leu Gln
            35                  40                  45

Trp Met Gly Trp Ile Asn Thr Asp Ser Gly Glu Ser Thr Tyr Ala Glu
    50                  55                  60

Glu Phe Lys Gly Arg Phe Val Phe Ser Leu Asp Thr Ser Val Asn Thr
65                  70                  75                  80

Ala Tyr Leu Gln Ile Thr Ser Leu Thr Ala Glu Asp Thr Gly Met Tyr
                85                  90                  95

Phe Cys Val Arg Val Gly Tyr Asp Ala Leu Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
        130                 135                 140

Gly Cys Leu Val Lys Asp Tyr Phe Pro Glu Pro Val Thr Val Ser Trp
145                 150                 155                 160
```

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
            210                 215                 220

Cys Pro Ser Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
            405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys Ser Thr
            435                 440                 445

Lys

<210> SEQ ID NO 24
<211> LENGTH: 453
<212> TYPE: PRT
<213> ORGANISM: Artificial sequence
<220> FEATURE:
<223> OTHER INFORMATION: Heavy chain 4 Vac translated protein sequence

<400> SEQUENCE: 24

Glu Phe Gln Val Gln Leu Val Gln Ser Gly Ser Glu Leu Lys Lys Pro
1               5                   10                  15

Gly Ala Ser Val Lys Ile Ser Cys Lys Ala Ser Gly Tyr Thr Phe Thr
            20                  25                  30

Asn Tyr Gly Met Asn Trp Val Arg Gln Ala Pro Gly Gln Gly Leu Gln
            35                  40                  45

Trp Met Gly Trp Ile Asn Thr Asp Ser Gly Glu Ser Thr Tyr Ala Glu
            50                  55                  60

Glu Phe Lys Gly Arg Phe Val Phe Ser Leu Asp Thr Ser Val Asn Thr

```
                65                  70                  75                  80
            Ala Tyr Leu Gln Ile Thr Ser Leu Thr Ala Glu Asp Thr Gly Met Tyr
                                85                  90                  95

Phe Cys Val Arg Val Gly Tyr Asp Ala Leu Asp Tyr Trp Gly Gln Gly
                            100                 105                 110

Thr Leu Val Thr Val Ser Ser Ala Ser Thr Lys Gly Pro Ser Val Phe
                        115                 120                 125

Pro Leu Ala Pro Cys Ser Arg Ser Thr Ser Glu Ser Thr Ala Ala Leu
                    130                 135                 140

Gly Cys Leu Val Lys Asp Tyr Phe Pro Glu Pro Val Thr Val Ser Trp
            145                 150                 155                 160

Asn Ser Gly Ala Leu Thr Ser Gly Val His Thr Phe Pro Ala Val Leu
                            165                 170                 175

Gln Ser Ser Gly Leu Tyr Ser Leu Ser Ser Val Val Thr Val Pro Ser
                        180                 185                 190

Ser Ser Leu Gly Thr Lys Thr Tyr Thr Cys Asn Val Asp His Lys Pro
                    195                 200                 205

Ser Asn Thr Lys Val Asp Lys Arg Val Glu Ser Lys Tyr Gly Pro Pro
                210                 215                 220

Cys Pro Ser Cys Pro Ala Pro Glu Phe Leu Gly Gly Pro Ser Val Phe
            225                 230                 235                 240

Leu Phe Pro Pro Lys Pro Lys Asp Thr Leu Met Ile Ser Arg Thr Pro
                            245                 250                 255

Glu Val Thr Cys Val Val Val Asp Val Ser Gln Glu Asp Pro Glu Val
                        260                 265                 270

Gln Phe Asn Trp Tyr Val Asp Gly Val Glu Val His Asn Ala Lys Thr
                    275                 280                 285

Lys Pro Arg Glu Glu Gln Phe Asn Ser Thr Tyr Arg Val Val Ser Val
                290                 295                 300

Leu Thr Val Leu His Gln Asp Trp Leu Asn Gly Lys Glu Tyr Lys Cys
            305                 310                 315                 320

Lys Val Ser Asn Lys Gly Leu Pro Ser Ser Ile Glu Lys Thr Ile Ser
                            325                 330                 335

Lys Ala Lys Gly Gln Pro Arg Glu Pro Gln Val Tyr Thr Leu Pro Pro
                        340                 345                 350

Ser Gln Glu Glu Met Thr Lys Asn Gln Val Ser Leu Thr Cys Leu Val
                    355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
            385                 390                 395                 400

Gly Ser Phe Phe Leu Tyr Ser Arg Leu Thr Val Asp Lys Ser Arg Trp
                            405                 410                 415

Gln Glu Gly Asn Val Phe Ser Cys Ser Val Met His Glu Ala Leu His
                        420                 425                 430

Asn His Tyr Thr Gln Lys Ser Leu Ser Leu Ser Leu Gly Lys Gly Leu
                    435                 440                 445

Leu Val Asp Thr Met
                450

<210> SEQ ID NO 25
<211> LENGTH: 235
<212> TYPE: PRT
<213> ORGANISM: Artificial sequence
<220> FEATURE:
```

-continued

<223> OTHER INFORMATION: Light chain translated protein sequence

<400> SEQUENCE: 25

Met Asp Met Arg Val Pro Ala Gln Leu Leu Gly Leu Leu Leu Leu Trp
1               5                   10                  15

Leu Pro Gly Ala Lys Cys Glu Ile Val Leu Thr Gln Ser Pro Ser Ser
            20                  25                  30

Leu Ser Ala Ser Val Gly Asp Arg Val Thr Ile Thr Cys Ser Ala Arg
        35                  40                  45

Ser Ser Val Ser Tyr Met His Trp Phe Gln Gln Lys Pro Gly Lys Ala
    50                  55                  60

Pro Lys Leu Trp Ile Tyr Arg Thr Ser Asn Leu Ala Ser Gly Val Pro
65                  70                  75                  80

Ser Arg Phe Ser Gly Ser Gly Ser Gly Thr Ser Tyr Cys Leu Thr Ile
                85                  90                  95

Asn Ser Leu Gln Pro Glu Asp Phe Ala Thr Tyr Tyr Cys Gln Gln Arg
            100                 105                 110

Ser Ser Phe Pro Leu Thr Phe Gly Gly Gly Thr Lys Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 26
<211> LENGTH: 215
<212> TYPE: PRT
<213> ORGANISM: Artificial sequence
<220> FEATURE:
<223> OTHER INFORMATION: Light chain Apo translated protein sequence

<400> SEQUENCE: 26

Glu Phe Glu Ile Val Leu Thr Gln Ser Pro Ser Ser Leu Ser Ala Ser
1               5                   10                  15

Val Gly Asp Arg Val Thr Ile Thr Cys Ser Ala Arg Ser Ser Val Ser
            20                  25                  30

Tyr Met His Trp Phe Gln Gln Lys Pro Gly Lys Ala Pro Lys Leu Trp
        35                  40                  45

Ile Tyr Arg Thr Ser Asn Leu Ala Ser Gly Val Pro Ser Arg Phe Ser
    50                  55                  60

Gly Ser Gly Ser Gly Thr Ser Tyr Cys Leu Thr Ile Asn Ser Leu Gln
65                  70                  75                  80

Pro Glu Asp Phe Ala Thr Tyr Tyr Cys Gln Gln Arg Ser Ser Phe Pro
                85                  90                  95

Leu Thr Phe Gly Gly Gly Thr Lys Leu Glu Ile Lys Arg Thr Val Ala
            100                 105                 110

```
Ala Pro Ser Val Phe Ile Phe Pro Ser Asp Glu Gln Leu Lys Ser
        115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
        210                 215

<210> SEQ ID NO 27
<211> LENGTH: 216
<212> TYPE: PRT
<213> ORGANISM: Artificial sequence
<220> FEATURE:
<223> OTHER INFORMATION: Light chain ER translated protein sequence

<400> SEQUENCE: 27

Glu Phe Glu Ile Val Leu Thr Gln Ser Pro Ser Ser Leu Ser Ala Ser
1               5                   10                  15

Val Gly Asp Arg Val Thr Ile Thr Cys Ser Ala Arg Ser Ser Val Ser
                20                  25                  30

Tyr Met His Trp Phe Gln Gln Lys Pro Gly Lys Ala Pro Lys Leu Trp
            35                  40                  45

Ile Tyr Arg Thr Ser Asn Leu Ala Ser Gly Val Pro Ser Arg Phe Ser
50                  55                  60

Gly Ser Gly Ser Gly Thr Ser Tyr Cys Leu Thr Ile Asn Ser Leu Gln
65                  70                  75                  80

Pro Glu Asp Phe Ala Thr Tyr Tyr Cys Gln Gln Arg Ser Ser Phe Pro
                85                  90                  95

Leu Thr Phe Gly Gly Gly Thr Lys Leu Glu Ile Lys Arg Thr Val Ala
                100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys Ser
        210                 215

<210> SEQ ID NO 28
<211> LENGTH: 222
<212> TYPE: PRT
<213> ORGANISM: Artificial sequence
<220> FEATURE:
<223> OTHER INFORMATION: Light chain Vac translated protein sequence
```

```
<400> SEQUENCE: 28

Glu Phe Glu Ile Val Leu Thr Gln Ser Pro Ser Ser Leu Ser Ala Ser
1               5                   10                  15

Val Gly Asp Arg Val Thr Ile Thr Cys Ser Ala Arg Ser Ser Val Ser
            20                  25                  30

Tyr Met His Trp Phe Gln Gln Lys Pro Gly Lys Ala Pro Lys Leu Trp
        35                  40                  45

Ile Tyr Arg Thr Ser Asn Leu Ala Ser Gly Val Pro Ser Arg Phe Ser
    50                  55                  60

Gly Ser Gly Ser Gly Thr Ser Tyr Cys Leu Thr Ile Asn Ser Leu Gln
65                  70                  75                  80

Pro Glu Asp Phe Ala Thr Tyr Tyr Cys Gln Gln Arg Ser Ser Phe Pro
                85                  90                  95

Leu Thr Phe Gly Gly Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Leu Leu Val Asp Thr Met
    210                 215                 220
```